US012727813B2

(12) United States Patent
Wang et al.

(10) Patent No.: US 12,727,813 B2
(45) Date of Patent: Sep. 8, 2026

(54) SYSTEMS AND METHODS FOR UTERINE PERISTALSIS IMAGING

(71) Applicant: Washington University, St. Louis, MO (US)

(72) Inventors: Yong Wang, St. Louis, MO (US); Sicheng Wang, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 19/111,616

(22) PCT Filed: Sep. 14, 2023

(86) PCT No.: PCT/US2023/032765
§ 371 (c)(1),
(2) Date: Mar. 13, 2025

(87) PCT Pub. No.: WO2024/059211
PCT Pub. Date: Mar. 21, 2024

(65) Prior Publication Data

US 2026/0083391 A1 Mar. 26, 2026

Related U.S. Application Data

(60) Provisional application No. 63/406,914, filed on Sep. 15, 2022.

(51) Int. Cl.
*A61B 5/00* (2006.01)
*A61B 5/055* (2006.01)
(Continued)

(52) U.S. Cl.
CPC .......... *A61B 5/4325* (2013.01); *A61B 5/0035* (2013.01); *A61B 5/004* (2013.01);
(Continued)

(58) Field of Classification Search
CPC ........ A61B 2090/3954; A61B 2576/02; A61B 5/0035; A61B 5/0064; A61B 5/004;
(Continued)

(56) References Cited

U.S. PATENT DOCUMENTS 8,682,423 B2 3/2014 Calderon et al.
10,602,951 B2 3/2020 Young
(Continued)

OTHER PUBLICATIONS

International Search Report and Written Opinion of PCT Application No. PCT/US2023/032765, dated Feb. 15, 2024, 11 pages.

*Primary Examiner* — Keith M Raymond
*Assistant Examiner* — Milton Truong
(74) *Attorney, Agent, or Firm* — Polsinelli PC

(57) ABSTRACT

Uterine peristalsis imaging (UPI) can provide objective, quantitative measures of uterine peristalsis (UP). Unlike other modalities, the contractile activity seen during UP can be quantitatively measured and reliably observed with UPI. With 3D accuracy, which takes into consideration the individual's unique uterine anatomy, the site of initiation and termination of the contraction are mapped along with the characterization of the direction, duration, and magnitude of the contractile forces. Novel peristalsis indices were developed for quantitative characterization of uterine contractile patterns. This includes measuring the duration and magnitude of UP. This assessment can be performed in a noninvasive way with little patient discomfort for a prolonged period.

20 Claims, 56 Drawing Sheets
(51 of 56 Drawing Sheet(s) Filed in Color)

(51) Int. Cl.

| | |
|---|---|
| ***A61B 5/257*** | (2021.01) |
| ***A61B 5/296*** | (2021.01) |
| ***A61B 8/00*** | (2006.01) |
| ***A61B 8/12*** | (2006.01) |
| ***A61B 90/00*** | (2016.01) |
| ***G16H 30/40*** | (2018.01) |

(52) U.S. Cl.

CPC .............. *A61B 5/055* (2013.01); *A61B 5/257* (2021.01); *A61B 5/296* (2021.01); *A61B 8/12* (2013.01); *A61B 8/5261* (2013.01); *A61B 90/39* (2016.02); *G16H 30/40* (2018.01); *A61B 2090/3908* (2016.02); *A61B 2090/3954* (2016.02); *A61B 2576/02* (2013.01)

(58) Field of Classification Search

CPC ..... A61B 5/391; A61B 5/4325; A61B 8/5261; A61B 2090/3908; A61B 5/055; A61B 5/1107; A61B 5/1128; A61B 5/257; A61B 5/296; A61B 8/085; A61B 8/12; A61B 90/39; G01R 33/4808; G01R 33/56325

See application file for complete search history.

(56) References Cited

U.S. PATENT DOCUMENTS

| | | | | |
|---|---|---|---|---|
| 11,234,634 | B2 | 2/2022 | Mischi et al. | |
| 2020/0245923 | A1* | 8/2020 | Cahill | A61B 5/4356 |
| 2021/0228147 | A1* | 7/2021 | Wang | G06T 7/0012 |
| 2023/0233189 | A1* | 7/2023 | Mischi | A61B 5/4356<br>382/128 |

* cited by examiner

*FIG. 4*

Anterior View
Posterior View
Left View
Right View
A
P
551
552
553
554
555
556
557
558
Time (s)

109
110
111
112
113
114

F
C
542
543
544
545

174
175
176
177
178
179
180

A
Menses
Anterior View
Posterior View
Left View
Right View
57 58 59 60

B
Menses
Anterior View
Posterior View
Left View
Right View
159 160 161 162 163

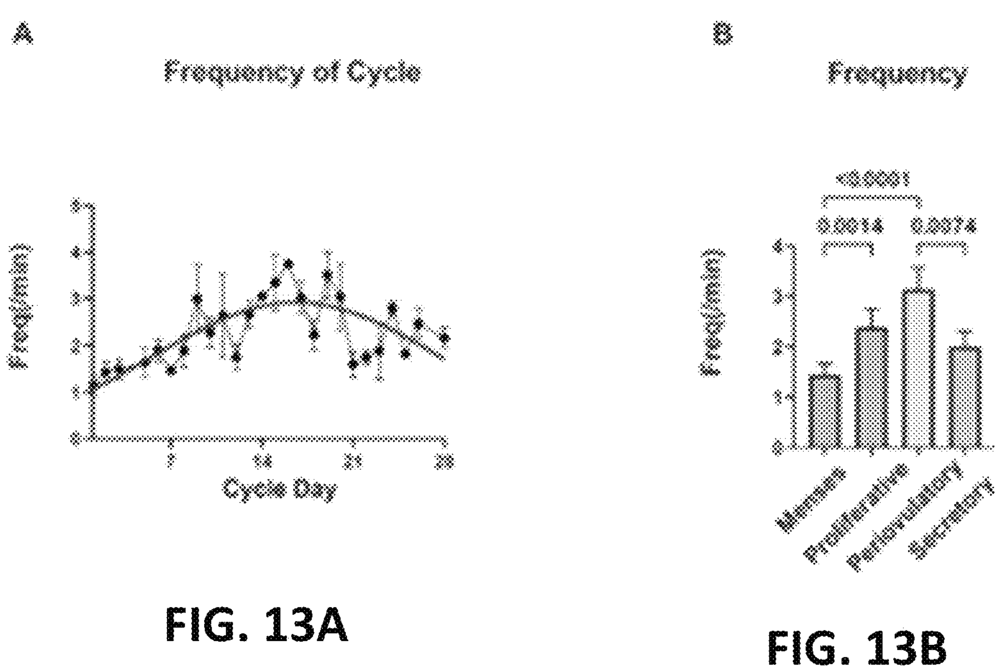
FIG. 13A
FIG. 13B
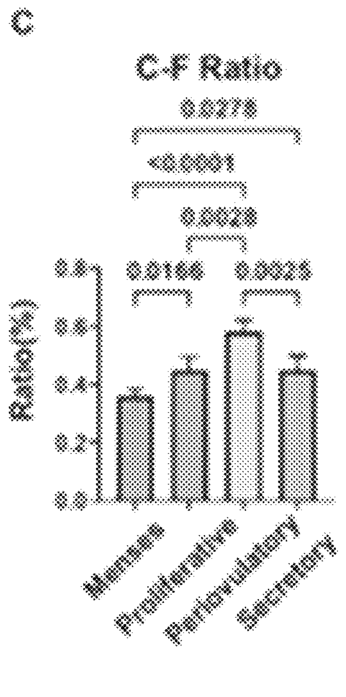
FIG. 13C
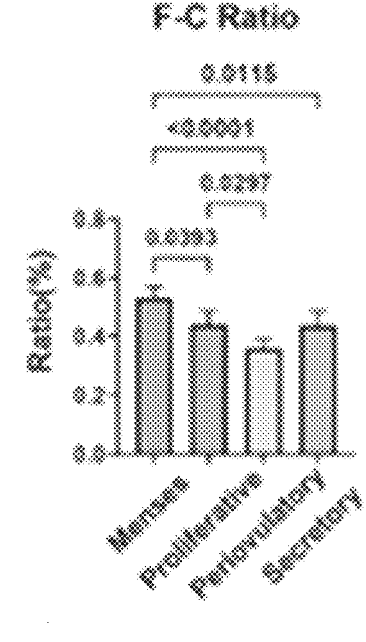
FIG. 13D

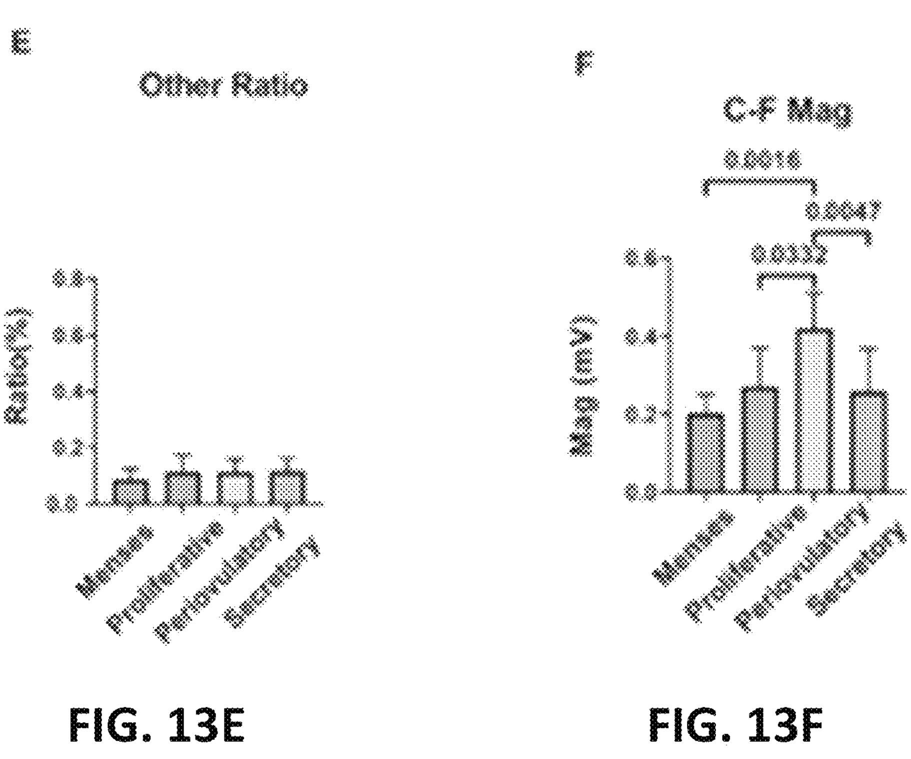
FIG. 13E
FIG. 13F
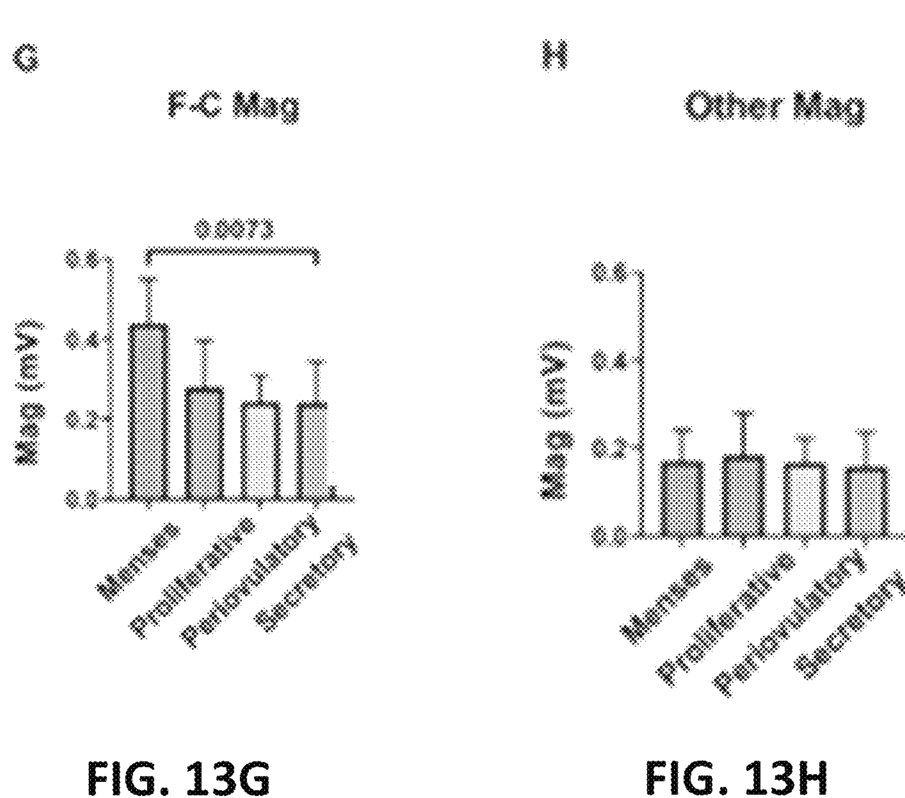
FIG. 13G
FIG. 13H

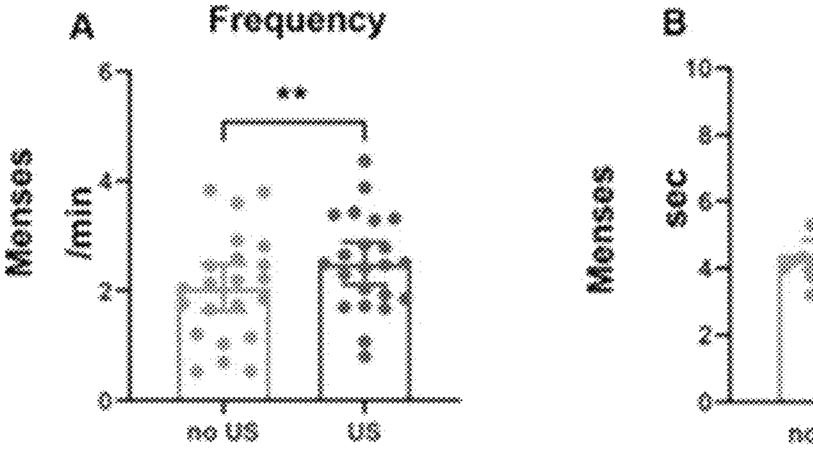
FIG. 17A
FIG. 17B
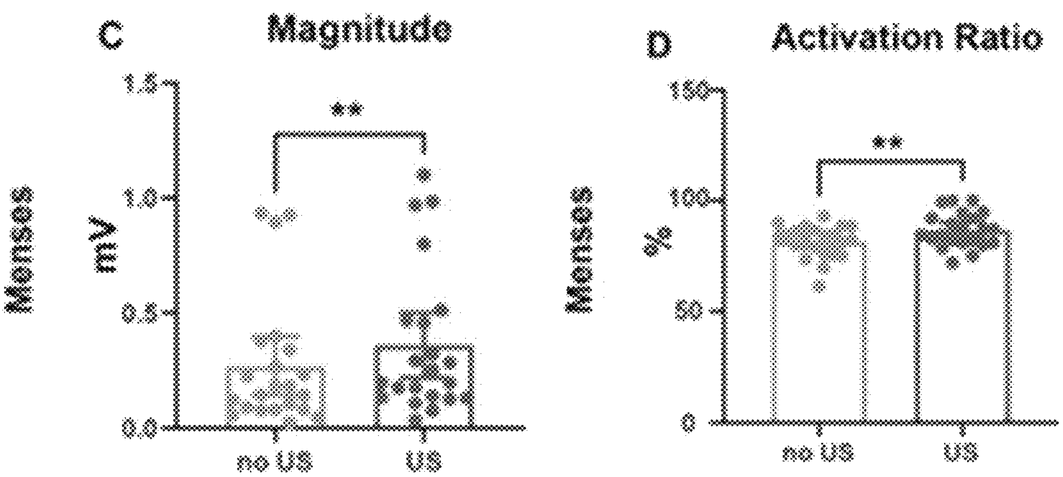
FIG. 17C
FIG. 17D

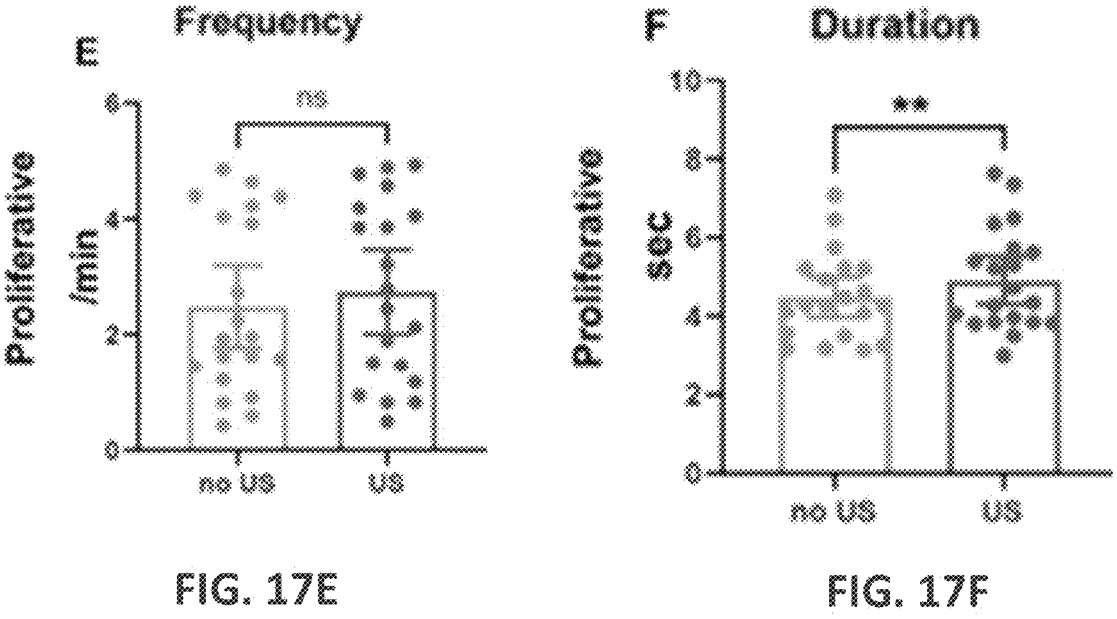
FIG. 17E
FIG. 17F
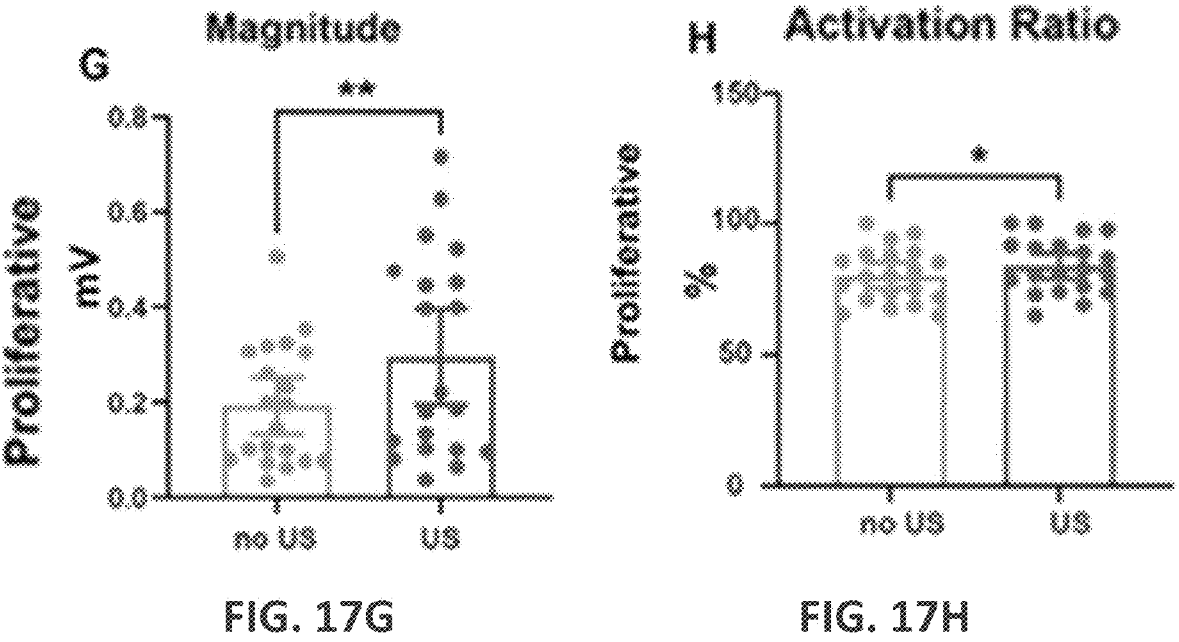
FIG. 17G
FIG. 17H

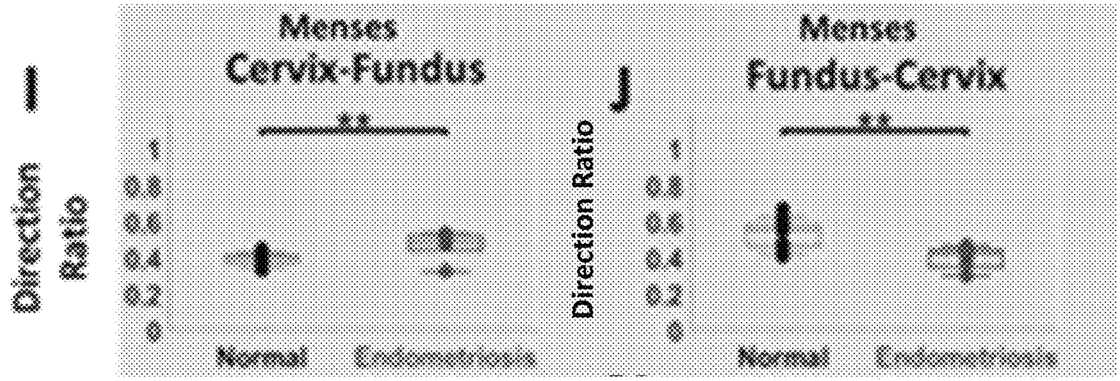
FIG. 21I
FIG. 21J
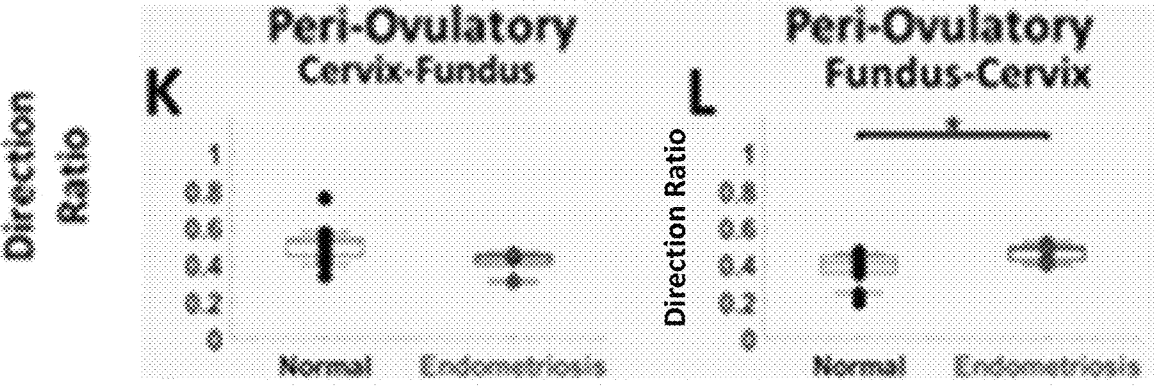
FIG. 21K
FIG. 21L

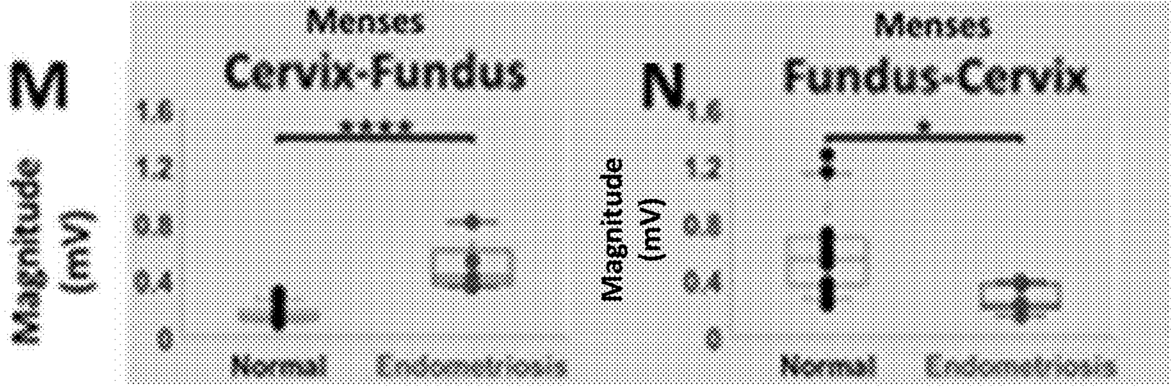
FIG. 21M
FIG. 21N
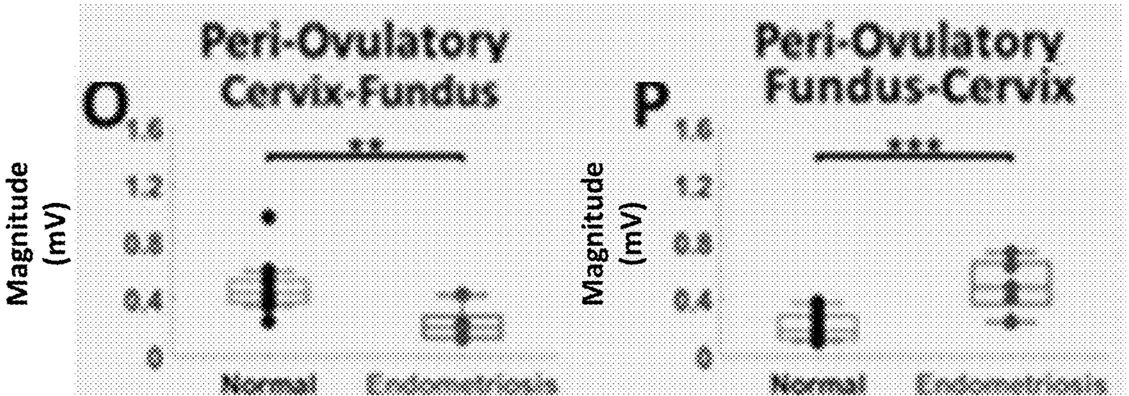
FIG. 21O
FIG. 21P

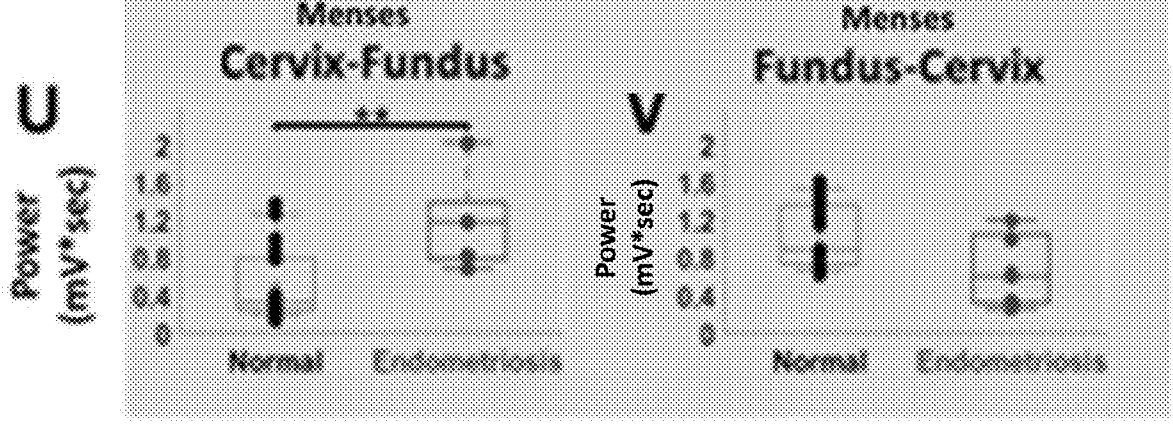
FIG. 21U
FIG. 21V
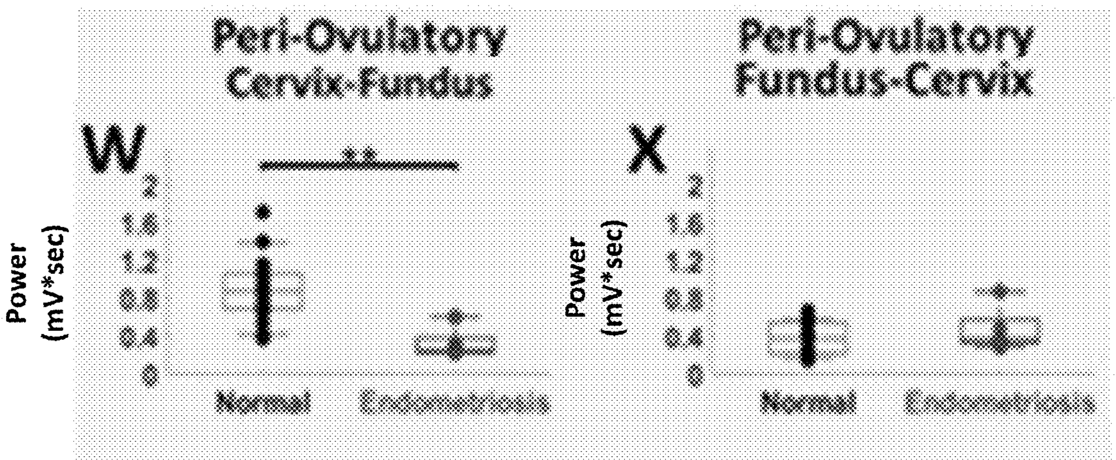
FIG. 21W
FIG. 21X

SYSTEMS AND METHODS FOR UTERINE PERISTALSIS IMAGING

CROSS-REFERENCE TO RELATED APPLICATIONS

This application claims priority to U.S. Provisional Application Ser. No. 63/406,914 filed on Sep. 15, 2022, which is incorporated herein by reference in its entirety.

TECHNICAL FIELD

The present disclosure is directed to systems and methods for reconstructing three-dimensional images representative of uterine electrical activity during a uterine contraction and more particularly to noninvasively imaging the three-dimensional uterine peristalsis pattern.

BACKGROUND

From puberty to menopause, a woman's uterus is either cyclically preparing for a pregnancy, maintaining, and delivering a pregnancy, involuting postpartum or quiescent during lactation. Unlike every other organ, which generally functions in the same manner continuously throughout an organism's life, the uterus functions in vastly different manners during different times in a female's life. During pregnancy, the uterus protects the amniotic fluid, expands to accommodate fetal growth, and nourishes the developing fetus through the placenta. After delivery, the uterus contracts to prevent hemorrhage and quickly returns to its pre-pregnancy size. During the non-obstetrical portion of female's life (which can total 29 years in a woman who bears two children), the uterus prepares for pregnancy through the menstrual cycle. Although this portion is the majority of a female's reproductive span, knowledge of uterine peristalsis (UP) at different phases of the menstrual cycle is lacking. A better understanding of physiologic UP may also help in diagnosing, monitoring, and treating uterine dysfunctions such as endometriosis (a painful disease in which endometrial cells implant and grow in the peritoneal space), dysmenorrhea (a disorder in which women have irregular, heavy, or painful menstruation), or implantation failure (embryo does not attach to the uterus).

Although a great deal is known about the hormonal regulation and physiology of the uterine epithelium (endometrium) during the menstrual cycle, little is known about myometrial physiology. Numerous studies have documented spontaneous, mild contractions from the inner layer of the myometrium (stratum subvasculare), termed uterine peristalsis. These studies have provided evidence that the pattern, direction, and frequency of these contractions vary throughout the phases of the menstrual cycle. Additional studies have suggested uterine peristalsis plays an important role in fertility and normal menstruation, and disruptions in uterine peristalsis may occur in women who experience infertility, endometriosis, or dysmenorrhea. However, these studies have all been greatly hindered by the limitations of the available technologies. As a result, the data are largely subjective, variable, and do not permit a rigorous, detailed analysis of normal myometrial physiology. Without such data, cause and effect in disease states cannot be determined. Oftentimes, gynecologists cannot easily diagnose uterine dysfunction, and therefore, they cannot determine which women will benefit the most from therapies or when in the menstrual cycle such therapies should be delivered.

Studies evaluating normal menses and gynecologic pathologies have all been greatly hindered by the limitations of the available technologies. The four main modalities are intrauterine pressure catheters (IUPC), transvaginal US (TVUS), hysterosalpingography (HSSG), and magnetic resonance imaging (MRI) s. Each has their own limitations either due to cost, time of procedure, invasiveness or variables that cannot be identified. Firstly, intrauterine pressure catheter (IUPC) is invasive, requiring the placement of a catheter into the uterus which can alter the characteristics of UP. Secondly, transvaginal ultrasound (TVUS) is invasive, and prolonged TVUS examinations cause mild to moderate discomfort or embarrassment during clinical studies. Additionally, UP initiation sites cannot be distinguished and the quality of TVUS UP measurement is dependent on the orientation of the ultrasound transducer, making it highly subjective and operator/time dependent, which creates inter-observer heterogeneity. Thirdly, hysterosalpingography (HSSG) is a radiological procedure to study the uterus and fallopian tubes. HSSG involves injection of radiographic contrast dye while obtaining x-rays. Although objective in its measurement, HSSG cannot measure amplitude or frequency, and it can only be used for a limited amount of time due to radiation exposure. Fourthly, magnetic resonance imaging (MRI) can be detected by Cine MRI imaging using T2-weighted sequences. This method produces multi-frame data. The presence of UP is usually detected visually by playing the MRI frames 12 times faster than the actual speed. MRI cannot readily be performed on the spot and cannot acquire sufficiently long periods of measurement due to the discomfort and limited accessibility. Therefore, none of the available tools are capable of quantitatively measuring UP across the entire menstrual cycle.

SUMMARY

Disclosed herein is a method for monitoring uterine peristalsis of a non-pregnant uterus of a mammal during at least one uterine contraction, the mammal having a body surface surrounding the uterus, the method comprising: applying a first patch to a plurality of locations on the body surface, the first patch associated with a plurality of imaging markers; performing a first imaging scan of the uterus of the mammal, wherein the first imaging scan generates a first set of three-dimensional images representing the body surface and uterus of the mammal; applying a second patch to the plurality of locations on the body surface, the second patch associated with an electrical recording device and an optical scanner, where the first patch is removed before applying the second patch to the plurality of locations; performing a second imaging scan of the uterus of the mammal, the second imaging scan associated with the optical scanner, wherein the second imaging scan generates a second set of three-dimensional images representing the body surface and uterus of the mammal; recording the body surface electrical potentials via the electrical recording device during the at least one uterine contraction, the recording device in electrical communication with the second patch; performing a third imaging scan of the uterus of the mammal, wherein the third imaging scan generates a set of two-dimensional images representing the body surface and uterus of the mammal; identifying a body-uterus geometry of the mammal based on at least one of the first and second set of generated three-dimensional images and the set of generated two-dimensional images; generating at least one body surface electrical potential map based on the identified body-uterus geometry and the body surface electrical potentials recorded at the plurality of locations by the electrical recording device during the at least one uterine contraction; and reconstructing the first and second set of three-dimensional images to provide a third set of three-dimensional images representative of the uterine peristalsis electrical activity of the non-pregnant uterus of the mammal during the at least one uterine contraction based on the identified body-uterus geometry of the mammal and the recorded body surface electrical potentials.

In some aspects, at least a portion of the plurality of imaging markers are visible in at least a portion of the first set of generated three-dimensional images. In various aspects, the plurality of locations includes at least 8 locations on the body surface of the mammal and/or the plurality of electrodes includes up to 64 electrodes. The number of the plurality of markers may be equal to the number of the plurality of electrodes. In an aspect, the first and second patches are releasably secured and operably connected to a wearable device.

The first imaging scan may be an MRI scan, the first set of generated three-dimensional images may include MRI images, and the plurality of imaging markers may include MRI markers. The reconstructed three-dimensional images may include at least one of a uterine surface electrical potential map, a set of electrograms, and a set of isochrone maps. In an aspect, the third imaging scan is a transvaginal ultrasound.

Further disclosed herein is a system for monitoring uterine peristalsis of a non-pregnant uterus of a mammal during at least one uterine contraction, the system comprising: a first patch operable to be secured to a plurality of locations on the body surface, the first patch associated with a plurality of imaging markers; a first imaging modality of the uterus of the mammal, wherein the first imaging modality generates a first set of three-dimensional images representing the body surface and uterus of the mammal; a second patch operable to replace the first patch at the plurality of locations on the body surface, wherein the first patch is removed before applying the second patch to the plurality of locations; a second imaging modality of the uterus of the mammal, the second imaging modality associated with an optical scanner, wherein the second imaging scan generates a second set of three-dimensional images representing the body surface and uterus of the mammal; an electrical recording device in electrical communication with the second patch, the electrical recording device configured to record body surface electrical potentials during the uterine contraction and to record a plurality of electrical signals on the body surface surrounding the uterus of the mammal during the uterine contraction; a third imaging modality of the uterus of the mammal, wherein the third imaging modality generates a set of two-dimensional images representing the body surface and uterus of the mammal; identifying a body-uterus geometry of the mammal based on at least one of the first and second set of generated three-dimensional images and the set of generated two-dimensional images; and at least one non-transitory computer readable medium storing instructions which when executed by at least one processor, cause the at least one processor to: receive the first set of generated three-dimensional images from the first imaging modality; determine the plurality of locations based on the imaging markers visible in the first set of generated three-dimensional images; receive the second set of generated three-dimensional images from the second imaging modality; receive the set of generated two-dimensional images from the third imagining modality; determine a body-uterus geometry of the mammal based on the first and second sets of three-dimensional images, the set of two-dimensional images, and the plurality of locations; receive the plurality of electrical signals from the electrical recording device; and generate at least one of a body surface electrical potential map based on the body-uterus geometry and the plurality of electrical signals.

In an aspect, the first patch is associated with a plurality of imaging markers and at least a portion of the plurality of imaging markers are visible in at least a portion of the first set of generated three-dimensional images. For example, at least a portion of the image markers are MRI image markers. The plurality of locations may include at least 8 locations on the body surface of the mammal. In some aspects, the first imaging modality may be an MRI scan, the first set of generated three-dimensional images may include MRI images, and the plurality of imaging markers may include MRI markers. The first imaging scan may be an MRI scan, the first set of generated three-dimensional images may include MRI images, and the plurality of imaging markers may include MRI markers.

In an aspect, the second patch includes a plurality of electrodes. The number of the first patches may be equal to the number of the second patches, the first patches may include at least one imaging marker, and the second patches may include at least one electrode. The first and second patches may be releasably secured and operably connected to a wearable device. The at least one generated three-dimensional body surface electrical potential map may be an electrical potential map, an electrogram, or an isochrone map. In an aspect, the third imaging modality is a transvaginal ultrasound.

Also disclosed herein is a method for monitoring uterine peristalsis of a non-pregnant uterus of a mammal during at least one uterine contraction, the mammal having a body surface surrounding the uterus, the method comprising: applying a plurality of imaging markers to a plurality of locations on the body surface, each one of the plurality of imaging markers applied to one of the plurality of locations; performing a first imaging scan of the uterus of the mammal, the first imaging scan operable to generate a first plurality of generated three-dimensional images of the body surface and uterus of the mammal; determining a first body-uterus geometry of the mammal based on the first plurality of generated three-dimensional images; replacing each one of the plurality of imaging markers applied to one of a plurality of locations, with one of a plurality of electrodes, each one of the plurality of electrodes associated with a second imaging scan and an electrical recording device; performing the second imaging scan of the uterus of the mammal, the second imaging scan operable to generate a second plurality of generated three-dimensional images of the body surface and uterus of the mammal; determining a second body-uterus geometry of the mammal based on the second plurality of generated three-dimensional images; recording the body surface electrical potentials via the electrical recording device during the at least one uterine contraction, the recording device in electrical communication with the plurality of electrodes; performing a third imaging scan of the uterus of the mammal, the third imaging scan operable to generate a plurality of generated two-dimensional images of the body surface and uterus of the mammal; generating a plurality of body surface electrical potential maps based on at least one of the first and second body-uterus geometries, the plurality of generated two-dimensional images, and the plurality of body surface electrical potentials detected at the plurality of locations during the at least one uterine contraction; and reconstructing at least one of the first and second plurality of generated three-dimensional images to provide a plurality of reconstructed three-dimensional images representative of the uterine peristalsis electrical activity of the uterus of the mammal during the at least one uterine contraction from the body-uterus geometry of the mammal and the plurality of body surface electrical potentials.

BRIEF DESCRIPTION OF THE FIGURES

The patent or application file contains at least one drawing executed in color. Copies of this patent or patent application publication with color drawing(s) will be provided by the Office upon request and payment of the necessary fee.

The description will be more fully understood with reference to the following figures and data graphs, which are presented as various embodiments of the disclosure and should not be construed as a complete recitation of the scope of the disclosure, wherein:

FIGS. 4A-C shows a detailed demonstration of uterine peristalsis from anterior, posterior, left, and right views.

FIGS. 13A-K show quantitative analysis of uterine peristalsis during each phase of the menstrual cycle. There were 26 participants in each phase. A P-value of less than 0.05 is marked in FIGS. 13A-K.

FIG. 13A shows longitudinal uterine peristalsis in a eumenorrheic 28-day menstrual cycle. Red curve was fitted using Gaussian distribution.

FIG. 13B shows peristalsis frequency at four phases in the normal menstrual cycle.

FIG. 13C shows a direction ratio of uterine peristalsis in a C-F (Cervix-Fundus) direction at four phases in the normal menstrual cycle.

FIG. 13D shows a direction ratio of uterine peristalsis in a F-C (Fundus-Cervix) direction at four phases in the normal menstrual cycle.

FIG. 13E shows a direction ratio of uterine peristalsis in other directions at four phases in the normal menstrual cycle.

FIG. 13F shows magnitude of uterine peristalsis in a C-F (Cervix-Fundus) direction at four phases in the normal menstrual cycle.

FIG. 13G shows magnitude of uterine peristalsis in a F-C (Fundus-Cervix) direction at four phases in the normal menstrual cycle.

FIG. 13H shows magnitude of uterine peristalsis in other directions at four phases in the normal menstrual cycle.

FIG. 13I shows power of uterine peristalsis in a C-F (Cervix-Fundus) direction at four phases in the normal menstrual cycle.

FIG. 13J shows power of uterine peristalsis in a F-C (Fundus-Cervix) direction at four phases in the normal menstrual cycle.

FIG. 13K shows power of uterine peristalsis in other directions at four phases in the normal menstrual cycle.

FIGS. 14A-R show unilateral UP patterns of normal patients with a developed dominant follicle during periovulation.

FIG. 14A shows a T2-weighted anatomical image of one healthy participant, where the blue segment is the uterine cavity and red segments are the follicles.

FIG. 14B shows a reconstructed 3D uterine geometry with two interstitial portions marked by red stars.

FIG. 14C shows multiple selected sequential isochrones maps of one patient with a right dominant follicle. Red decodes the initiation site and blue decodes the termination cite in each subpanel.

FIGS. 14I-R show termination probability maps of ten normal patients (I-R) with a left dominant follicle (DF).

FIG. 15A shows a T1-weighted anatomical MRI scan.

FIG. 15B shows MRI uterus segmentation.

FIG. 15C shows MRI-constructed body-uterus geometry.

FIG. 15D shows wearable electrode patches.

FIG. 15E shows a multichannel ADC box.

FIG. 15F shows filtered slow-wave electrical signals (bandwidth: 0.01-0.05 Hz).

FIG. 15G shows a detailed electrical activation sequence of one uterine peristalsis initiated at the fundal region and terminated at the cervix, red colors represent the uterine regions experiencing peristalsis waves.

FIG. 15H shows isochrone maps with gray, red, and blue representing inactive, early, and late activation regions, respectively.

FIG. 15I shows a magnitude map showing the distribution of electrical potential.

FIG. 15J shows an activation map showing the electrically activated uterine region in red.

FIG. 17A-P illustrate group level analysis of uterine peristalsis waves, where *P<0.05, P<0.01, *P<0.001, ****P<0.0001.

FIG. 17A shows frequency of peristalsis waves with TVUS and without TVUS during the menses phase.

FIG. 17B shows duration of peristalsis waves with TVUS and without TVUS during the menses phase.

FIG. 17C shows magnitude of peristalsis waves with TVUS and without TVUS during the menses phase.

FIG. 17D shows activation ratio of peristalsis waves with TVUS and without TVUS during the menses phase.

FIG. 17E shows frequency of peristalsis waves with TVUS and without TVUS during the proliferative phase.

FIG. 17F shows duration of peristalsis waves with TVUS and without TVUS during the proliferative phase.

FIG. 17G shows magnitude of peristalsis waves with TVUS and without TVUS during the proliferative phase.

FIG. 17H shows activation ratio of peristalsis waves with TVUS and without TVUS during the proliferative phase.

FIG. 17P shows activation ratio of peristalsis waves with TVUS and without TVUS during the secretory phase.

FIG. 18A shows a short anatomical MRI determining uterus-boy surface geometry.

FIG. 18B shows segmentation of body surface, uterus surface, and fallopian tubes.

FIG. 18C shows a patient-specific body-uterus geometry.

FIG. 18D shows electrode patches placed on the patient's abdomen and back to record body surface electrical signals.

FIG. 18E shows electrical signal measurements on the patient's body surface.

FIG. 18F shows filtered electrical signals (bandwidth: 0.01-0.1 Hz).

FIG. 18G shows uterine surface electrical signals from one uterine surface point around the fundal region (star in FIGS. 18I-J). Red dots denote the points of steepest negative slope to represent the activation times during peristalsis cycles.

FIG. 18H shows uterine surface electrical signals from one uterine surface point around the cervical region (cross in FIGS. 18I-J). Red dotes denote the points of steepest negative slope to represent the activation times during peristalsis cycle.

FIG. 18I shows a detailed activation sequence of one complete uterine peristalsis cycle initiated near the fundus and terminated near the cervix.

FIG. 18J shows uterine isochrone maps from the same uterine peristalsis cycle. Warm and cool colors represent early and late activation, respectively. The white arrow depicts the peristalsis propagation direction.

FIG. 18K shows one instant uterine potential map from the same uterine peristalsis cycle in FIGS. 18I and J and represents the potential distribution over the entire 3D uterine surface.

FIG. 18L shows distribution of uterine peristalsis direction (Cervix-Fundus, Fundus-Cervix, and others), initiation, and termination sites analyzed from one electrical mapping.

FIG. 19A shows a dominant Fundus-Cervix uterine peristalsis pattern during the menses phase.

FIG. 19B shows a Fundus-Cervix pattern during the proliferative phase.

FIG. 19C shows dominant Cervix-Fundus uterine peristalsis patterns during the peri-ovulatory phase.

FIG. 19D shows dominant Cervix-Fundus uterine peristalsis patterns during the secretory phase.

FIG. 19E shows pie charts showing the uterine peristalsis direction distribution in each phase.

FIG. 19F shows a bar graph of uterine peristalsis frequency in each phase.

FIG. 19G shows a boxplot of uterine peristalsis duration down sampled to 1 Hz, seconds for all peristalsis waves in each phase (each dot represents one uterine peristalsis wave).

FIG. 19H shows a boxplot of uterine peristalsis magnitude (mV) for all peristalsis waves in each phase (each dot represents one uterine peristalsis wave).

FIG. 19I shows a boxplot of uterine peristalsis power (mV*sec) for all peristalsis waves in each phase (each dot represents one uterine peristalsis wave).

FIG. 20A shows a dominant Cervix-Fundus uterine peristalsis pattern during the menses phase.

FIG. 20B shows a Cervix-Fundus uterine peristalsis pattern during the proliferative phase.

FIG. 20C shows a Fundus-Cervix uterine peristalsis pattern during the peri-ovulatory phase.

FIG. 20D shows a Fundus-Cervix uterine peristalsis pattern during the secretory phase.

FIG. 20E shows pie charts showing the uterine peristalsis direction distribution in each phase.

FIG. 20F shows a boxplot of uterine peristalsis frequency (waves/min) for each phase.

FIG. 20G shows a boxplot of uterine peristalsis duration down sampled to 1 Hz, seconds for all peristalsis waves in each phase (each dot represents one uterine peristalsis wave).

FIG. 20H shows a boxplot of uterine peristalsis magnitude (mV) for all peristalsis waves in each phase (each dot represents one uterine peristalsis wave).

FIG. 20I shows a boxplot of uterine peristalsis power (mV*sec) for all peristalsis waves in each phase (each dot represents one uterine peristalsis wave).

FIG. 21A shows overall frequency of uterine peristalsis waves over in the standardized 28-day menstrual cycle. Black dots and red dots represent the average uterine peristalsis measurements of each participant with regular menstrual cycles and endometriosis, respectively. Black curves with gray regions show the confidence regions of fitted overall frequency curves in participants with normal menstrual cycles. Red curves show the fitted overall frequency curves in participants with endometriosis.

Figures 21A, 21B:
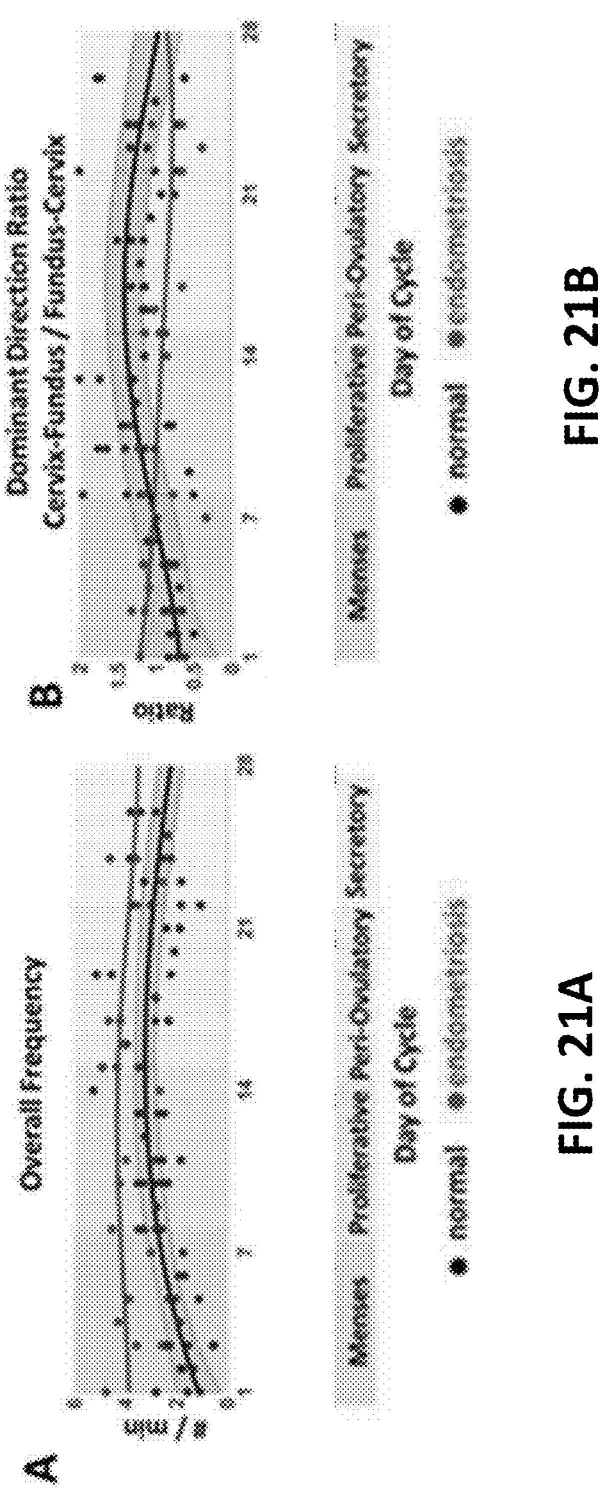
FIGS. 21A-X show a longitudinal study of uterine peristalsis in normal participants and participants with endometriosis throughout the menstrual cycle, where N=17 healthy participants with 4968 uterine peristalsis waves and 5 participants with 679 uterine peristalsis waves. *P<0.05, P<0.01, *P<0.001, ****P<0.0001.
FIG. 21B shows the dominant direction ratio Cervix-Fundus/Fundus-Cervix of uterine peristalsis waves in the standard 28-day menstrual cycle. Black dots and red dots represent the average uterine peristalsis measurements of each participant with regular menstrual cycles and endometriosis, respectively. Black curves with gray regions show the confidence regions of fitted overall dominant direction ratio Cervix-Fundus/Fundus-Cervix curves in participants with normal menstrual cycles. Red curves show the fitted dominant direction ratio Cervix-Fundus/Fundus-Cervix curves in participants with endometriosis.
Figures 21C, 21D:
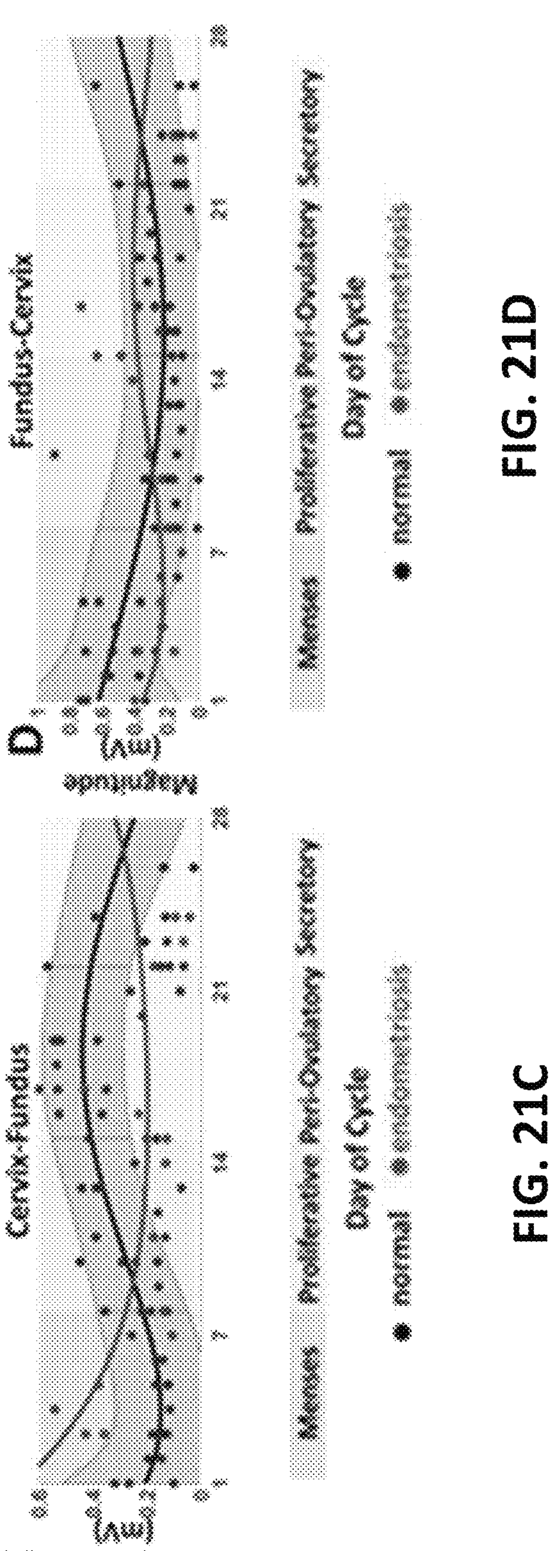
FIG. 21C shows the magnitude (mV) of peristalsis waves in the Cervix-Fundus direction in the standardized 28-day menstrual cycle. Black dots and red dots represent the average uterine peristalsis measurements of each participant with regular menstrual cycles and endometriosis, respectively. Black curves with gray regions show the confidence regions of fitted magnitude curves in participants with normal menstrual cycles. Red curves show the fitted magnitude curves in participants with endometriosis.
FIG. 21D shows the magnitude (mV) of peristalsis waves in the Fundus-Cervix direction in the standardized 28-day menstrual cycle. Black dots and red dots represent the average uterine peristalsis measurements of each participant with regular menstrual cycles and endometriosis, respectively. Black curves with gray regions show the confidence regions of fitted magnitude curves in participants with normal menstrual cycles. Red curves show the fitted magnitude curves in participants with endometriosis.
Figures 21E, 21F:
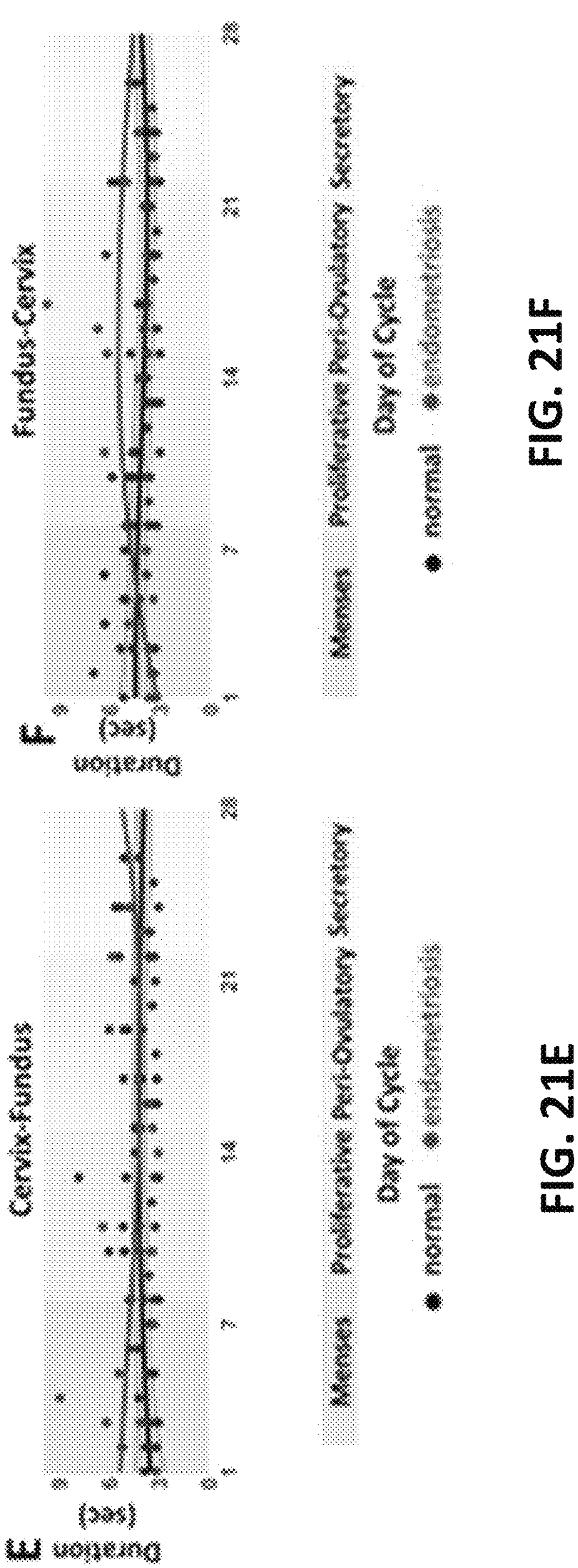
FIG. 21E shows the duration (sec) of peristalsis waves in the Cervix-Fundus direction in the standardized 28-day menstrual cycle. Black dots and red dots represent the average uterine peristalsis measurements of each participant with regular menstrual cycles and endometriosis, respectively. Black curves with gray regions show the confidence regions of fitted duration curves in participants with normal menstrual cycles. Red curves show the fitted duration curves in participants with endometriosis.

FIG. 21F shows the duration (sec) of peristalsis waves in the Fundus-Cervix direction in the standardized 28-day menstrual cycle. Black dots and red dots represent the average uterine peristalsis measurements of each participant with regular menstrual cycles and endometriosis, respectively. Black curves with gray regions show the confidence regions of fitted duration curves in participants with normal menstrual cycles. Red curves show the fitted duration curves in participants with endometriosis.

Figure 20A:
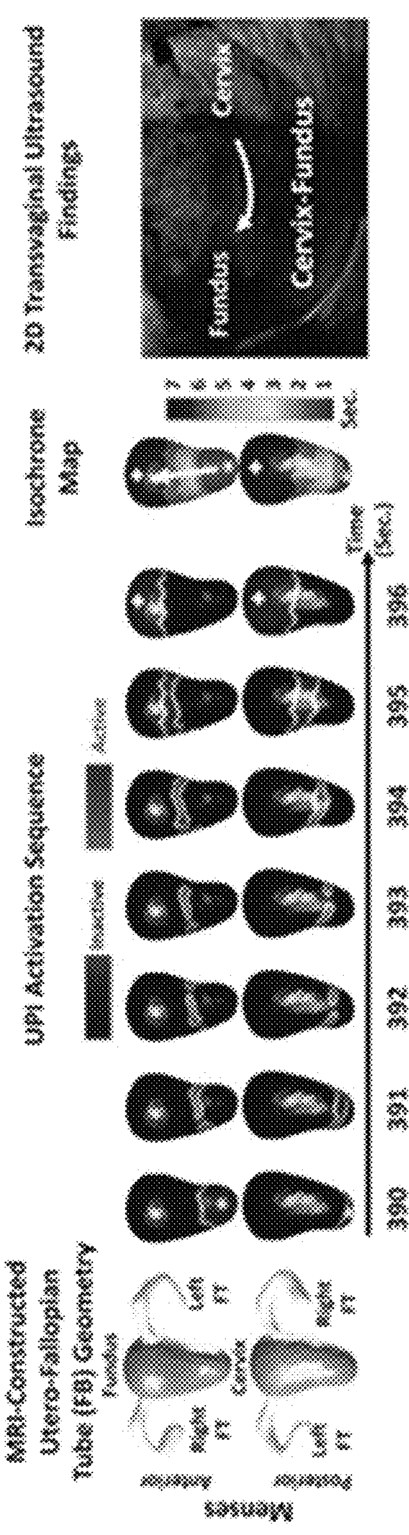
FIGS. 20A-I show uterine peristalsis imaging in one participant with surgically confirmed endometriosis during four phases of the menstrual cycle. In the UPI activation sequences and isochrone maps, the white asterisks indicate the peristalsis wave initiation sites, and the white arrows indicate the propagation directions. *P<0.05, **P<0.01.
Figure 20B:
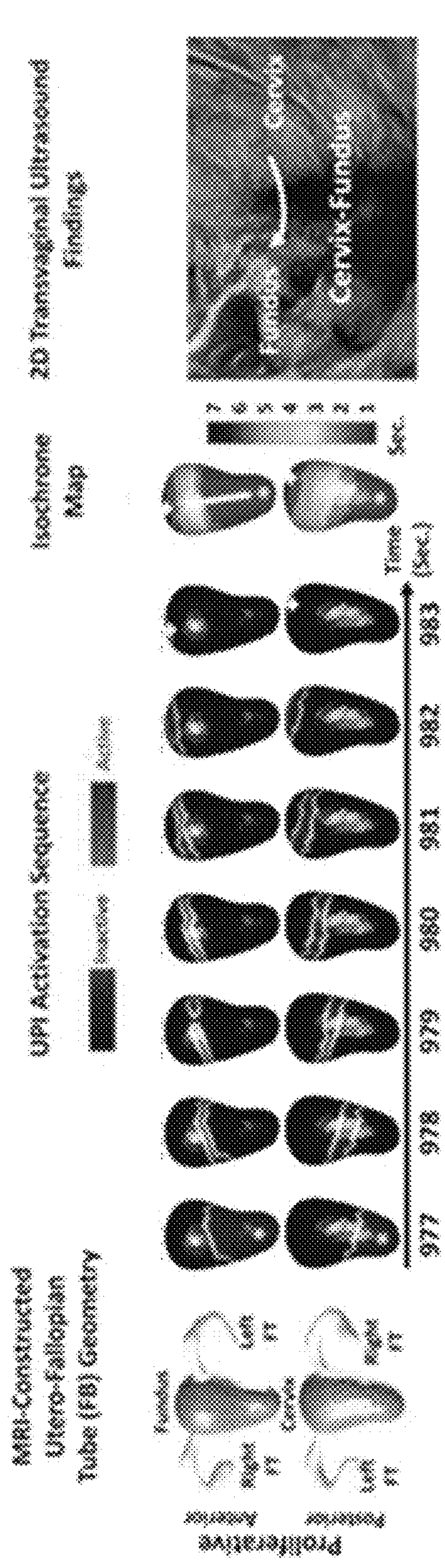
Figure 20C:
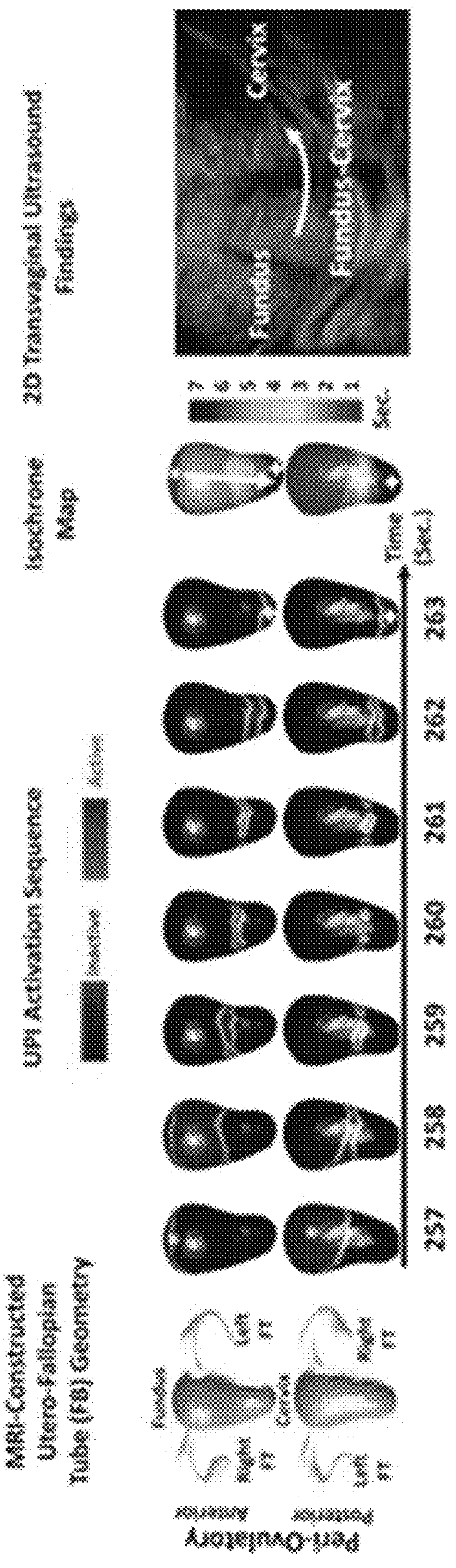
Figure 20D:
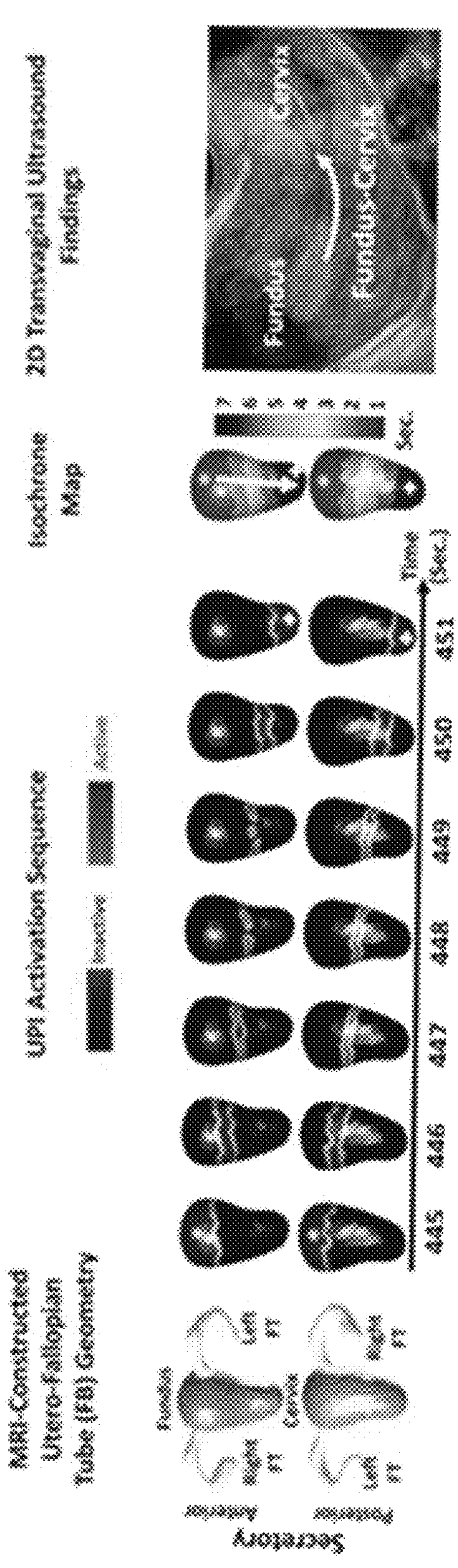
Figure 20E:
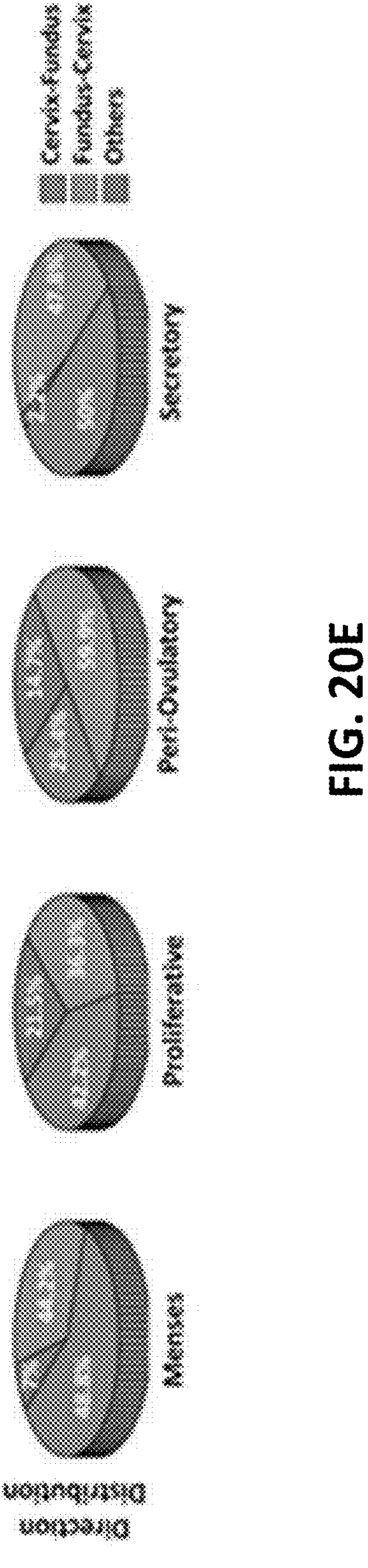
Figure 20F:
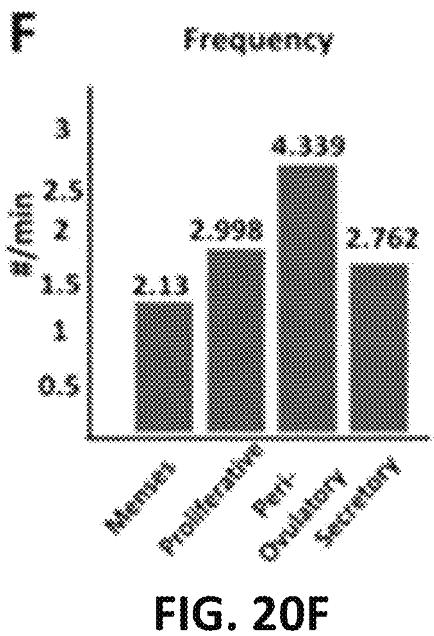
Figure 20G:
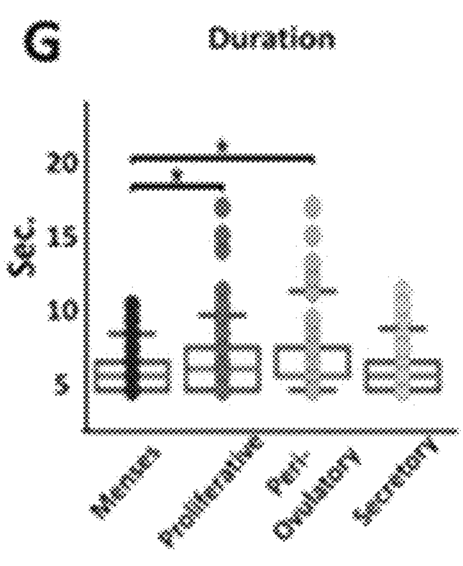
Figure 20H:
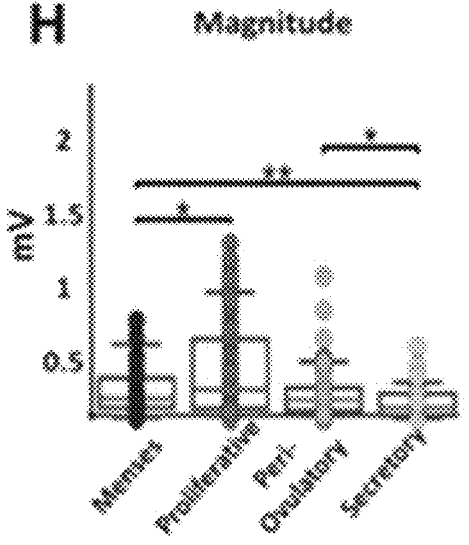
Figure 20I:
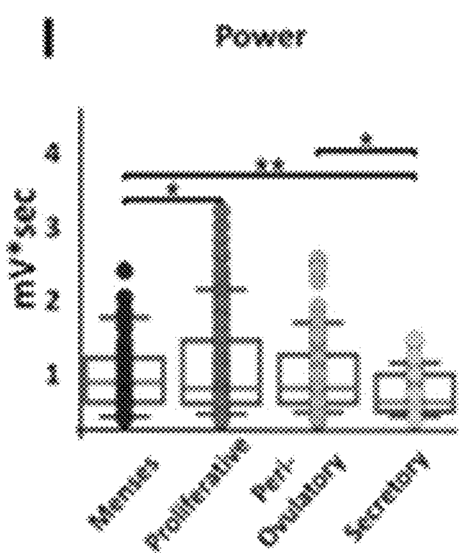

FIG. 20G shows the power (mV*sec) of peristalsis waves in the Cervix-Fundus direction in the standardized 28-day menstrual cycle. Black dots and red dots represent the average uterine peristalsis measurements of each participant with regular menstrual cycles and endometriosis, respectively. Black curves with gray regions show the confidence regions of fitted power curves in participants with normal menstrual cycles. Red curves show the fitted power curves in participants with endometriosis.

Figures 21G, 21H:
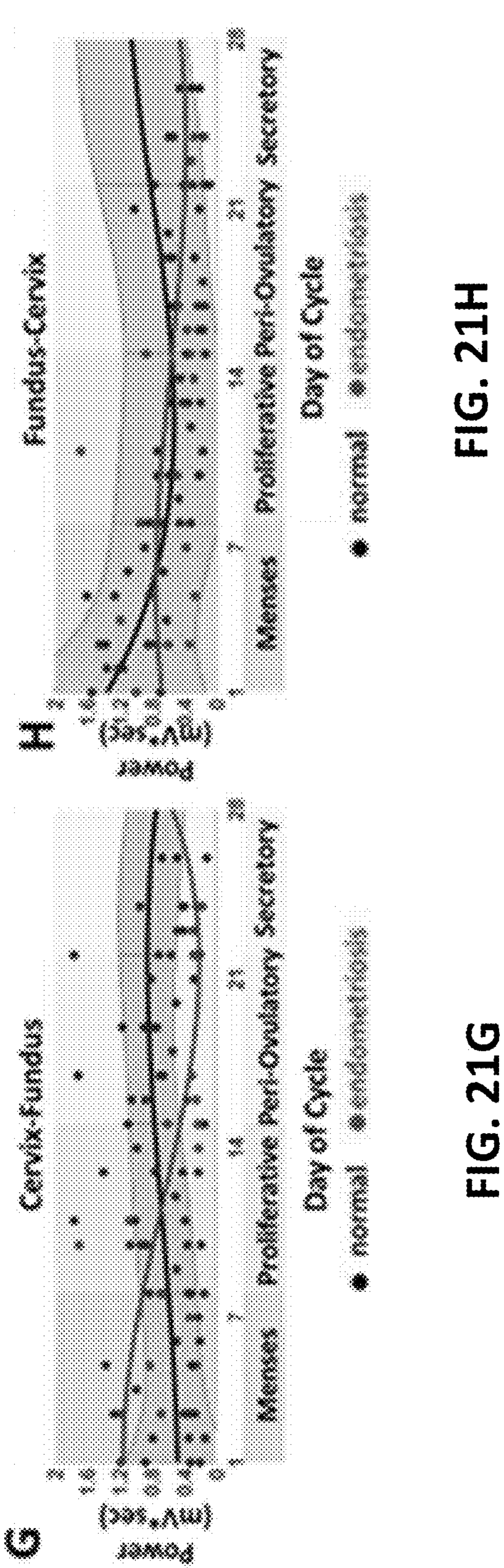

FIG. 21H shows the power (mV*sec) of peristalsis waves in the Fundus-Cervix direction in the standardized 28-day menstrual cycle. Black dots and red dots represent the average uterine peristalsis measurements of each participant with regular menstrual cycles and endometriosis, respectively. Black curves with gray regions show the confidence regions of fitted power curves in participants with normal menstrual cycles. Red curves show the fitted power curves in participants with endometriosis.

FIG. 21I shows the direction ratio of peristalsis waves in the Cervix-Fundus direction in the menses phase of healthy participants and endometriosis participants. The black/red cross shows the median values for normal and endometriosis participants, respectively.

FIG. 21J shows the direction ratio of peristalsis waves in the Fundus-Cervix direction in the menses phase of healthy participants and endometriosis participants. The black/red cross shows the median values for normal and endometriosis participants, respectively.

FIG. 21K shows the direction ratio of peristalsis waves in the Cervix-Fundus direction in the peri-ovulatory phase of healthy participants and endometriosis participants. The black/red cross shows the median values for normal and endometriosis patients, respectively.

FIG. 21L shows the direction ratio of peristalsis waves in the Fundus-Cervix direction in the peri-ovulatory phase of healthy participants and endometriosis participants. The black/red cross shows the median values for normal and endometriosis patients, respectively.

FIG. 21M shows the magnitude (mV) of peristalsis waves in the Cervix-Fundus direction in the menses phase of healthy participants and endometriosis participants. The black/red cross shows the median values for normal and endometriosis participants, respectively.

FIG. 21N shows the magnitude (mV) of peristalsis waves in the Fundus-Cervix direction in the menses phase of healthy participants and endometriosis participants. The black/red cross shows the median values for normal and endometriosis participants, respectively.

FIG. 21O shows the magnitude (mV) of peristalsis waves in the Cervix-Fundus direction in the peri-ovulatory phase of healthy participants and endometriosis participants. The black/red cross shows the median values for normal and endometriosis patients, respectively.

FIG. 21P shows the magnitude (mV) of peristalsis waves in the Fundus-Cervix direction in the peri-ovulatory phase of healthy participants and endometriosis participants. The black/red cross shows the median values for normal and endometriosis patients, respectively.

Figures 21Q, 21R, 21S, 21T:
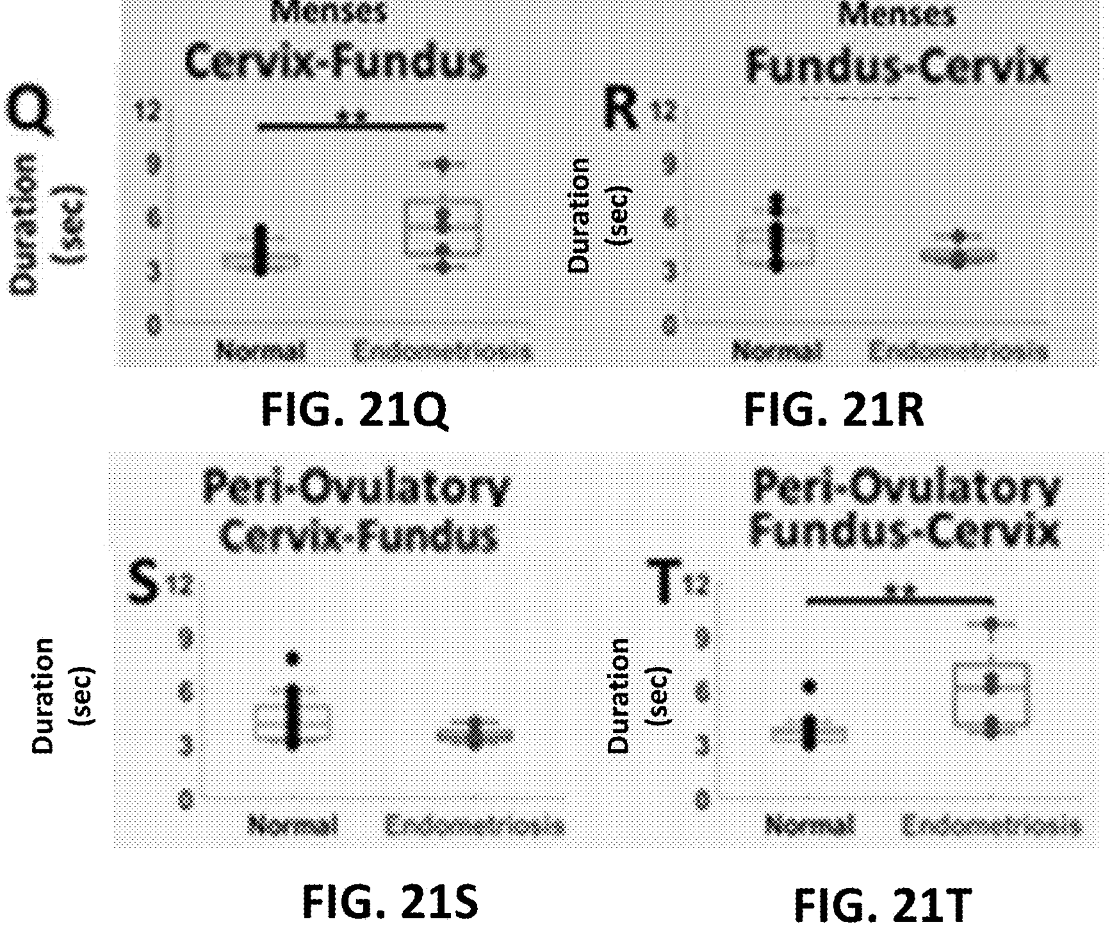

FIG. 21Q shows the duration (sec) of peristalsis waves in the Cervix-Fundus direction in the menses phase of healthy participants and endometriosis participants. The black/red cross shows the median values for normal and endometriosis participants, respectively.

FIG. 21R shows the duration (sec) of peristalsis waves in the Fundus-Cervix direction in the menses phase of healthy participants and endometriosis participants. The black/red cross shows the median values for normal and endometriosis participants, respectively.

FIG. 21S shows the duration (sec) of peristalsis waves in the Cervix-Fundus direction in the peri-ovulatory phase of healthy participants and endometriosis participants. The black/red cross shows the median values for normal and endometriosis patients, respectively.

FIG. 21T shows the duration (sec) of peristalsis waves in the Fundus-Cervix direction in the peri-ovulatory phase of healthy participants and endometriosis participants. The black/red cross shows the median values for normal and endometriosis patients, respectively.

FIG. 21U shows the power (mV*see) of peristalsis waves in the Cervix-Fundus direction in the menses phase of healthy participants and endometriosis participants. The black/red cross shows the median values for normal and endometriosis participants, respectively.

FIG. 21V shows the power (mV*see) of peristalsis waves in the Fundus-Cervix direction in the menses phase of healthy participants and endometriosis participants. The black/red cross shows the median values for normal and endometriosis participants, respectively.

FIG. 21W shows the power (mV*sec) of peristalsis waves in the Cervix-Fundus direction in the peri-ovulatory phase of healthy participants and endometriosis participants. The black/red cross shows the median values for normal and endometriosis patients, respectively.

FIG. 21X shows the power (mV*sec) of peristalsis waves in the Fundus-Cervix direction in the peri-ovulatory phase of healthy participants and endometriosis participants. The black/red cross shows the median values for normal and endometriosis patients, respectively.

Figure 22A:
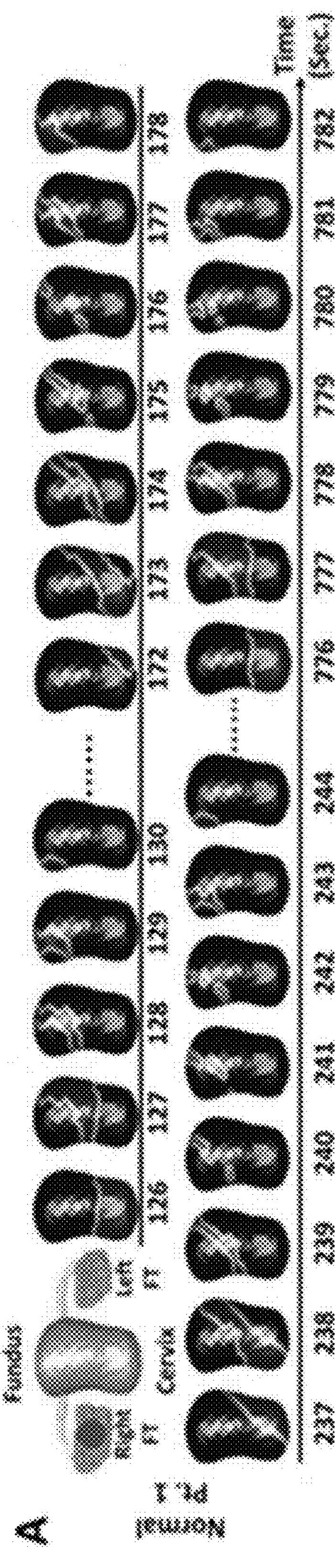
Figure 22B:
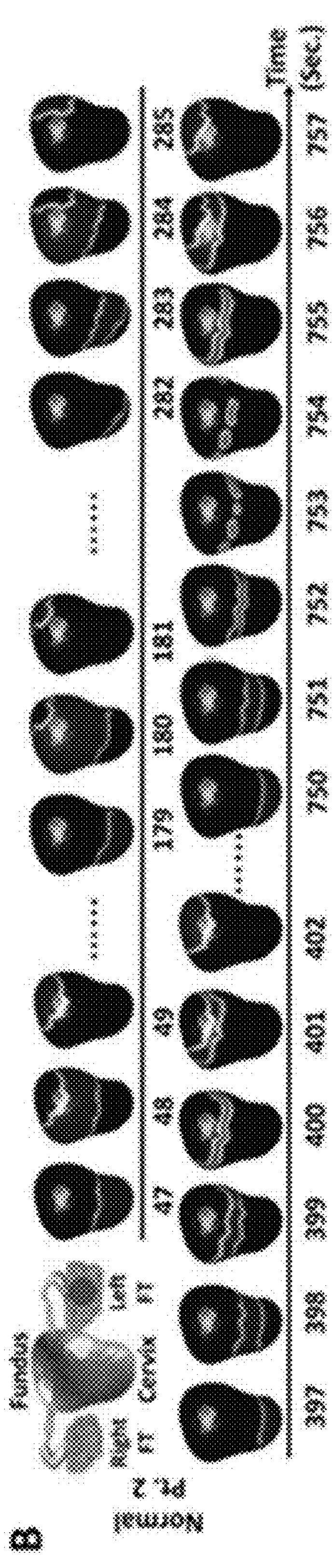
Figure 22C:
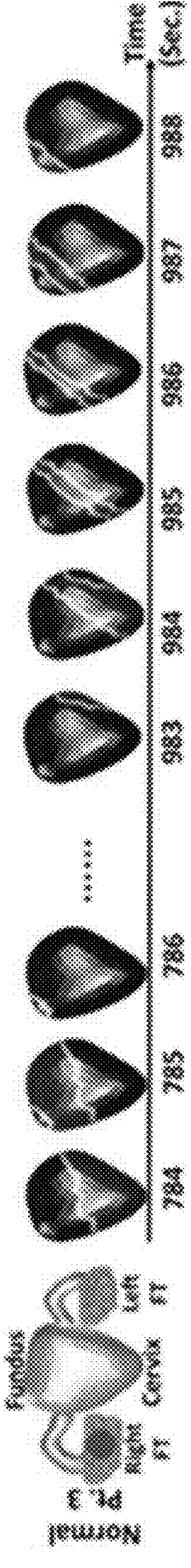
Figure 22D:
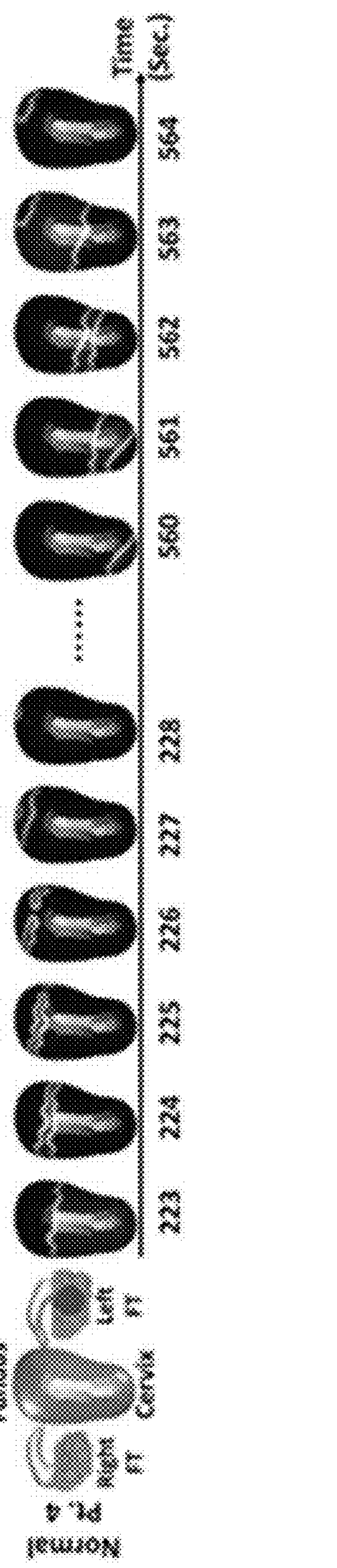
Figure 22E:
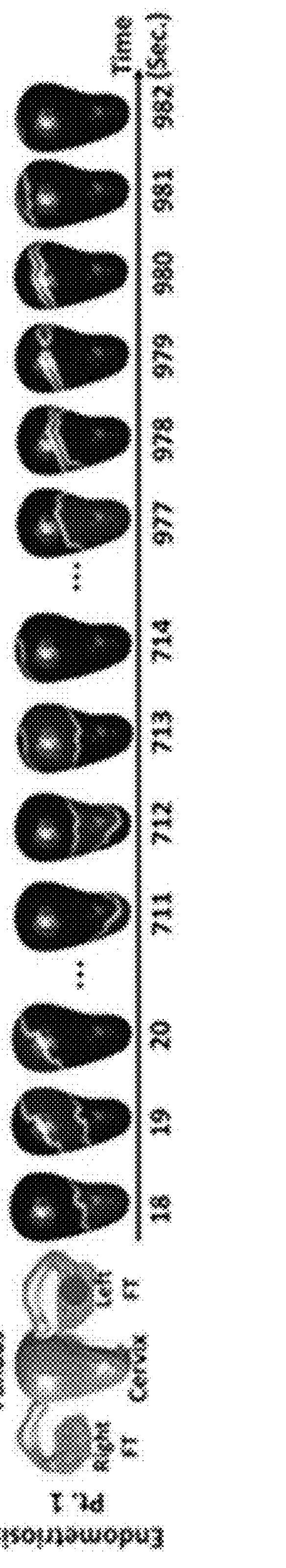
Figure 22F:
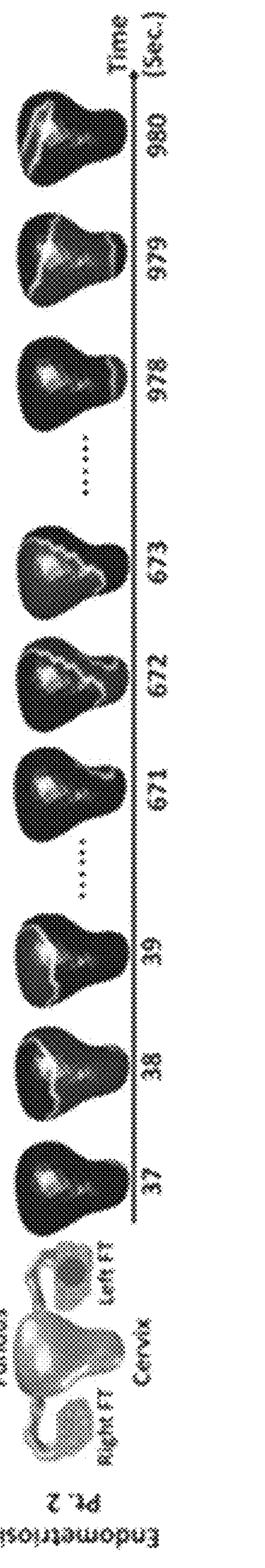

FIGS. 22A-F show representative asymmetric uterine paralysis patterns in healthy participants with the normal menstrual cycle (FIGS. 22A-D) and endometriosis patients (FIGS. 21E-F) during the ovulatory phase. In each panel, anatomical uterus geometry with fallopian tubes was segments from the T1-weighted and T2-weighted MRI images. Red dots indicate the ovary with the dominant follicle. FIG. 22A and FIG. 22C show normal patients 1 and 3 have left-dominant follicles and left-sided asymmetric uterine peristalsis propagation. FIG. 22B and FIG. 22D show normal participants 2 and 4 have right-dominant follicles and right-sided asymmetric uterine peristalsis propagation. FIG. 22E and FIG. 22F show endometriosis patients with left dominant follicles and right-sided asymmetric uterine peristalsis. Patient numbers correspond with Table 6 below.

DETAILED DESCRIPTION

Success of fertility treatment generally remains at about 30% per cycle. In a substantial number of these patients, no underlying reason for failure can be found, and hence no causal treatment is available. In fertility treatment, the least controlled phase of the treatment is the period between embryo transfer and pregnancy testing. In this phase, UP plays its part in nidation. Knowledge of UP may provide an insight into a patient's fertility status and improve treatment success rate. Uterine peristalsis imagining (UPI) techniques provides a low-cost solution to image the three-dimension (3D) UP pattern in humans and use the imaging findings to support a patient's diagnosis and treatment as disclosed herein.

Electromyometrial imaging (EMMI) may be utilized to define the myometrial electrical activity quantitatively and objectively in a non-invasive manner. The EMMI system combines an MRI scan to determine body-uterus geometry and body surface electrodes to determine body surface potential placed into a software system to provide reconstructed uterine surface potentials. MRIs have been utilized to determine patient's uterus-body surface geometry. The reconstructed uterine surface potentials quantitatively image and measure 3D electrophysiological activities of uterine contractions non-invasively.

The EMMI system incorporates MRI imaging of the patient-specific uterus and surface electrodes (e.g., 128 body surface electrodes) to non-invasively measure uterine contractions. The patients have four visits, one at each phase of her menstrual cycle with an MRI occurring at her first visit. During each visit, electrodes are applied to the abdomen while simultaneously having a transvaginal ultrasound (e.g., 15-minute transvaginal ultrasound) to video direction of uterine peristalsis. The ultrasound is an independent entity to EMMI to validate the system. The EMMI system demonstrates uterine peristalsis waves in 3D.

UPI can provide objective, quantitative measures of uterine peristalsis. Unlike other modalities such as TVUS, HSSG, and IUPC, the contractile activity seen during UP may be quantitatively measured and reliably observed with UPI. With 3D accuracy, which takes into consideration the individual's unique uterine anatomy, the site of initiation and termination of the contraction are mapped along with the characterization of the direction, duration, and magnitude of the contractile forces. Novel peristalsis indices were developed for quantitative characterization of uterine contractile patterns, as discussed herein. This includes measuring the duration and magnitude of UP. This assessment can be performed in a noninvasive way with little patient discomfort for a prolonged period.

In the patients with regular cycles, menses and peri-ovulatory phases may have predominant peristalsis patterns, fundus-cervix and cervix-fundus, respectively, while the proliferative and secretory phases may have a more balanced pattern. Prior ultrasound studies have demonstrated that free fluid occurs in reproductive age women at all phases of the menstrual cycle, most significantly during menses. These findings are consistent with the study herein because each phase has cervix-fundus contractions likely contributing to free fluid, however, during menses, the dominant F-C pattern has been previously postulated to facilitate expulsion of blood and endometrial tissue while protecting against ascending pathogens. The dominant peristalsis pattern at the peri-ovulatory phase is from fundus to cervix which functions to facilitate active sperm transport promoting oocyte/sperm interaction. This has been previously studied using serial HSSGs to follow labelled macropheres the size of sperm which were transported from the cervix into the uterus and fallopian tubes. The secretory phase has the most balanced contraction types because a more quiescent environment is needed to promote embryo implantation.

Although it is well-known that all reproductive-age women have some amount of retrograde menstruation, especially during menses, the increased C-F contractions demonstrate increased retrograde menstruation compared to normal controls. This may contribute to Sampson's theory for the cause of endometriosis due to increased amount of retrograde flow of endometrial cells. Patients with endometriosis with decreased duration and increased magnitude were seen demonstrating abnormal contractions (dysperistalsis). This has previously been demonstrated using invasive uterine imaging modalities. Dysperistalsis is also theorized to contribute to endometriosis because it does not promote as efficient emptying of the uterus during menses and those cells may accumulate in the uterus and move retrograde through the fallopian tubes during other phases of the menstrual cycle. Rapid contractions (hyperperistalsis), seen with decreased duration of contractions and increased frequency, may also facilitate detachment of utopic endometrial cells from the uterus and into the fallopian tubes which may also promote endometriosis.

Firstly, the UPI system/method is noninvasive, which is optimal modality for long-time uterine monitor and patient comfort. Secondly, it provides high spatial-temporal resolution information including the initiation sites, peristalsis directions and strengths, which may help gynecologists monitor and diagnose patients' uteri more accurately. Thirdly, different from two-dimensional (2D) TVUS technology, the UPI system/method is three-dimensional and may detect peristalsis generated from all directions. Fourthly, quantification of peristalses strength using the UPI software may be automatic, objective, and real-time.

The UPI system may be used to establish reference ranges for the indices of uterine peristalsis in normal menstrual cycles. These normal reference ranges may be used to identify patients with abnormal gynecological conditions such as endometriosis, ovulatory dysfunction, uterine anomalies, and abnormal uterine bleeding. Moreover, with the detailed 4D electrical activation patterns imaged by the UPI system, it is possible to longitudinally evaluate the effects of various clinical interventions and optimize treatment plans for individual patients. The UPI system may facilitate development of nonpharmaceutical strategies to correct abnormal uterine peristalsis underlying gynecological conditions, such as endometriosis, in a similar manner as cardiac pacemakers are not used to treat heart conditions.

Methods

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, condition, or other word that substantially modifies, such that the component or condition need not be exact. The terms "comprising," "including" and "having" are used interchangeably in this disclosure. The terms "comprising," "including" and "having" mean to include, but not necessarily be limited to the things so described.

The methods and systems described herein are constructed to overcome the major disadvantages involved in monitoring uterine peristalsis and overcomes some of the issues with the current state of the art. The methods and systems herein may have improved safety, accuracy, robustness, and feasibility for evaluation of uterine contractility as compared to the current state of the art.

Figure 1A:
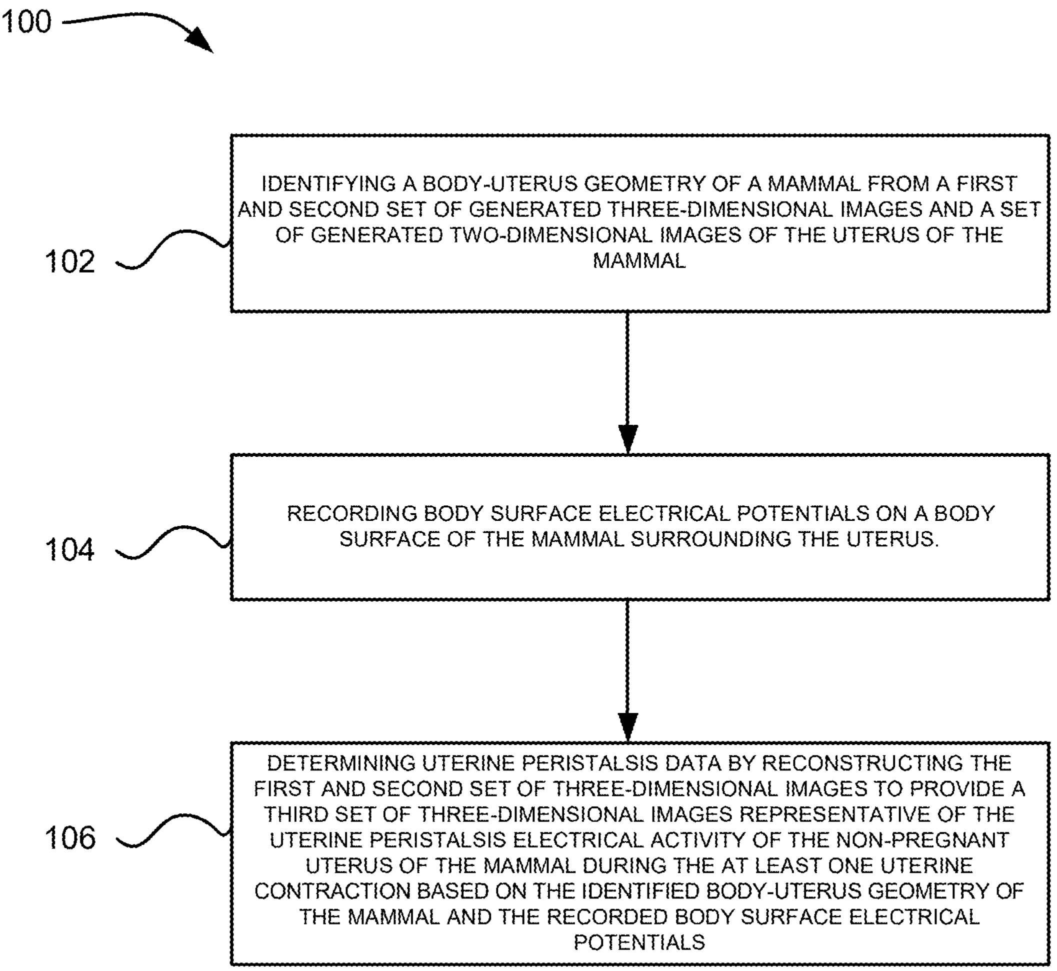
FIG. 1A is a flow diagram of an example method for noninvasive three-dimensional imaging of uterine electrophysiology, also referred to as uterine peristalsis imaging (UPI).
Figure 1B:
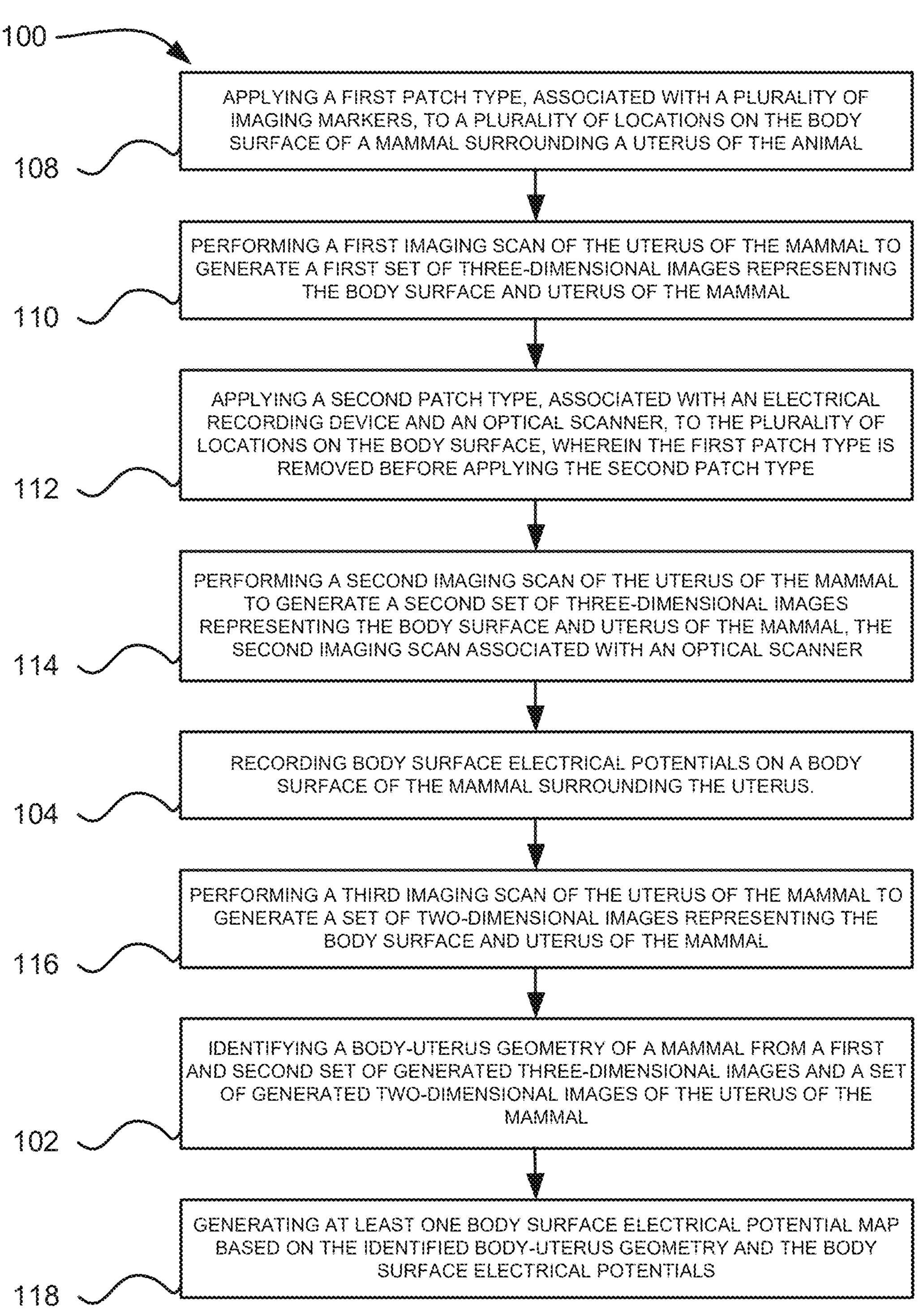
FIG. 1B is a flow diagram showing additional details of the method of FIG. 1A.

A description of a method for monitoring uterine peristalsis (e.g., uterine surface electrical activity of a uterus of a mammal) also referred to as uterine peristalsis imaging (UPI), as illustrated in FIGS. 1A and 1B, is first disclosed herein.

The method shown in FIG. 1A is provided by way of example, as there are a variety of ways to carry out the method. Additionally, while the example method is illustrated with a particular order of steps, those of ordinary skill in the art will appreciate that FIG. 1A and the steps shown therein can be executed in any order that accomplishes the technical advantages of the present disclosure and can include fewer or more steps than illustrated. Each step shown in FIG. 1A represents one or more processes, methods or subroutines, carried out in the example method.

Figure 9A:
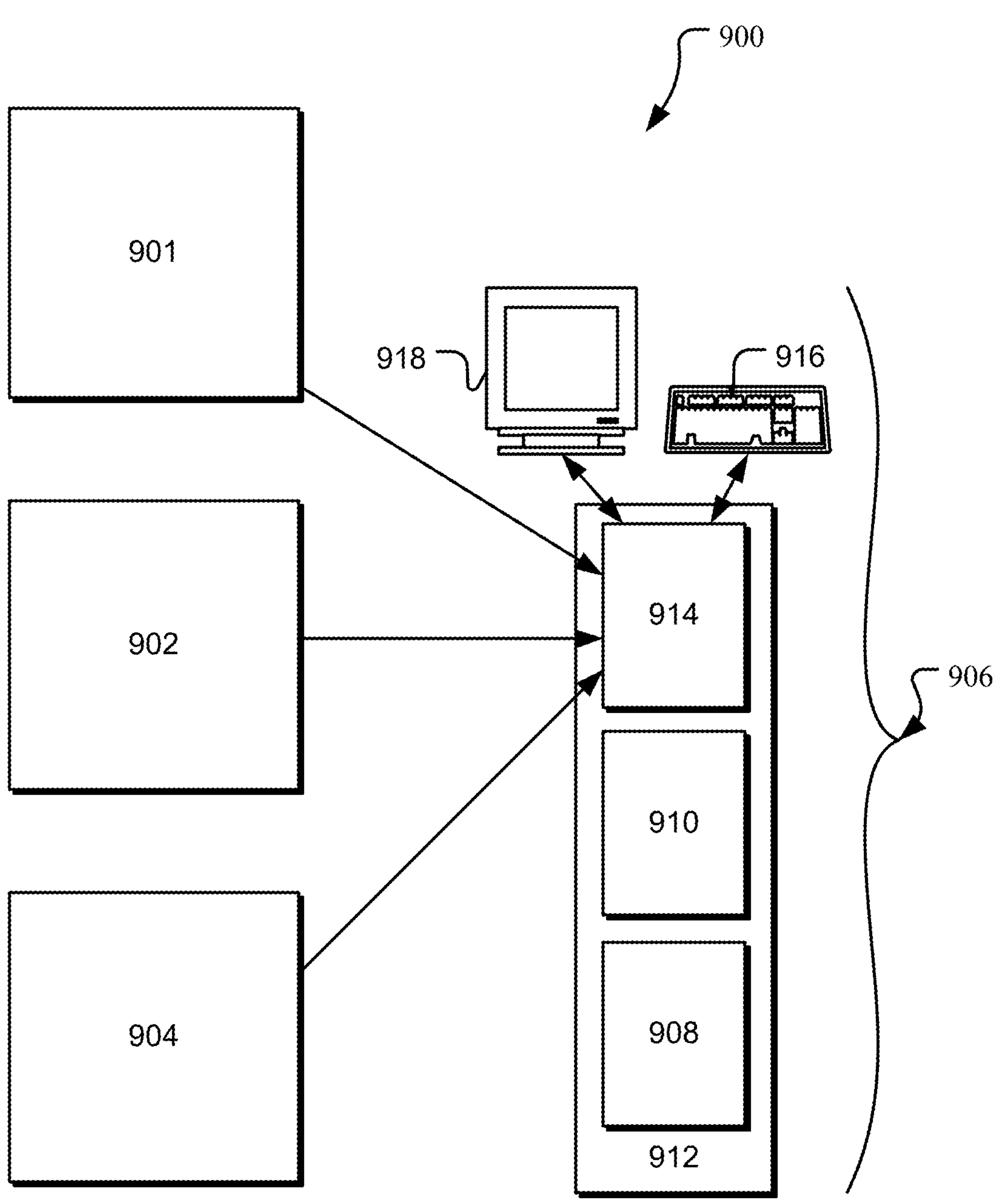
FIG. 9A shows an example system for noninvasively determining uterine electrical activity of a mammal.
Figure 9B:
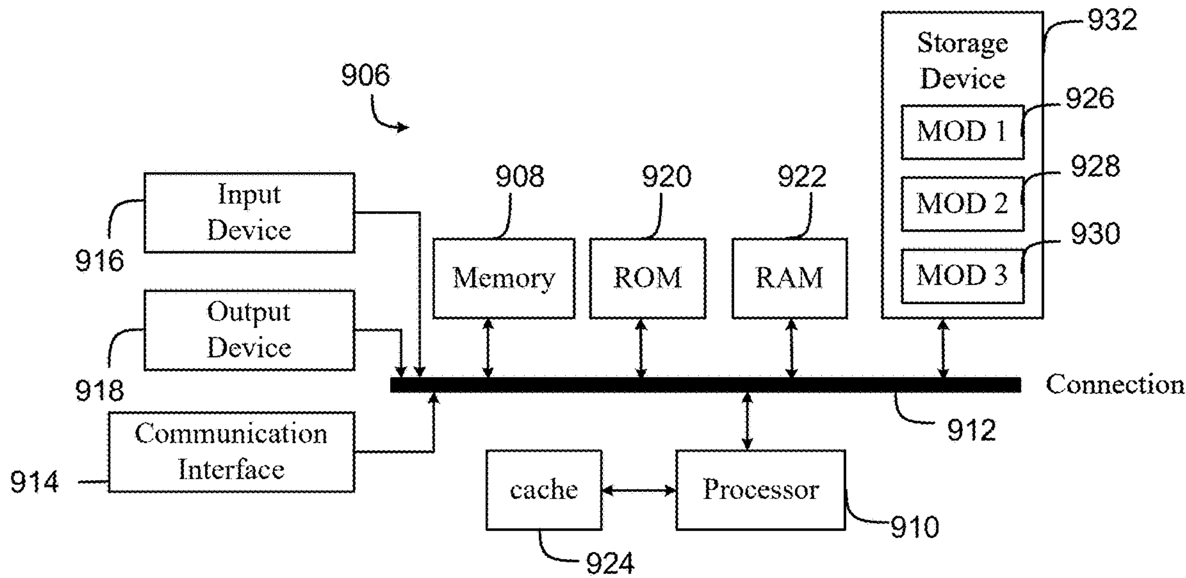
FIG. 9B shows an example computing system of the system of FIG. 9A.

FIG. 1A shows a flow diagram of an example method 100 for monitoring uterine peristalsis of a uterus of a mammal. Non-limiting examples of the mammal include humans, mice, sheep, cats, and dogs. One or more steps of the method may be performed using at least one of the components of system 900, as seen in FIGS. 9A-9B.

The method 100 can begin at step 102. In method 100, step 102 may include identifying a body-uterus geometry of the mammal from one or more sets of generated three-dimensional images and generated two-dimensional images of the uterus of the mammal. In one example, the three-dimensional data may be verified by a set of two-dimensional images. In some examples, the body-uterus geometry may be generated by an anatomical MRI, a 3D ultrasound measurement, or other imaging systems and techniques known in the art. In some examples, 2D and 3D clinical ultrasound systems may be used to generate 3D uterine geometry. Step 104 may include detecting and recording a body surface electrical potentials on a body surface of the mammal surrounding the uterus. Step 106 may include determining uterine peristalsis data by reconstructing the sets of generated three-dimensional images based on the body-uterus geometry of the mammal and the body surface electrical potentials.

FIG. 1B illustrates additional details of the method 100. Method 100 may further include steps 108 and 118. The sets of generated three-dimensional images of the uterus of the mammal that were used to identify the body-uterus geometry in step 102 may be generated via steps 108 and 118.

At step 108, a first patch type (e.g., containing about 128 imaging markers) associated with a plurality of imaging markers (e.g., MRI-compatible fiducial markers) may be applied to a plurality of locations on a body surface of the mammal, wherein the body surface surrounds the uterus. The body surface surrounding the uterus may include an abdomen and a lower back of the mammal. In some examples, up to 8 locations may include the first patch type. In some examples, the plurality of imaging markers includes a plurality of MRI markers. The number of MRI markers may depend on the application and/or feasibility for each patient. In various examples, the plurality of MRI markers may include up to 32, up to 50, up to 64, up to 100, up to 150, up to 200, up to 250, or up to 300 MRI markers. In other examples, the plurality of MRI markers may include at least 32, at least 50, at least 64, at least 100, at least 150, at least 200, at least 250, or at least 300 MRI markers. In at least one example, the plurality of MRI markers includes up to about 256 MRI markers.

At step 110, an imaging scan of the uterus of the mammal is performed. The imaging scan is operable to provide a set of generated three-dimensional images of the uterus of the mammal. The imaging scan may be any scan performed using an imaging modality that is reasonably safe for imaging a uterus and body surface geometry of a pregnant mammal. Non-limiting examples of imaging scans include MRI scans, optical scanner scans, or ultrasound. In some examples, the imaging scan is an MRI scan, and the set of generated three-dimensional images includes MRI images. In some examples, at least a portion of the plurality of imaging markers are visible on at least a portion of the set of generated three-dimensional images. In such examples, each of the plurality of imaging markers indicate the position of one of the plurality of locations on the body surface.

In some examples, identifying the body-uterus geometry at step 102 may be performed using at least one of the components of system 900, as seen in FIG. 9A. In some examples, step 102 may include receiving the set of generated three-dimensional images at a processor, such as processor 810, wherein the processor is operable to segment the plurality of generated three-dimensional images to generate the body-uterus geometry in response to instructions from a non-transitory computer readable medium. In some examples the processor is in connection with the imaging modality that generated the set of generated three-dimensional images. In such examples, at least one processor may be operable to determine a body-uterus geometry of the mammal based on the plurality of imaging markers applied to the body surface surrounding the uterus of the mammal. The body-uterus geometry of the mammal is specific to the individual mammal. In at least one example, the instructions from the non-transitory computer readable medium are instructions encoded in UPI software.

At step 104, the electrical potentials on the body surface (also referred to as the body surface electrical activity and/or the plurality of electrical signals) are recorded via the electrical recording device (also referred to as the electrical mapping device) during at least one uterine contraction. The electrical mapping device is operable to record the body surface electrical potentials.

Method 100 may include step 112. The body surface electrical potentials referenced in step 104 may be detected via step 112. At step 112, each one of the first patch type associated with imaging markers is replaced with one of a second patch type associated with electrodes. Thus, each one of the electrodes is applied to one of the plurality of locations on the body surface surrounding the uterus of the mammal. Each one of the plurality of electrodes may be operable to detect a plurality of electrical signals on the body surface surrounding the uterus of the mammal, at the plurality of locations. In some examples, the electrodes include unipolar active electrodes. In some examples, the electrodes are in connection with an electrical mapping device. In some examples, the electrical mapping device is operable to record the body surface electrical potentials at the plurality of locations via a plurality of electrodes. In some examples, the number of electrodes is equal to the number of the plurality of MRI markers. The number of electrodes may depend on the application and/or feasibility for each patient. In various examples, the number of electrodes may include up to 32, up to 50, up to 64, up to 100, up to 150, up to 200, up to 250, or up to 300 electrodes. In at least one example, the plurality of electrodes includes up to about 256 electrodes.

At step 114, a second imaging scan of the uterus of the mammal is performed. The imaging scan is operable to provide a set of generated three-dimensional images of the uterus of the mammal. The imaging scan may be any scan performed using an imaging modality that is reasonably safe for imaging a uterus and body surface geometry of a pregnant mammal. In some examples, the second imaging scan is a 3D hand-held optical scanner scan, and the second set of generated three-dimensional images includes optical scanner images. In some examples, the surface electrodes associated with the electrical mapping device may be used in the 3D hand-held optical scan to acquire the 3D body surface.

At step 116, a third imaging scan of the uterus of the mammal is performed. The third imaging scan is operable to provide a set of generated two-dimensional images, such as from an ultrasound imaging device. In some examples the set of two-dimensional images is a continuous set of images which, when strung together consecutively, form a movie or video (also referred to as clips) of the two-dimensional images. In some examples, the third imaging scan of the uterus of the mammal is a transvaginal ultrasound (TVUS). In this example, a sonographer may hold the transducer probe while the scan is being performed on the mammal. The mammal may be lying in a semi-fowler's position during the scan. In various possible examples, the clips may range from 10 to 30 seconds in duration. In one example the duration is 20 seconds. In some examples 20 to 50 clips may be acquired during the third imaging scan. In one example 30-35 clips were acquired during the scan. Although specific time ranges and number of clips are identified, any suitable duration and number of clips may be utilized when performing various steps of the methods in various possible examples. The clips may be inspected by the sonographer independently and compared with the uterine peristalsis data for validation purposes.

In some examples, the first type of patch and/or the second type of patch may be releasably secured to a wearable device. The wearable device may include a non-reactive material capable of being worn by a mammal. The wearable device may be made of a flexible material and may be constructed with fasteners to attach the wearable device to the mammal. In one example, the wearable device is one piece of material that is pulled on or slid over the body surface of the mammal.

In some examples, determining the uterine peristalsis data at step 106 may include reconstructing the sets of generated three-dimensional images to generate at least one reconstructed three-dimensional uterine surface electrical potential map based on the body-uterus geometry of the mammal and the body surface electrical potentials, as seen in step 118.

Thus, the presently disclosed technology allows determination of the instant electrical potential and electrical activation patterns of the uterus (i.e., uterine peristalsis electrical activity data), via noninvasively obtained data, by combining the detailed body surface electrical activity (i.e., the body surface electrical potentials) with the body-uterus geometry derived from the sets of three-dimensional images. This allows the generation and comprehensive evaluation of three-dimensional uterine electrical activation patterns at high spatial and temporal resolution. The plurality of uterine surface electrical potentials represents electrical potential distribution over the entire uterine surface during an observation window. This is particularly advantageous because it allows noninvasive monitoring of initiation and propagation of uterine peristalsis by tracking electrical signals across the entire uterine surface.

In some examples, determining the uterine peristalsis data at step 106 may include reconstructing a set of electrograms based on the body-uterus geometry of the mammal and the plurality of body surface electrical potential maps. In such examples, the set of electrograms may be generated by assembling a time series of potential values at a given uterine site from the potential maps. The set of uterine surface electrical potential maps display electrical potential distribution over the entire uterine surface at a given time point. The set of electrograms may also provide temporal features of electrical activity at local sites on the uterine surface. In some examples, reconstructing set of electrograms may include using the method of fundamental solutions (MFS) to solve the three-dimensional Cauchy problem to compute the electrograms on the three-dimensional uterine surface.

In some examples, determining the uterine peristalsis data at step 106 may include reconstructing a set of isochrones maps based on the body-uterus geometry of the mammal and the plurality of body surface electrical potential maps. In such examples wherein the uterine electrical activity is determined by generating a plurality of isochrones maps, the plurality of isochrones maps may be generated by assembling local activation time of each uterine surface site during an observation window. In such examples, the observation window may be the time period of the at least one uterine contraction, e.g., the observation window may start at a time point when uterine electrical activity started to occur on a previously resting uterus, and the observation window may end at the time point when the uterus returned to electrical quiescence.

In some examples, determining the uterine peristalsis data at step 106 includes generating a set of uterine surface electrical potential maps, a set of electrograms, and/or a set of isochrone maps.

In some examples, determining the uterine surface electrical data at step 106 and step 116 may be performed using at least one of the components of system 900, as seen in FIG. 9A. In some examples, step 106 may include deriving the uterus surface geometry from the body-uterus geometry, deriving the uterine surface electrical activity from the body surface electrical activity, and mapping the uterine surface electrical activity onto the uterus geometry, using at least one of the components of system 900, such as processor 910. In such examples, the processor 910 may be operable to perform step 104 in response to instructions from a non-transitory computer readable medium, such as software memory 908. In at least one example, the instructions from the non-transitory computer readable medium are instructions encoded in the UPI software.

Figure 2A:
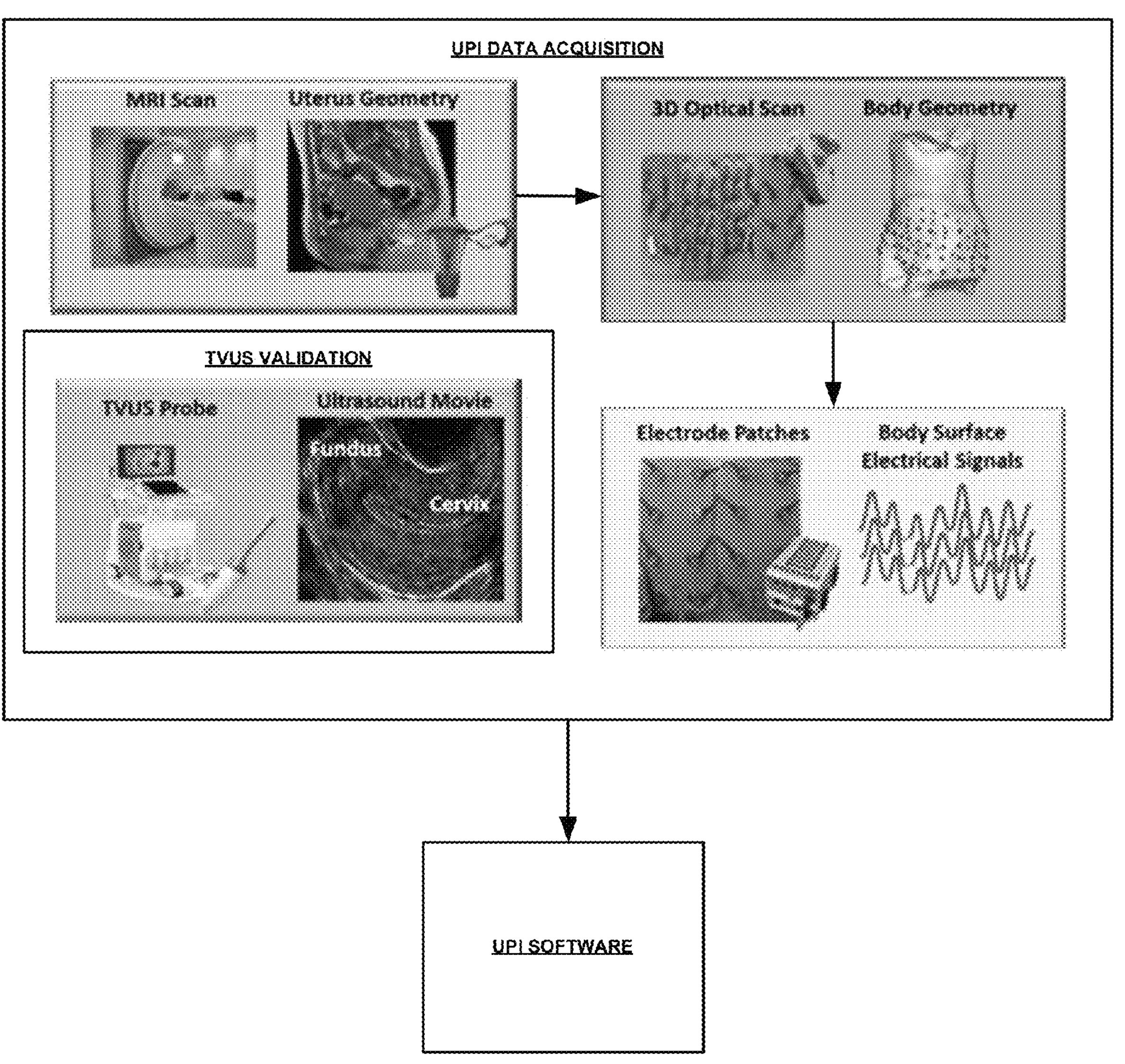
FIG. 2A-C shows various steps of performing UPI in non-pregnant women.
Figure 2B:
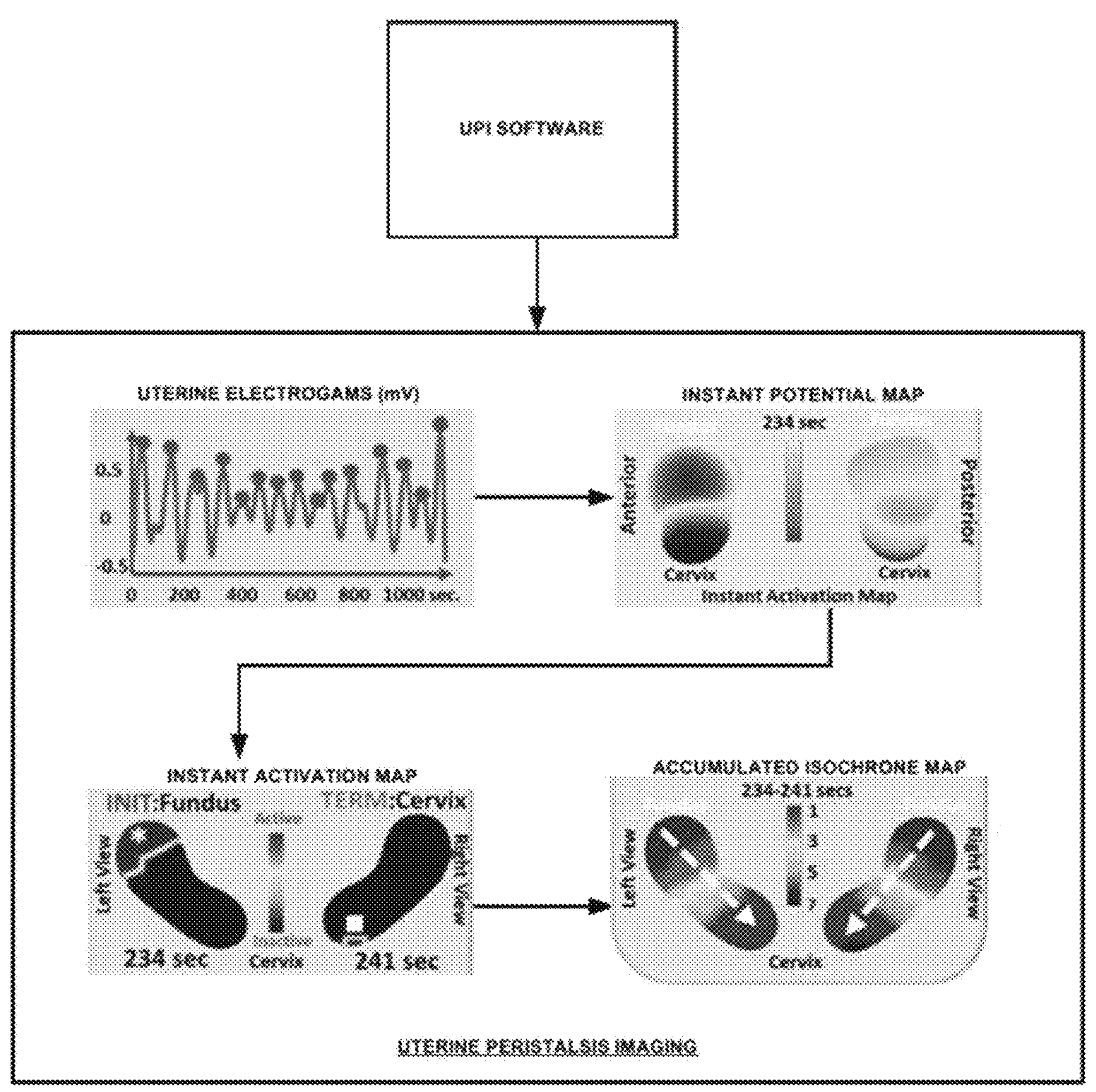
Figure 2C:
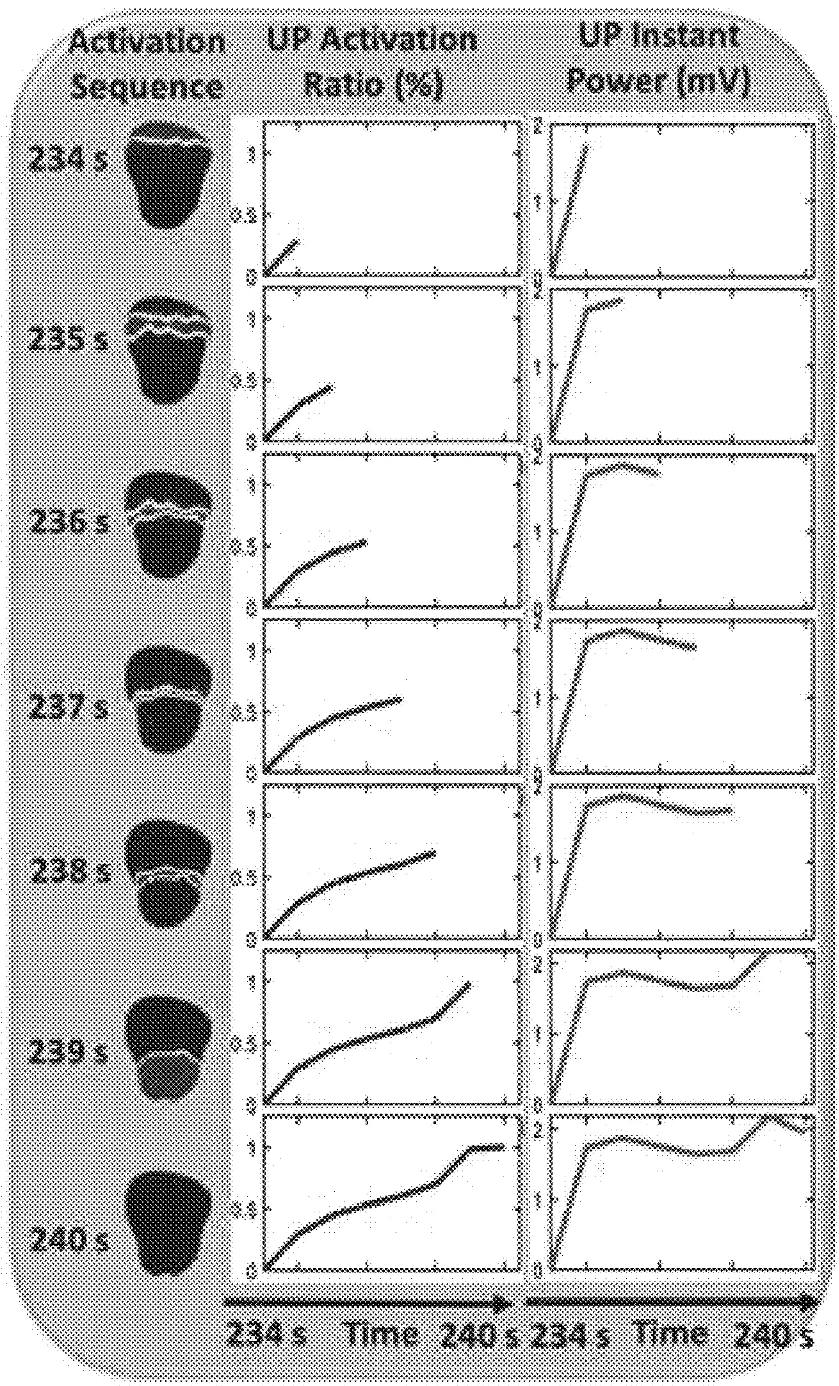

FIGS. 2A-C illustrate a study performed to assess the accuracy of UPI, wherein UPI-reconstructed uterine peristalsis surface potentials, reconstructed via the methods disclosed herein, were qualitatively and quantitatively compared to the measured peristalsis, measured via TVUS.

FIG. 2A depict various systems and methods consistent with this disclosure that were used to assess the accuracy of UPI. The following systems and methods were utilized during the study to acquire UPI data. An MRI scan was used to determine uterus-body surface geometry. The MRI scan was used to identify the uterine geometry. A hand-held 3D optical scanner was used for mapping body geometry. Electrode patches placed on a patient's abdomen and back were used to record body surface electrical signals. A transvaginal ultrasound (TVUS), done at the time of EMMI imaging, was used to evaluate pelvic anatomy and record uterine contractions. The data acquired was then inputted into the UPI software for calculation and image generation.

FIG. 2B further illustrates various systems and methods consistent with this disclosure that were used to assess the accuracy of UPI after the UPI data was acquired to generate UPI software electrograms, potential maps, and isochrone maps. A uterine electrograms (EMGs) was calculated from the UPI software. The red dots represent local maximum activity to demonstrate activation during a specific time window. Potential maps were generated with warm color representing high potential regions and cold color representing low potential regions, respectively. Activation maps were generated with the red color identifying an active site and the blue color identifying an inactive site. The white star within the activation maps represents the initiation site (fundus) and the white square withing the activation maps represents the termination site (cervix). Isochrone maps were generated from the activation maps with the red and blue colors representing early and late activation, respectively. The white arrows demonstrate the peristalsis propagation direction, which may be from fundus to cervix.

FIG. 2C further illustrates various systems and methods consistent with this disclosure that were used to assess the accuracy of UPI based on the UPI software generated electrograms, potential maps, and isochrone maps. Show in FIG. 2C is a detailed activation sequence of one complete uterine peristalsis initiated at the fundus and terminated at the cervix with a quantified activation ratio (%) and an instant contraction power (mV).

Represented in FIG. 2A, the study performed to assess the accuracy of the UPI procedure in non-pregnant women and data post-processing follows. First, a woman underwent a one-time, fast, anatomical (T2W sequence) 3T Siemens Prisma/Vida MRI scan (~10 mins) to acquire the patient-specific uterus-body surface geometry, while wearing up to 8 patches containing up to 128 MRI-compatible fiducial markers around the abdomen and lower back. Second, after the MRI scan, customized BioSemi pin-type electrode patches were applied to the same locations on the body surface as the MRI fiducial marker patches. Then, a 3D hand-held optical scanner was used to acquire the 3D body surface with marked electrodes. Third, an ADC box was used to record the body surface electrical signals. During the 30 minutes' electrical recording, transvaginal ultrasound (TVUS) scans of the uterus were performed by the sonographer holding the transducer probe while the patient was lying in a semi-fowler's position and TVUS clips were recorded on a GE Voluson E6 ultrasound machine synchronously during electrical recording. The duration of each clip was 20 seconds on average and 30-35 clips were acquired in total. The simultaneous TVUS detected UP direction was inspected by the sonographer with many ultrasound experiences independently and compared with that imaged by UPI for the validation purpose only.

Represented in FIG. 2B, UPI software was used to process the body surface electrical signals with a band-pass filter (0.01-0.1 Hz) and generate body surface potential maps over the entire abdomen surface. UPI software then used the method of fundamental solutions (MFS) to solve the three-dimensional Cauchy problem to compute the electrograms on the three-dimensional uterine surface. Then the time when the uterine EMGs reached the local maximal value was identified as red dots in the uterine electrograms. Electrical activation sequence of the activated myometrium during a specific observation window was formed and generated as red regions representing areas experiencing the peristalsis, and blue regions were generated representing inactive areas of the uterus. Based on the activation sequence, an isochrone map may be formed. In the isochrone maps, warm and cool colors denote regions of the uterus that activated early and late, respectively, during peristalsis. The 3D UPI isochrone maps contained 3D information of uterine activation, including the early/late activation regions and propagation patterns, etc., which enabled the patient-specific detailed understanding of human UP with high spatial and temporal resolution and coverage. The detailed activation movie of one complete uterine peristalsis initiated at the fundus and propagated to the cervix from 234 to 240 seconds is shown in FIG. 2C, with two trajectories showing the accumulated uterine activation ratio (blue curve, %) and instant peristalsis power (red curve, mV) during this peristalsis.

Quantifications of Human Uterine Peristalsis

Figure 3:
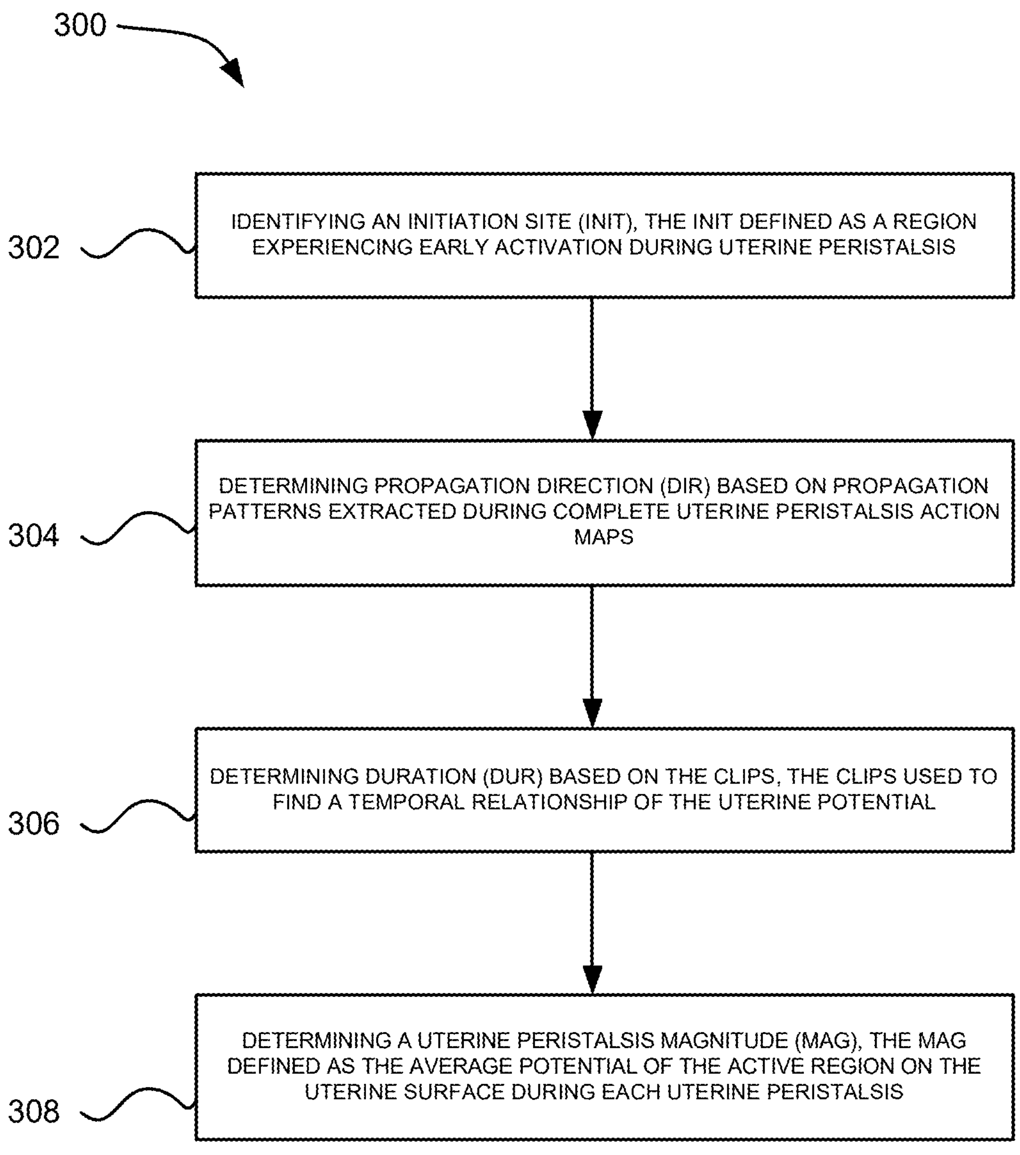
FIG. 3 is a flow diagram of an example method for defining four indices to qualitatively and quantitatively describe UP patterns.
Figure 4:
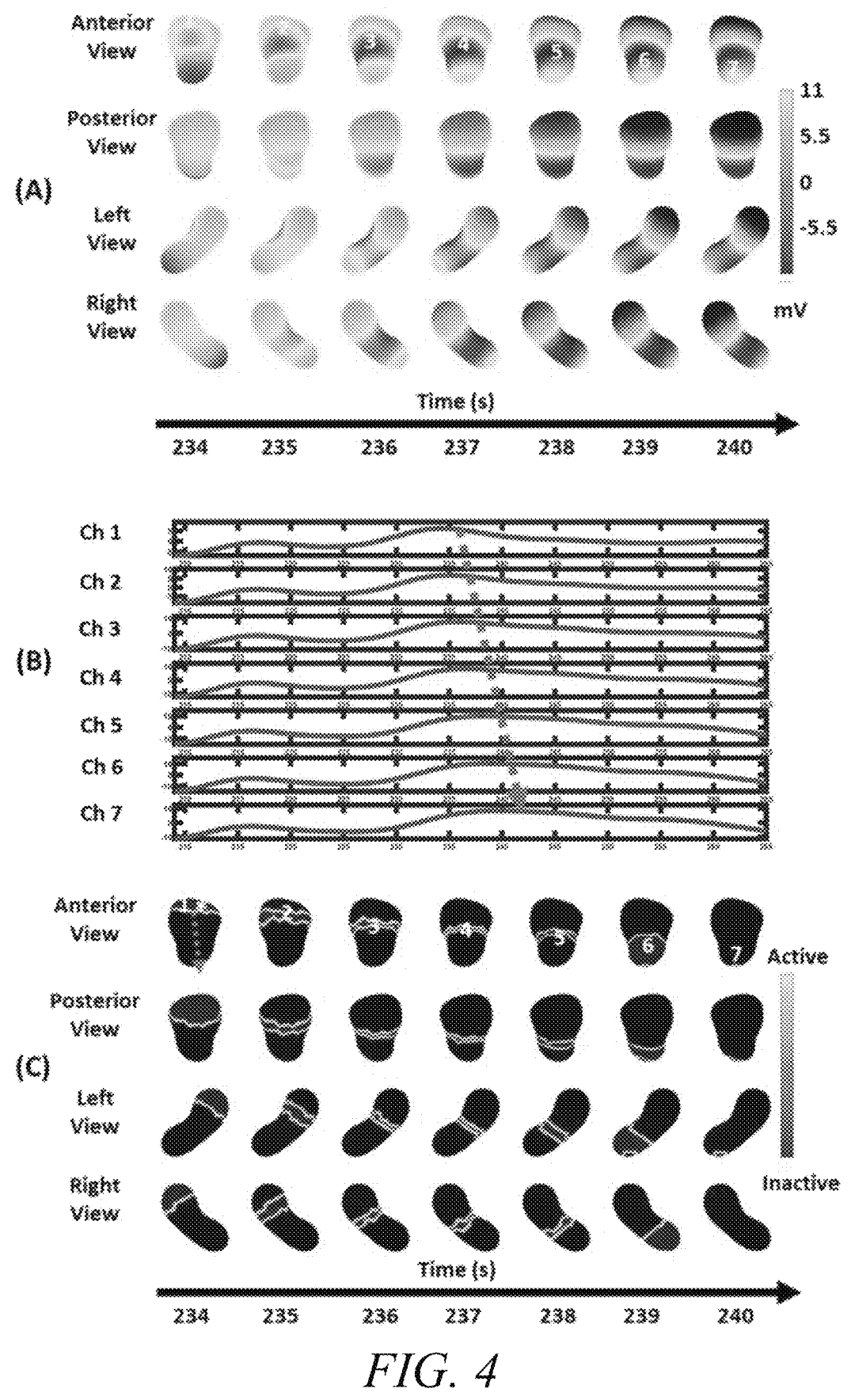

In addition to the 3D uterine activation information generated by the inverse computation, four indices were defined to qualitatively and quantitatively describe UP patterns as shown in the flow chart of FIG. 3, the results of which are illustrated in FIGS. 4A-C.

Referring to FIG. 3, step 302, the initiation site (INIT) is identified and defined as the region experiencing early activation during UP. The initiation sites were identified on the isochrone maps, which usually included the cervical region, fundal region and left/right corneal region, as shown in FIG. 4A. Secondly, at step 304, the propagation direction (DIR) was analyzed using the electrical propagation patterns extracted during complete UP activation maps. Common propagation directions of UP included cervix-to-fundus (C-F), fundus-to-cervix (F-C), opposing wave (starting at both the cervical and fundal regions), anterior-to-posterior (A-P), posterior-to-anterior (P-A), left-to-right (L-R), right-to-left (R-L). Thirdly, at step 306, the duration (DUR) was calculated based on the activation movies. The summation of the absolute value of the uterine potential at the activated region was calculated with respect to time, as shown in FIG. 4B. This temporal relationship was defined as the uterine activation curve to reflect the continuous uterine peristalses. UP duration was defined as the duration of a complete UP measured in the uterine activation curve. A shorter duration indicated that the UP was more synchronized. Fourthly, UP magnitude (MAG) was defined as the average potential of the active region on the uterine surface during each UP, as shown in FIG. 4C.

Referring only to FIGS. 4A-C, generated images (A), (B), and (C) represent a detailed demonstration of uterine peristalsis from anterior, posterior, left, and right views. (A) illustrates potential maps of uterine surfaces with seven key channels marked as white. (B) illustrates a blue curve in each channel that shows the electrogram (EMG) potential on the uterine surface. The red dot in each column represents the peak location of local maximum magnitude of observed window (e.g., 234-240 seconds). The green arrow shows the clear spatial propagation in channel level. (C) represents an activation sequence of uterine peristalsis where red represents active regions and blue represents inactive regions of the uterine peristalsis.

UPI in Non-Pregnant Women with Regular Menstrual Cycles

The UPI system was implemented to longitudinally study the uterine peristalses in seven non-pregnant women with regular menstrual cycles. One representative example is shown in FIGS. 5A-C and described below.

Figure 5:
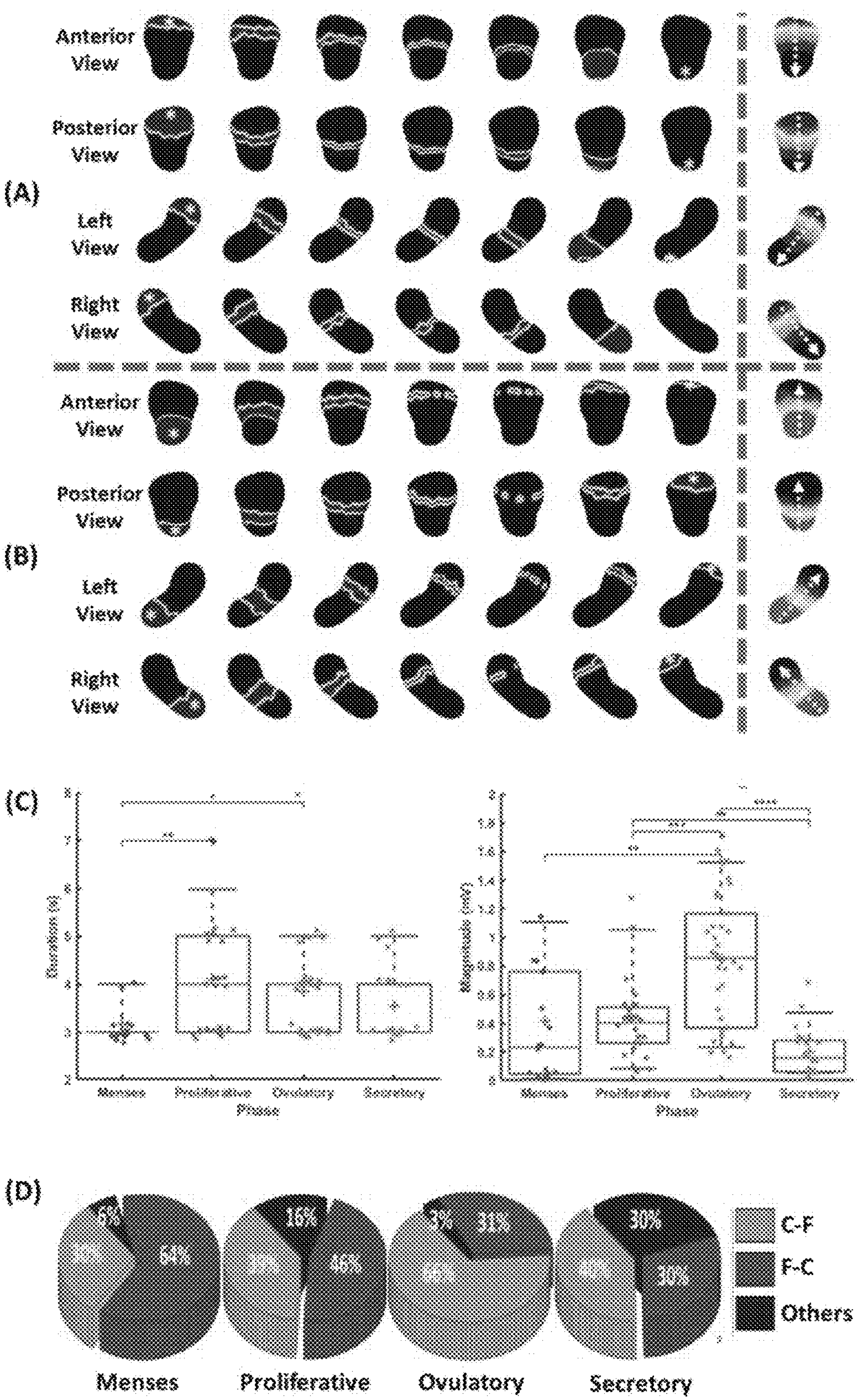
FIGS. 5A-D show UPI in subjects with regular menstrual cycle at four (menses, proliferative, ovulatory, and secretory) phases.

FIGS. 5A-C represents examples of uterine peristalsis imaging in subjects with regular menstrual cycle at four (menses, proliferative, ovulatory, and secretory) phases. (A) represents dominant fundus-cervix (F-C) UP patterns at the menses phase. (B) represents dominant fundus-cervix (F-C) UP patterns at the ovulatory phase. (C) represents boxplot of UP durations and magnitudes throughout the cycle (e.g., *: p-value<0.05, : p-value<0.01, *: p-value<0.001, **: p-value<0.001). (D) illustrates pie charts showing the dominant UP direction at each phase. A more detailed examination of FIGS. 5**A-C including the non-pregnant women with regular menstrual cycles is provided below.

FIGS. 5A-C illustrates examples of dominant uterine peristalsis patterns of a 25-year-old non-pregnant female with regular menstrual cycle at two key (menses and ovulatory) phases. The dominant UP pattern at the menses phase is from fundus to cervix, whose function is to push the blood out, shown in FIG. 5A. One representative uterine peristalsis at the ovulatory phase is from cervix to fundus using 7 seconds, as shown in FIG. 5B. There is a significant difference of duration in this normal control at the menses and ovulatory phases. There is also a significant difference of magnitude in this normal control at the menses and ovulatory phases, shown in FIG. 5C. As illustrated in FIG. 5D, at menses phase, Fundus-Cervix uterine peristalses account for 64% and Cervix-Fundus uterine peristalses account for 30% in the 19.85 minutes' observed window, which may indicate that the dominant uterine peristalsis pattern at this phase is from fundus to cervix, and its function is to push the blood out of uterus. At the proliferative phase, Fundus-Cervix uterine peristalses account for 46% and Cervix-Fundus uterine peristalses account for 39% in the 14.67 minutes' observed windows. At the ovulatory phase, Cervix-Fundus peristalses account for 66% and Fundus-Cervix peristalses account for 31% in the 18.33 minutes' observed window, which may imply that the dominant peristalsis pattern at this phase is from fundus to cervix, and its function is to facilitate the sperm transport to promote oocyte/sperm interaction. At the secretory phase, Cervix-Fundus peristalses account for 40% and Fundus-Cervix peristalses account for 30% in the 14.55 minutes' observed window. Overall, uterine peristalses have more balanced distribution over the Cervix-Fundus, Fundus-Cervix, and other directions at the proliferative and secretory phases while uterine peristalses have more dominant patterns at the menses and ovulatory phases and the dominant patterns account for more than 60% of total.

Figure 6:
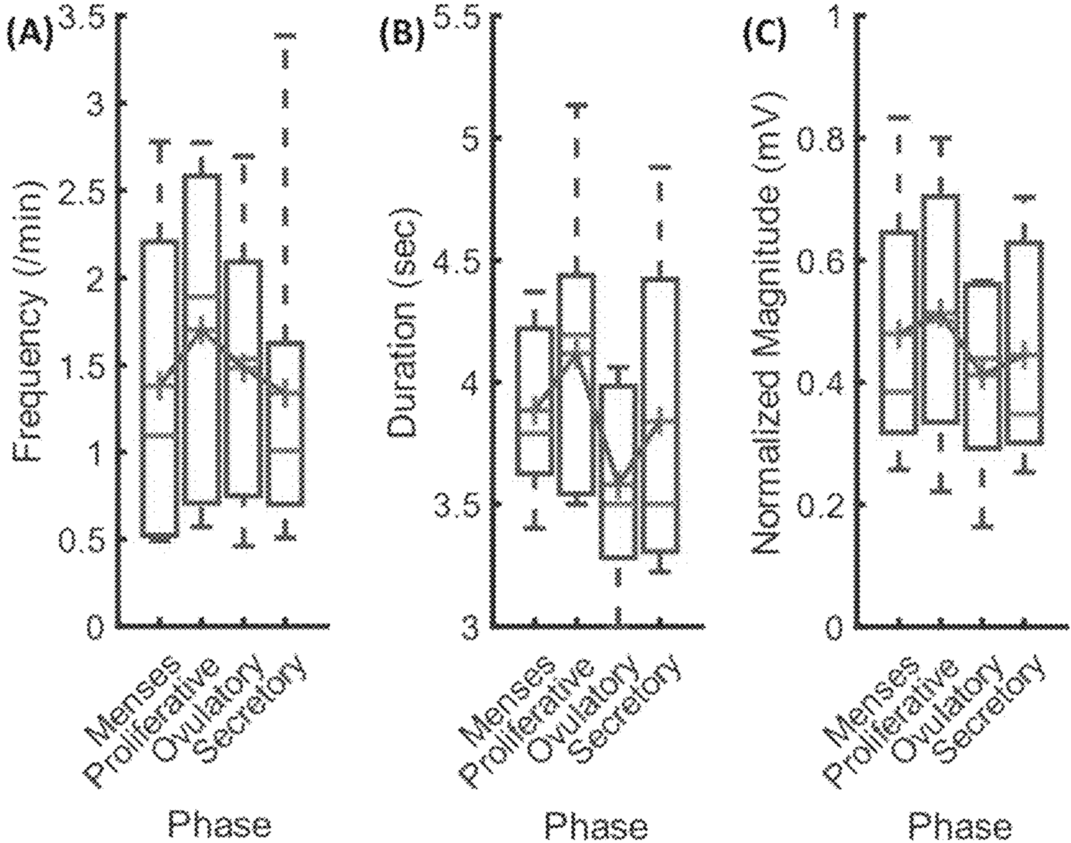
FIGS. 6A-C show longitudinal quantifications of uterine peristalsis frequency (A), duration (B), and normalized magnitude (C) throughout the complete menstrual cycle.

FIGS. 6A-C illustrates examples longitudinal quantifications of uterine peristalsis frequency, duration, and normalized magnitude throughout the complete menstrual cycle. In this illustration, red crosses show the mean values of each quantified variable at each phase.

Throughout the complete menstrual cycle, there may be a consistent trajectory in frequency as shown in FIG. 6A, duration as shown in FIG. 6B, and normalized magnitude as shown in FIG. 6C. The most frequent, longest uterine peristalses with the highest normalized magnitude appears at the proliferative phase, and the lowest frequent uterine peristalses appears at the secretory phase. The uterine peristalses with the lowest duration and lowest normalized duration appear at the ovulatory phase. Detailed summary results of regular menstrual cycles are shown below in Table 1.

TABLE 1

Results of Regular Menstrual Cycles

| Phase | Frequency (mean ± std)/min | Frequency Range/min | Duration (sec) | Duration Range (sec) | Normalized Magnitude (mV) | Normalized Magnitude Range (mV) |
|---|---|---|---|---|---|---|
| Menses | 1.38 ± 0.99 | 0.49-2.78 | 3.88 ± 0.39 | 3.4-3.7 | 0.48 ± 0.23 | 0.071-0.51 |
| Proliferative | 1.70 ± 1.00 | 0.57-2.78 | 4.15 ± 0.66 | 3.5-5.1 | 0.51 ± 0.23 | 0.12-0.87 |
| Ovulatory | 1.48 ± 0.88 | 0.46-2.70 | 3.57 ± 0.44 | 3-4.1 | 0.41 ± 0.17 | 0.095-0.98 |
| Secretory | 1.34 ± 1.16 | 0.51-3.39 | 3.90 ± 0.71 | 3.2-4.9 | 0.44 ± 0.20 | 0.073-1.05 |

UPI May Detect the Peristalses Propagating in Nonvertical Directions

Figures 7A, 7B, 7C, 7D:
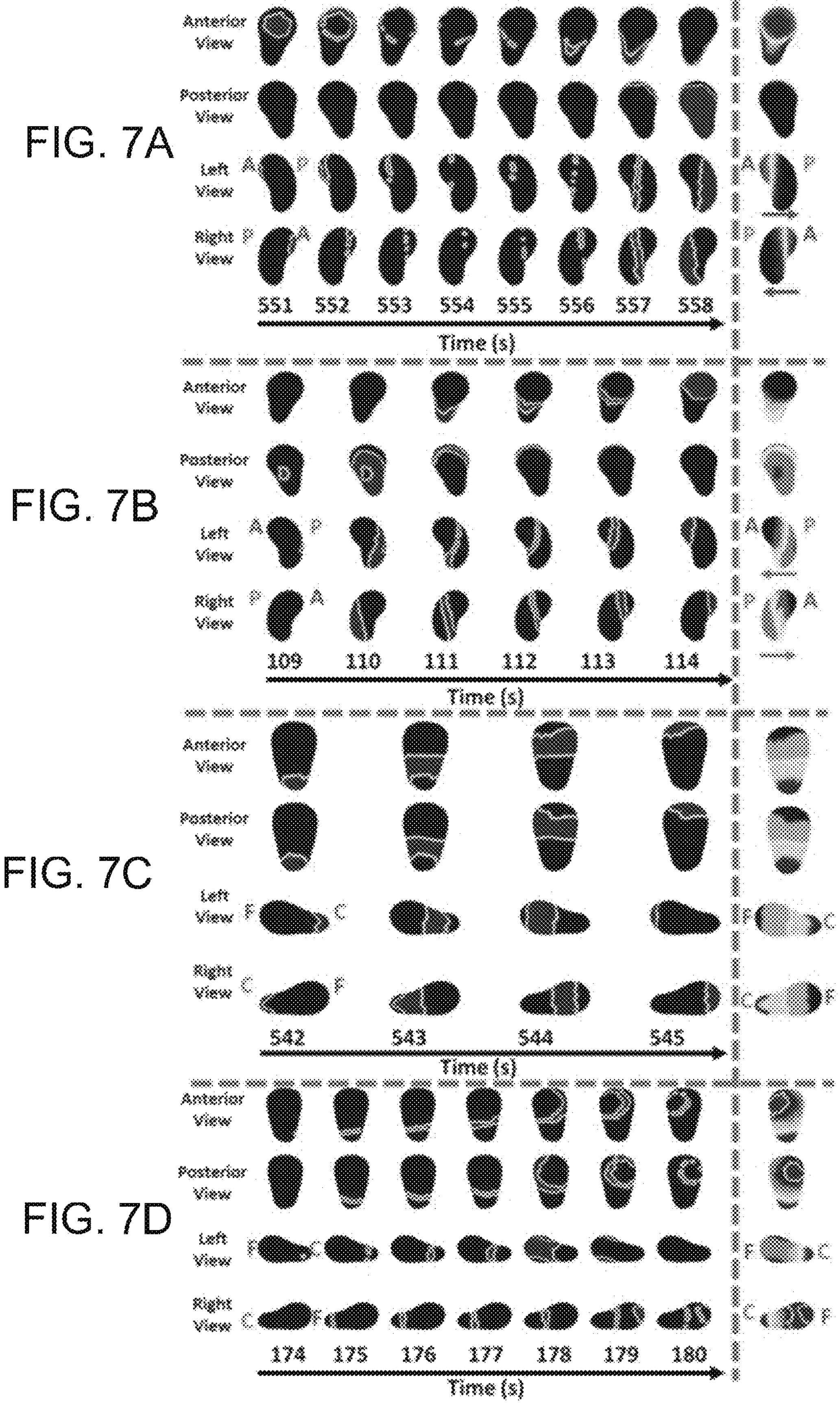
FIGS. 7A-D show UPI in two non-pregnant women with abnormal uterine bleeding and amenorrhea.

FIGS. 7A-D illustrates examples of UPI in two non-pregnant women with abnormal uterine bleeding and amenorrhea. FIG. 7A illustrates activation sequences of uterine peristalsis initiated at the upper segment of the anterior region and propagated to the posterior region from second 551 to second 558. FIG. 7B illustrates the activation sequences of uterine peristalsis initiated at the center of the posterior region and propagated to the anterior region from second 109 to second 114. FIG. 7C illustrates the activation sequences of uterine peristalsis initiated at the cervix and propagated to the fundus from second 542 to second 545. FIG. 7D illustrates activation sequences of uterine peristalsis initiated at the cervix and propagated to both the upper segments of the anterior and posterior uterus from second 174 to second 180.

Conventional TVUS may only capture peristalses propagating in the directions consistent with the probe orientation. It should be noted that UPI may detect peristalses propagating in other directions, which may be more common in abnormal gynecological groups with irregular peristalsis patterns. In various possible examples, UPI may detect peristalses propagating in directions including left-to-right, right-to-left, anterior-to-posterior, posterior-to-anterior, and various combinations of the same in various possible examples.

Two ovulatory dysfunction (abnormal uterine bleeding and amenorrhea) patients were studied at bleeding and nonbleeding episodes. The first case (shown in FIGS. 7A-B) is a 28.5-year-old patient who has heavy bleeding once per month and her menses period lasts for more than 6 days. In the 20.07 minutes' observed window, her peristalsis frequency was 0.797 times/min, peristalsis duration was 4.25±1.34 seconds, and peristalsis magnitude was 0.132±0.154 mV. Her dominant peristalsis pattern is from cervix to fundus, accounting for 56.3% of all. One abnormal uterine peristalsis was initiated at the upper segment of anterior uterus region and used 8 seconds to propagate to the posterior region, whose direction was anterior to posterior (A-P) as shown in FIG. 7A. Another abnormal uterine peristalsis was initiated at the center of posterior uterus region and used 6 seconds to propagate to the top segment of anterior region, which is close to the fundus, whose direction was posterior to anterior (P-A), as shown in FIG. 7B.

The second case is a 36-year-old amenorrhea patient (shown in FIGS. 7C-D) whose last menstrual period was 12 years ago. Her peristalsis frequency was 0.697 times/min, peristalsis duration was 3.21±0.42 seconds. Her peristalsis magnitude was 0.077±0.068 mV, which is much lower than other patients with menstrual cycles whether they are normal or abnormal. One abnormal uterine peristalsis was initiated at the cervix and propagated to the fundus, whose direction was cervix to fundus (C-F) using 4 seconds, as shown in FIG. 7C. Another abnormal uterine peristalsis was imitated at the left lower segment of uterus close to cervix, propagated upward, and finally terminated at the upper segment of anterior and posterior regions of uterus using 7 seconds, as shown in FIG. 7D.

UPI May Detect the Dominant Peristalsis Patterns in Endometriosis Patients at the Menses and Ovulatory Phases.

Figure 8:
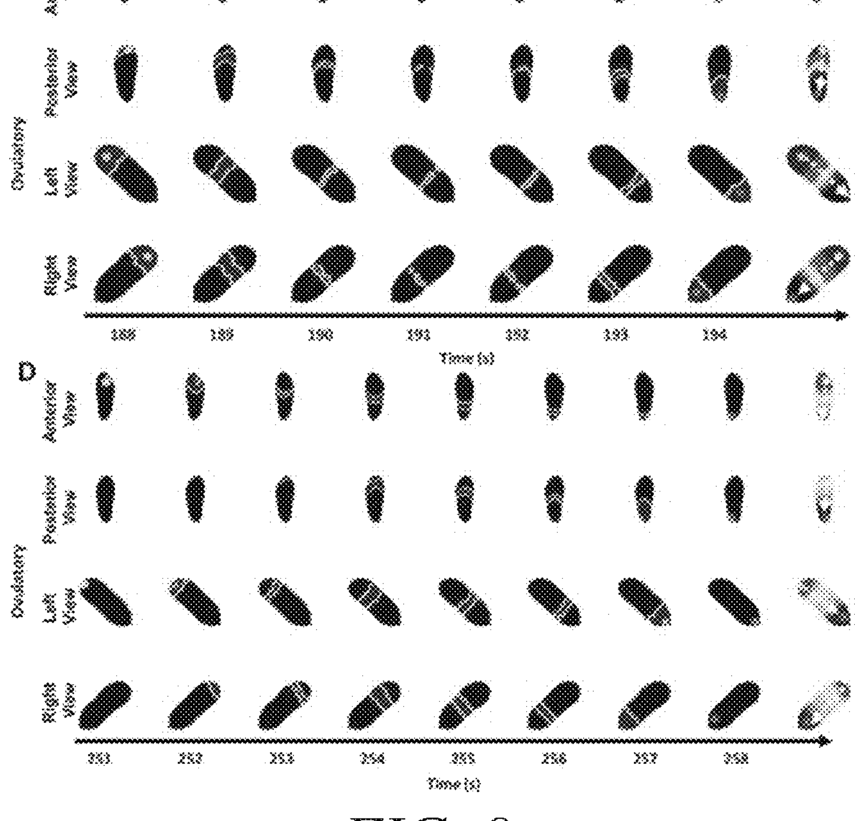
FIGS. 8A-D show UPI in one non-pregnant woman with clinically confirmed endometriosis at the menses and ovulatory phase.

FIGS. 8A-D. illustrates UPI in one non-pregnant woman with clinically confirmed endometriosis at the menses and ovulatory phase. FIG. 8A illustrates an activation sequence of uterine peristalsis initiated at the cervix and propagated upward vertically to the fundus region from 57 to 60 seconds. FIG. 8B illustrates an activation sequence of uterine peristalsis initiated at the cervix and propagated upward to the fundus region from second 159 to second 163. FIG. 8C illustrates an activation sequence of uterine peristalsis initiated at the fundus and propagated downward vertically to the cervical region from second 188 to second 194. FIG. 8D illustrates an activation sequence of uterine peristalsis initiated at the left fallopian tube and propagated downward vertically to the cervical region from second 251 to second 258.

In this example, the 34-years-old non-pregnant patient was surgically confirmed with endometriosis before the series of longitudinal imaging visits. At the menses phase, the dominant uterine peristalsis was cervix to fundus, accounting for 37.5% of the total detected peristalses, which may indicate the retrograde menstruation. At the ovulatory phase, 51.2% uterine peristalses were not in vertical directions, among which, 40.8% were in the anterior-to-posterior (22.7%) or posterior-to-anterior (18.2%) directions. Cervix-to-Fundus contractions were only 27.9% of the total contractions, which may explain the infertility of this endometriosis patient.

Included below are example equations associated with UPI.

UPI Inverse Computation

Dirichlet and Neumann conditions for the uterus surface potentials:

$$\varphi(x) = \varphi_{uterus}(x),\ x \in \Gamma_{uterus} \quad (1)$$

$$\frac{\partial \varphi(x)}{\partial n} = 0,\ x \in \Gamma_{uterus}$$

Dirichlet and Neumann conditions for the body surface potentials are:

$$\varphi'(x) = \varphi_{body}(x) + \varphi_{error}(x),\ x \in \Gamma_{body} \quad (2)$$

$$\frac{\partial \varphi'(x)}{\partial n} = 0,\ x \in \Gamma_{body}$$

Method of fundamental solutions (MFS) is used to discretize the Laplacian equation and Dirichlet and Neumann conditions. MFS is accurate for solving the bioelectric field inverse problem in both electrocardiographic electromyometrial systems.

$$A_{2nb*(nu+1)}\begin{pmatrix} a_0 \\ a_{uterus} \end{pmatrix} = \varphi_{body} \quad (3)$$

Here, A is a linear transform matrix of 2nb×(nu+1) and $\varphi_{body}$ is the measured body surface potentials from the electrical recording. Here, A is a partitioned matrix consisting of the Dirichlet condition D and Neumann condition N, which can be written as:

$$A = \begin{pmatrix} 1_{nb*1} & D_{nb*nu} \\ 0_{nb*1} & N_{nb*nu} \end{pmatrix} \quad (4)$$

Combining equations (1) and (3) gives the following augmented matrix equation:

$$\begin{pmatrix} & \tilde{A}_{2nb*(1+nu+nb)} & \\ 0_{nu*1} & B_{nu*nu} & 0_{nu+nb} \end{pmatrix}\begin{pmatrix} a_0 \\ a_{uterus} \\ a_{body} \end{pmatrix} = \begin{pmatrix} \varphi_{body} \\ 0_{nu*1} \end{pmatrix} \quad (6)$$

Here, Ã is an augmented 2nb*(1+nu+nb) transform matrix to encode the relationship between the body surface potential and uterine surface potential. $B_{nu*nu}$ is the equipotential constraint applied on the uterus layers and $\varphi_{body}$is a nu dimensional vector of the body surface potentials. And this matrix equation cannot be solved directly as it is a seriously ill-posed inverse problem. Therefore, Tikhonov regularization with CRESO-determined regularization parameter is used to obtain the coefficient vector.

When the coefficient vector is obtained, the uterus surface potentials can be calculated using the forward model:

$$\varphi_{uterus} = \tilde{A}_{nb*(nu+nb)}\begin{pmatrix} a_{uterus} \\ a_{body} \end{pmatrix} + 1_{nn*1} * a_0 \quad (7)$$

Here, $\hat{A}_{nu*(nu+nb)}$ is the forward matrix generated from the Dirichlet condition of the uterus surface.

Systems for Noninvasively Determining Uterine Peristalsis Electrical Activity of a Mammal The disclosure now turns to a system for noninvasively determining uterine peristalsis electrical activity of a mammal. The mammal may have a body surface surrounding a uterus of the mammal.

A description of an example system for noninvasively determining uterine peristalsis electrical activity in a mammal, as illustrated in FIG. 9A, is first disclosed herein.

FIG. 9A shows an example system 900 for noninvasively determining uterine peristalsis electrical activity of a mammal. The system 900 may include the first medical imaging modality 901, the second medical imaging modality 902, and the plurality of imaging markers. In some examples systems, the system 900 may include a third medical imaging modality, such as the transvaginal ultrasound. The medical imaging modalities 901 and 902 may be in connection with a computing system 906. In some examples, the medical imaging modalities 901 and 902 may be in connection with a communication interface 914 of computing system 906. In some examples, the medical imaging modalities 901 and 902 may be operable to perform the imaging scan to generate a set of generated three-dimensional images of the uterus of the mammal respectively, as seen in FIG. 1B, steps 110 and 114. In some examples, the medical imaging modalities 901 and 902 are each an imaging modality that is substantially safe for use during pregnancy and is operable to record three-dimensional images of the uterus of the mammal. In some examples, the medical imaging modality 902 may include a magnetic resonance imaging machine (MRI), hand-held optical scanner, or an ultrasound machine.

The system 900 may also include an electrical mapping device 904 and electrodes. The electrical mapping device 904 may be in connection with the computing system 906. In some examples, the electrical mapping device 904 may be in connection, via a connection 912, with at least one processor, such as the processor 910 of the computing system 906. The electrical mapping device 904 may be in connection with the electrodes and may be operable to detect the body surface electrical activity of the body surface during at least one contraction and/or during an operation window defined by a start time and a stop time.

The system 900 may further include a computing system having at least one non-transitory computer readable medium. In some examples, the at least one non-transitory computer readable medium may include the system memory 908.

The system 900 may include at least one processor, such as the processor 910. The least one non-transitory computer readable medium, e.g., the system memory 908, may store instructions which when executed by processor 910, to cause processor 910 to perform at least one step. In at least one example, the instructions from the non-transitory computer readable medium are instructions encoded in the UPI software. In some examples, the instructions may cause the processor 910 to receive data from the medical imaging modalities 901 and 902 and/or the electrical mapping device 904, such as the sets of generated three-dimensional images, the plurality of locations, and/or the body surface electrical potentials. In some examples, the instructions may cause the processor 910 to receive data from a third medical imaging modality, such as from a transvaginal ultrasound. In some examples, the instructions may cause the processor 910 to determine a body-uterus geometry of the mammal, such as in step 102 of FIGS. 1A and 1B. In some examples, the instructions may cause the processor 910 to generate sets of three-dimensional uterine peristalsis electrical potential maps based on the body-uterus geometry and the plurality of body surface electrical potentials, such as in step 106 of FIG. 1A and step 118 of FIG. 1B. In some examples, the instructions may cause the processor 910 to derive electrograms and/or isochrones maps from the uterine surface electrical potential maps, such as in step 106 of FIG. 1A.

Referring to FIGS. 9A and 9B, system 900 may include a computing system, such as the computing system 906. FIG. 9B shows an example computing system 906. In some examples computing system 906 is a distributed system in which the functions described in this disclosure can be distributed within a datacenter, multiple datacenters, a peer network, throughout layers of a fog network, etc. In some examples, one or more of the described system components represents many such components each performing some or all of the function for which the component is described. In some examples, the components can be physical or virtual devices.

The computing system 906 may include a connection 912 by which components of system 900 are in communication with each other. Connection 912 can be a physical connection via a bus, or a direct connection into processor 910, such as in a chipset or system-on-chip architecture. Connection 912 can also be a virtual connection, networked connection, or logical connection.

Also included in the computing system 906 are the at least one processing unit (CPU or processor) 910 and various system components coupled via the connection 912, including system memory 908, read only memory (ROM) 920 or random access memory (RAM) 922 to processor 910. Computing system 906 can include a cache of high-speed memory 924 connected directly with, in close proximity to, or integrated as part of processor 910.

Processor 910 can include any general-purpose processor and a hardware service or software service, such as services 926, 926, and 930 stored in storage device 932, operable to control processor 910 as well as a special-purpose processor where software instructions are incorporated into the actual processor design. Processor 910 may essentially be a completely self-contained computing system, containing multiple cores or processors, a bus, memory controller, cache, etc. A multi-core processor may be symmetric or asymmetric.

To enable user interaction, computing system 906 includes an input device 916, as seen in FIGS. 9A and 9B, which can represent any number of input mechanisms, such as a microphone for speech, a touch-sensitive screen for gesture or graphical input, keyboard, mouse, motion input, speech, etc. Computing system 906 can also include output device 918, as seen in FIGS. 9A and 9B, which can be one or more of a number of output mechanisms known to those of skill in the art. In some instances, multimodal systems can enable a user to provide multiple types of input/output to communicate with computing system 906. Computing system 906 can include the communications interface 914, which can generally govern and manage the user input and system output, and also connect computing system 906 to other nodes in a network. In some examples, the output device 918 may include a display monitor operable to exhibit the uterine surface electrical activity, such as uterine peristalsis electrical potential maps, generated at step 106 of FIG. 1A. In such examples, the display can allow for improved monitoring of uterine contractions by facilitating the comprehensive evaluation of three-dimensional uterine electrical activation patterns at high spatial and temporal resolution in real or near-to-real time. There is no restriction on operating on any particular hardware arrangement and therefore the basic features here may easily be substituted for improved hardware or firmware arrangements as they are developed.

Storage device 932 can be a non-volatile memory device and can be a hard disk or other types of computer readable media which can store data that are accessible by a computer, such as magnetic cassettes, flash memory cards, solid state memory devices, digital versatile disks, cartridges, battery backed random access memories (RAMs), read only memory (ROM), and/or some combination of these devices.

The storage device 932 can include software services, servers, services, etc., that when the code that defines such software is executed by the processor 910, it causes the system to perform a function. In some examples, a hardware service that performs a particular function can include the software component stored in a computer-readable medium in connection with the necessary hardware components, such as processor 910, connection 912, output device 918, etc., to carry out the function.

EXAMPLES

Example 1

This example was conducted with female participants between the ages of 18 and 37 that had regular, predictable menstrual cycles every 24-35 days. Each participant was imaged with the UPI system four times during one menstrual cycle, once during menses, early proliferative, late proliferative (pre-ovulatory), and secretory phase.

Human uterine activity changes dynamically across the menstrual cycle. Menses occurs when serum concentrations of the ovarian hormones, progesterone, and estrogen decrease, signaling the endometrial layer of the uterus to shed blood and epithelial cells through the cervix. In the proliferative phase, the uterine epithelium thickens in response to estradiol production from follicle growth in one or both ovaries. During the peri-ovulatory phase, an oocyte is released from the ovarian follicle, is picked up by the fimbria of the fallopian tube and begins traversing through the fallopian tube. With the correct timing of sperm exposure from unprotected sexual intercourse, fertilization of the oocyte may occur within the ampulla of the fallopian tube. The early embryo enters the uterine cavity during the secretory phase. The uterine epithelium undergoes secretory changes in preparation for potential embryo implantation. These epithelial changes are well regulated, as is proper uterine activity in each phase of the menstrual cycle.

The sub endometrial layer of the uterine myometrium contributes to uterine functions by generating slow, low-magnitude, spontaneous contractions termed uterine peristalsis. The peristalsis waves vary in spatial and temporal patterns and frequency throughout the phases of the menstrual cycle. During the menstrual cycle, it is commonly believed that peristalsis waves primarily propagate from the fundus to the cervix, aiding in the expulsion of blood and tissue. In contrast, during the peri-ovulatory phase, it is widely believed that peristalsis waves predominantly propagate from the cervix toward the fundus, serving as a crucial mechanism for transporting sperm towards the fallopian tubes.

Transvaginal ultrasound (TVUS) can detect the sub endometrial deformation waves traveling from the cervix to the fundus and waves traveling from the fundus to the cervix. However, TVUS has a few disadvantages that limit its utility in quantitating uterine peristalsis in patients and research participants. First, TVUS requires insertion of a vaginal probe, which can be uncomfortable or even painful. Of significant importance, the insertion of the probe and the emission of ultrasound waves have the potential to modify the peristalsis pattern. Second, the interobserver agreement is often limited by the real-time analysis of TVUS images. An alternative analysis method is high-speed replay, but this is very time-consuming. Third, the quality of TVUS image acquisition may be limited by the position and orientation of the uterus. Thus, TVUS method is subjective and operator- and time-dependent and may result in incomplete or inaccurate findings.

Other methods that have been used to study uterine peristalsis also all have significant limitations. Intrauterine pressure catheters are invasive, and a catheter placed inside the uterus could alter peristalsis patterns. Hysterosalpingography (HSSG) is a procedure in which X-rays are used to detect a radiographic contrast dye injected into the uterus and fallopian tubes. Although HSSG measures are objective, HSSG cannot be used to measure peristalsis amplitude or frequency, and radiation exposure limits the imaging duration. Cine magnetic resonance imaging (MRI) can be used to detect uterine peristalsis by acquiring sequential images over time and playing the MRI frames 12 times faster than the actual speed. However, extended cine MRI is expensive, time-consuming, operator-dependent, and it cannot reveal the initiation and termination sites of uterine peristalsis. Moreover, all these modalities can be uncomfortable for the participant and cannot be used for long-term observation.

An alternative technique for evaluating uterine peristalsis is to record the slow-wave electrical signals that drive the mechanical contractions. For example, one study measured spontaneous electrical signals in ex vivo human uterus. In another study, electrodes were placed inside the nonpregnant uterine cavity to directly measure electrical activity on the uterine surface. Additionally, a further study used transabdominal electromyography (EMG) to measure uterine electrical activity from electrodes placed on the body surface. However, this transabdominal EMG method solely focuses on capturing high-frequency electrical signals from a small abdominal area, and therefore, is incapable of characterizing the spatial patterns of peristalsis on the uterine surface. Consequently, there is a pressing need for a novel electrophysiological imaging method to noninvasively and quantitatively define the detailed features of human uterine peristalsis over the entire uterus and a long period of time.

An electrophysiological imaging system called electromyometrial imaging (EMMI) can quantitatively measure the electrical activity underlying uterine contractions during labor. Herein, a new uterine peristalsis imaging (UPI) system based on EMMI to longitudinally image the four-dimensional (4D) electrical activation patterns of uterine peristalsis over each phase of the menstrual cycle in healthy, nonpregnant participants with normal menstrual cycles is developed. The UPI system employs wearable electrode sensors and can provide precise, quantitative evidence that uterine peristalsis changes in frequency, direction, duration, magnitude, and power throughout the menstrual cycle. This non-invasive nature ensures minimal discomfort to patients, which makes it a very safe and feasible tool for longitudinal studies and clinical application.

Uterine Peristalsis Imaging (UPI) System

Figure 10:
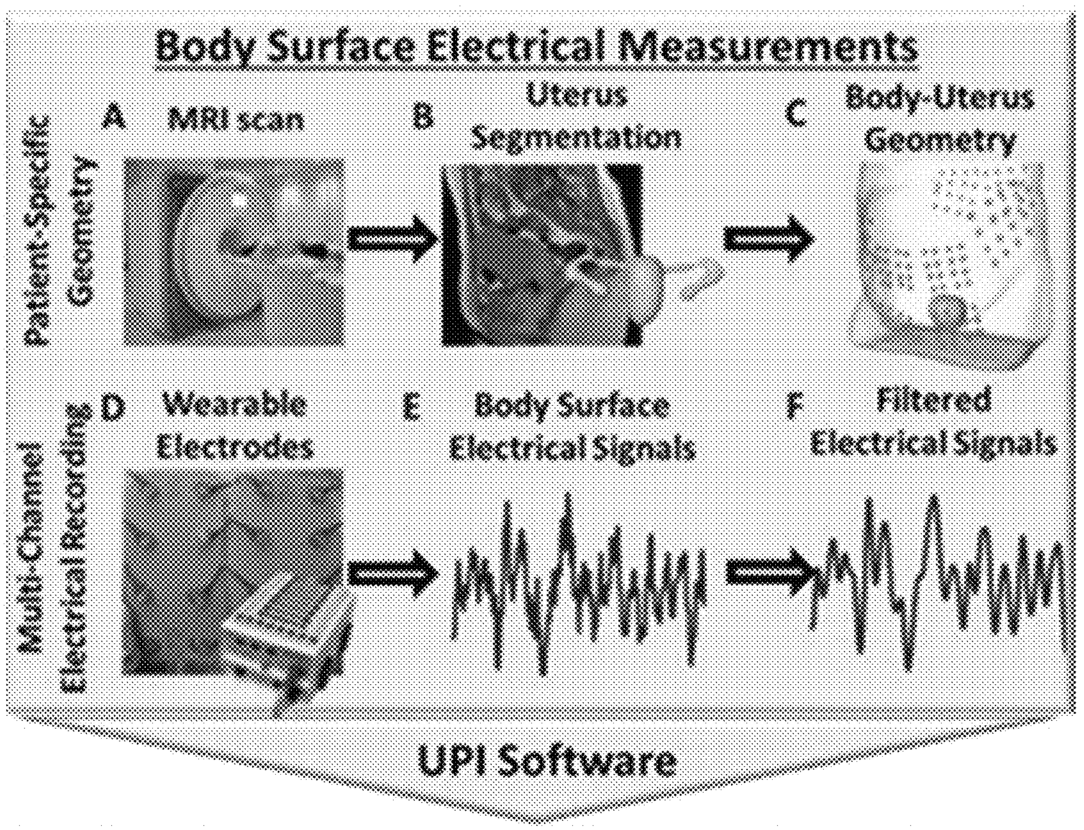
FIG. 10A shows an anatomical MRI conducted to determine the uterus-body surface geometry.
FIG. 10B shows a segmentation of body surface, uterus surface, and fallopian tubes.
FIG. 10C shows a patient-specific body-uterus geometry where the pink dots indicate MRI-compatible markers.
FIG. 10D shows electrode patches placed on a participant's abdomen and back in the same positions as the MRI-compatible markers.
FIG. 10E shows electrical signal measurements on the patient's body surface.
FIG. 10F shows filtered electrical signals (bandwidth: 0.01-0.05 Hz).
FIG. 10G shows uterine surface electrical signals from one uterine surface point near the cervical region (white plus sign in FIG. 10I), where red dots denote the points of steepest negative slope to represent the activation times during peristalsis cycles.
FIG. 10H shows uterine surface electrical signals from one uterine surface point around the fundal region (white asterisk in FIG. 10I).
FIG. 10I shows a detailed activation sequence of one complete uterine peristalsis wave initiated near the fundus and terminate near the cervix, where blue indicates inactive uterine regions and red indicates active uterine regions.
Figure 10:
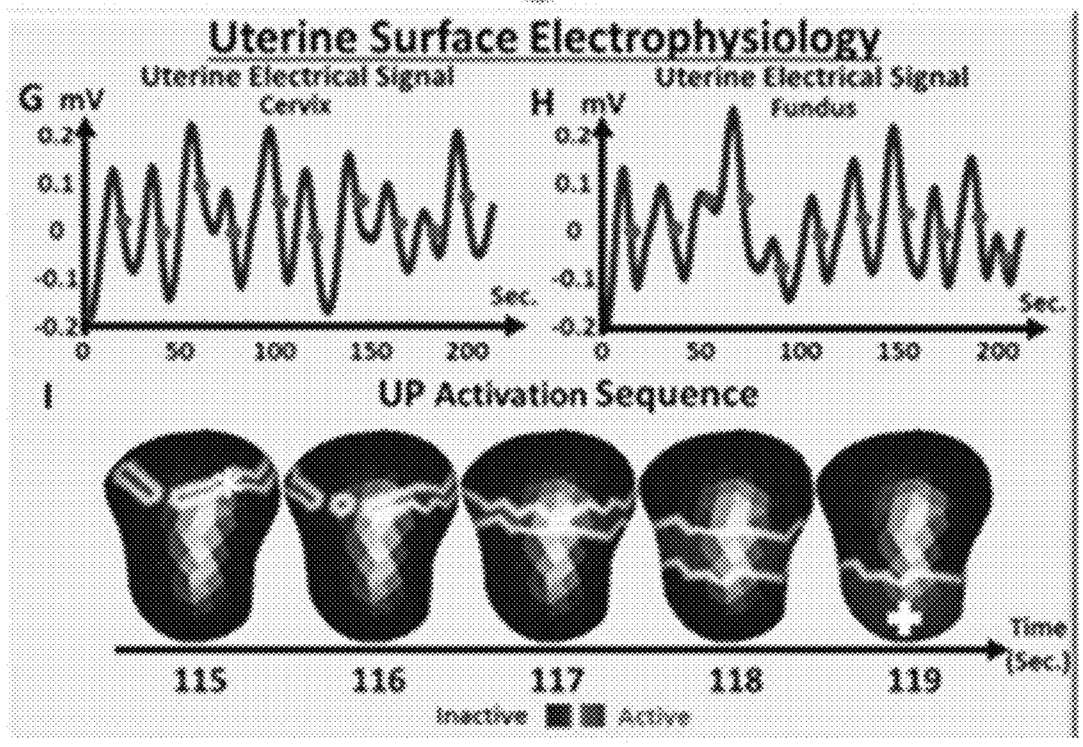

The UPI system is illustrated in FIGS. 10A-I. First, while applying MRI-compatible fiducial markers around the abdomen and lower back, a woman undergoes a one-time, fast, anatomical MRI scan (FIG. 10A) to acquire the patient-specific uterus-body surface geometry (FIGS. 10B-C). Second, customized wearable pin-type electrode patches are applied to the same locations on the body surface as the MRI fiducial markers (FIG. 10D). Body surface electrical signals (FIG. 10E) are recorded for 20-30 minutes, and electrical signals (FIG. 10F) are recorded with a band-pass filter (0.01-0.05 Hz). Third, UPI software is used to map electrical signals to each point on the entire three-dimensional (3D) uterine surface (FIGS. 10G-H). These electrical signals are used to derive activation sequences (FIG. 10I).

4D Spatial-Temporal Quantification of Uterine Peristalsis Patterns

Figure 11:
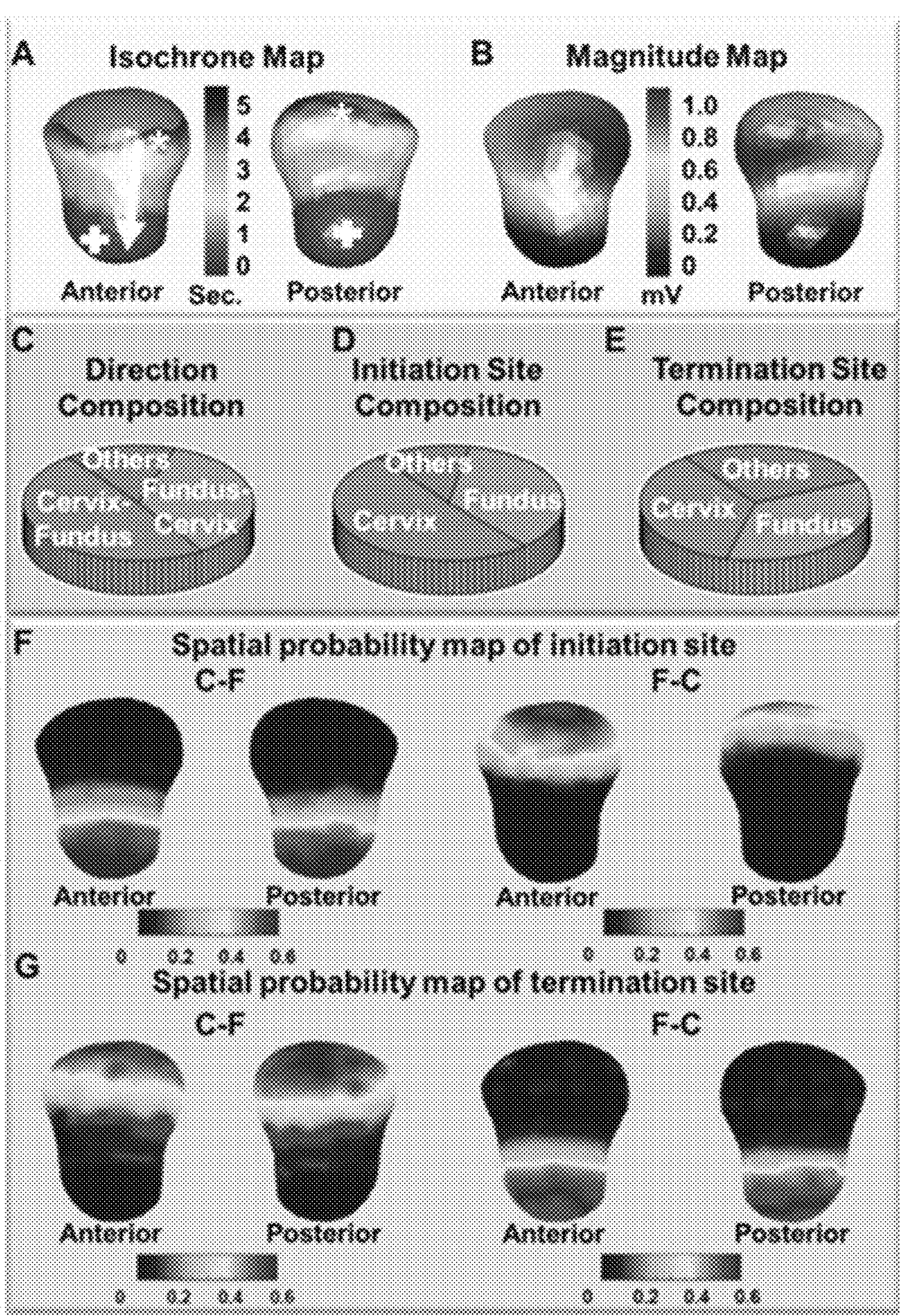
FIG. 11A shows uterine isochrone maps from the same uterine peristalsis as in FIG. 10I. Warm and cool colors represent early and late activation, respectively. The white arrow depicts the peristalsis wave propagation direction.
FIG. 11B shows a uterine magnitude map from the same uterine peristalsis wave in FIG. 10I, showing the magnitude distribution over the entire 3D uterine surface in one peristalsis.
FIG. 11C shows a distribution of uterine peristalsis directions (Cervix-Fundus, Fundus-Cervix, and others).
FIG. 11D shows a distribution of uterine peristalsis initiation sites.
FIG. 11E shows a distribution of uterine peristalsis termination sites.
FIG. 11F shows a spatial probability map of initiation site of uterine peristalsis for an entire imaging session.
FIG. 11G shows a spatial probability map of termination site of uterine peristalsis for an entire imaging session.

Uterine isochrone maps (FIG. 11A) were generated according to the activation sequence (FIG. 10I). Uterine surface data were analyzed to generate uterine magnitude maps (FIG. 11B). Based on uterine isochrone maps, the peristalsis wave direction (Cervix-Fundus, Fundus-Cervix, or others) and locations of the initiation and termination sites (cervix area, fundus area, and other areas) for each peristalsis wave were defined and summerized for all peristalsis waves recorded during the entire imaging session (FIGS. 11C-E). Finally, the initiation (FIG. 11F) and termination site (FIG. 11G) distribution probability maps for Cervix-Fundus and Fundus-Cervix peristalses were generated for the entire imaging session.

UPI Findings in Healthy Participant with Regular Menstrual Cycle

Figures 12A, 12B:
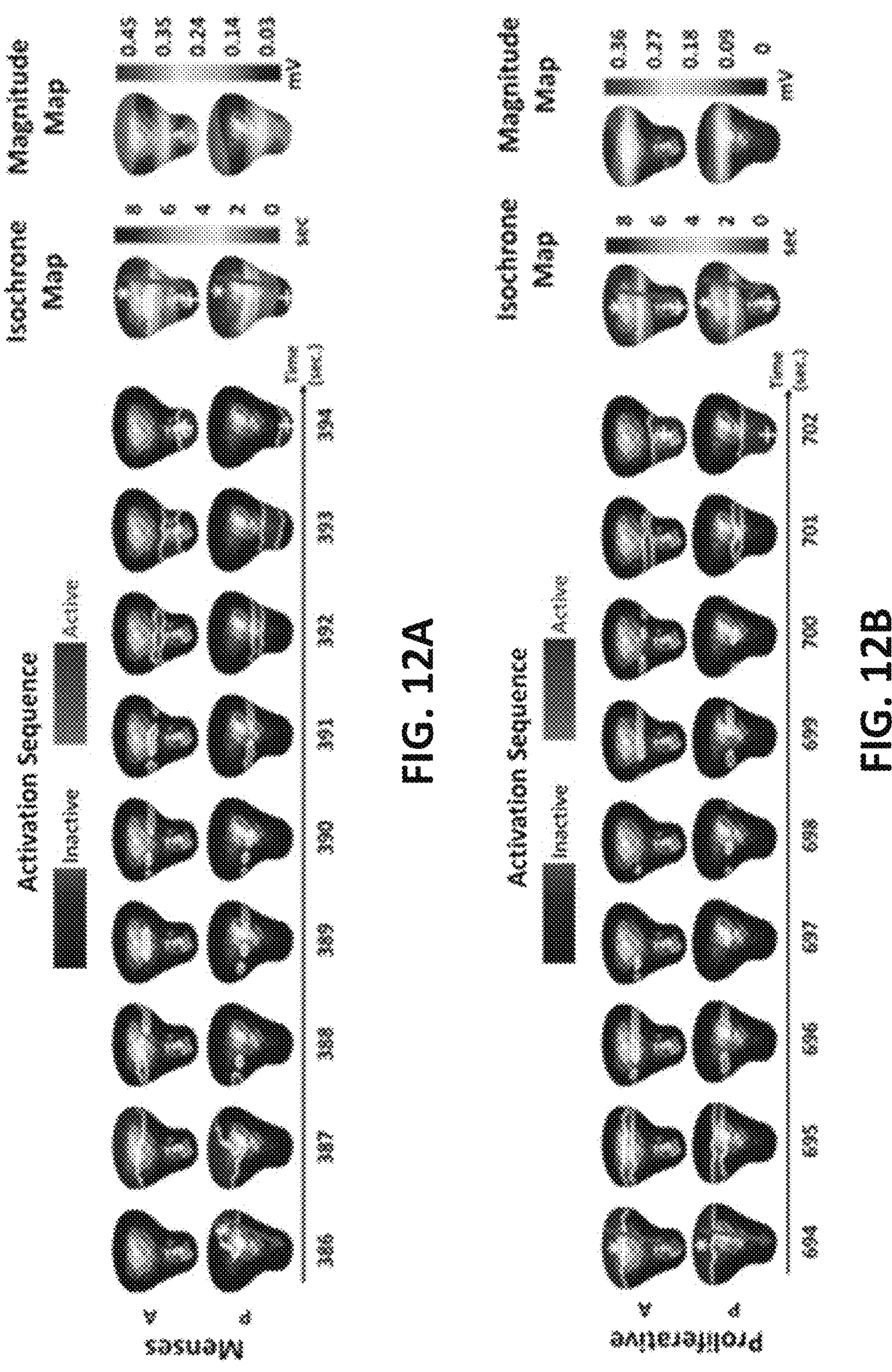
FIG. 12A shows a dominant Fundus-Cervix uterine peristalsis pattern during the menses phase.
FIG. 12B shows a dominant Fundus-Cervix uterine peristalsis during the proliferative phase.
Figures 12C, 12D:
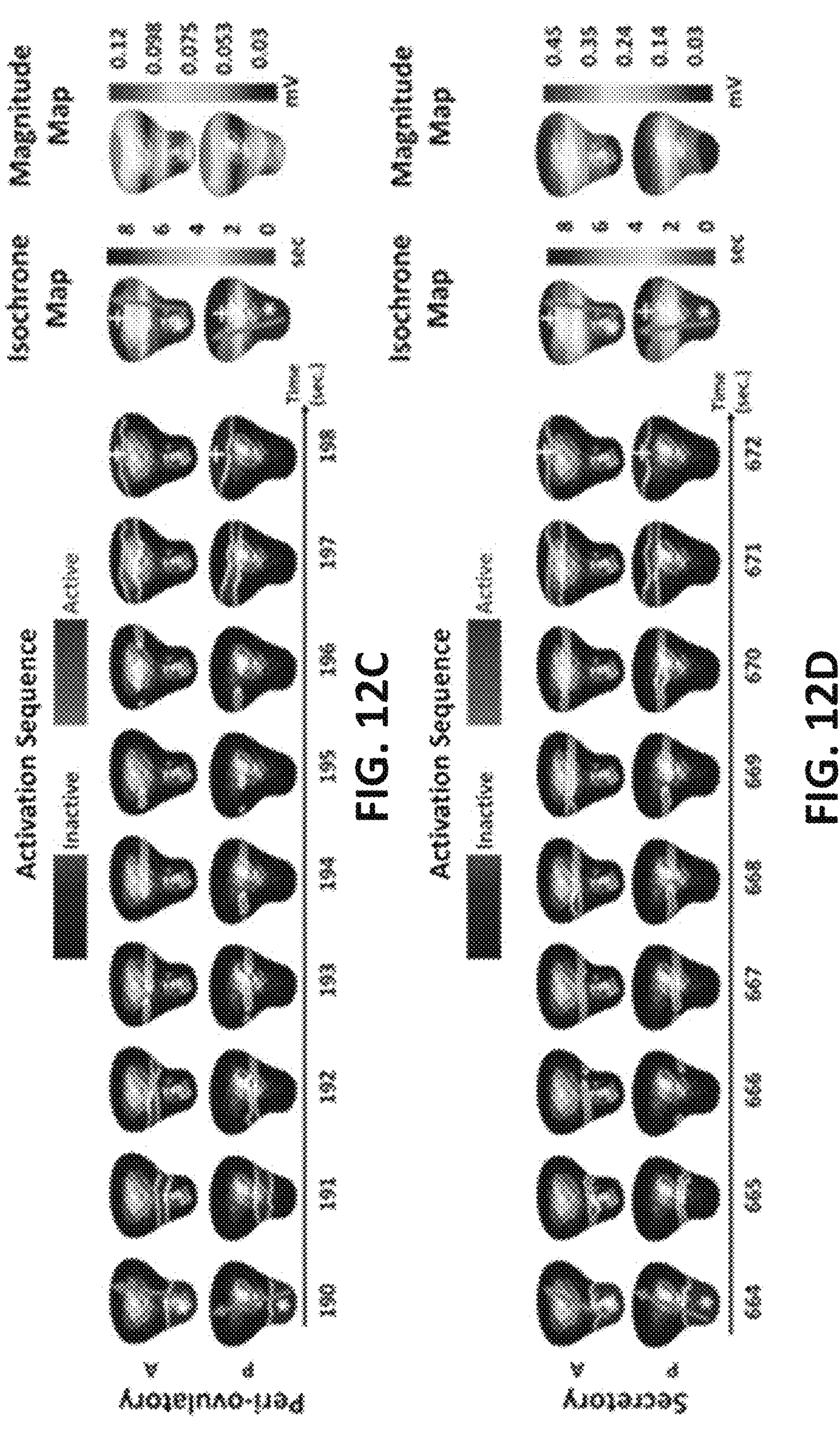
FIG. 12C shows Cervix-Fundus uterine peristalsis patterns during the peri-ovulatory phase.
FIG. 12D shows Cervix-Fundus uterine peristalsis patterns during the secretory phase. In each panel of FIGS. 12A-12D A represents the anterior view and P represents the posterior view.

In FIGS. 12A-D, representative uterine peristalsis waves of a 32-year-old healthy participant are presented. During the menses phase, 40.4% of waves traversed from near the fundus toward the cervix (Fundus-Cervix), and 25.5% traversed from near the cervix toward the fundus (Cervix-Fundus) (FIG. 12A). During the proliferative phase, 42.7% of waves were Fundus-Cervix and 36.5% were Cervix-Fundus (FIG. 12B). During the ovulatory phase, 45.2% of waves were Cervix-Fundus, and 33.3% were Fundus-Cervix (FIG. 12C). In the secretory phase, 41.9% of waves were Cervix-Fundus, and 32.6% were Fundus-Cervix (FIG. 12D). In all cases in which the direction of peristalsis in TVUS images (n=88/94, 93.6% of waves) was determined, the direction of peristalsis imaged by UPI matched the direction observed by TVUS.

UPI-Derived Quantifications are Distinct Among Phases in Healthy Participants

The UPI system was used to image uterine peristalsis in 26 healthy nonpregnant females with regular menstrual cycles. Imaging was conducted during each menstrual phase. Demographics and obstetric and gynecologic history of enrolled participants are shown in Table 2.

TABLE 2

Demographics of enrolled patients (N = 26) with regular menstrual cycles. Mean value and 95% confidence interval are shown for each numerical variable.

| | |
|---|---|
| Age, years | 27.75 (25.96-29.54) |
| BMI, kg/m^2 | 29.99 (26.82-33.18) |
| Race, n (%) | |
| White | 14 (53.8%) |
| Black | 9 (34.6%) |
| Asian | 2 (7.7%) |
| Other | 1 (3.8%) |
| Cycle length, days | 28.35 (27.46-29.24) |

TABLE 2-continued

Demographics of enrolled patients (N = 26) with regular menstrual cycles. Mean value and 95% confidence interval are shown for each numerical variable.

| Phase | Menses | Proliferative | Ovulatory | Secretory |
|---|---|---|---|---|
| Estradiol (pg/mL) | 33.7 (27.0-40.4) | 93.9 (76.7-111.1) | 155.9 (119.3-192.6) | 118.9 (99.7-138.2) |
| Progesterone (ng/mL) | 0.28 (0.21-0.35) | 0.20 (0.20-0.21) | 2.00 (1.20-2.80) | 8.34 (6.52-10.16) |
| Endometrial thickness (mm) | 3.50 (2.66-4.34) | 6.79 (5.94-7.64) | 8.92 (7.56-10.28) | 9.43 (8.28-10.58) |

Figure 13I:
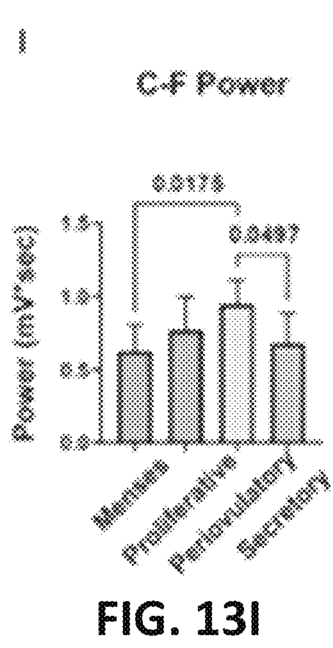
Figure 13J:
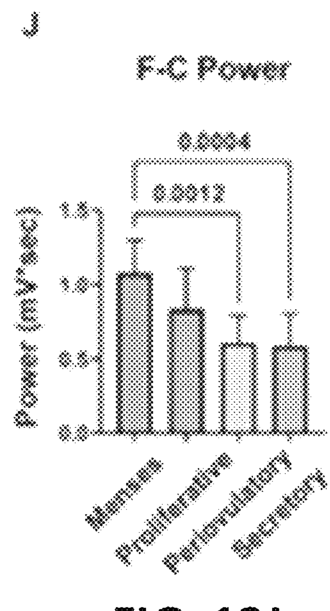
Figure 13K:
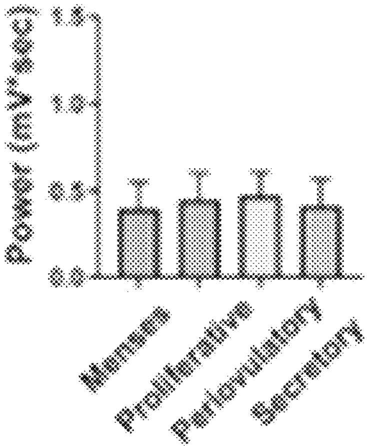

In total, uterine peristalsis waves over 52 hours of electrical recording in 104 clinical visits were imaged. After compiling data from all 26 participants, the average direction ratio, duration, magnitude, and power were graphed. The longitudinal peristalsis frequency in the standard 28-day menstrual cycle (FIG. 13A), frequency (FIG. 13B), average direction ratio (FIGS. 13C-E), magnitude (FIGS. 13F-H), and power (FIGS. 13I-K) of peristalsis waves from each participant, with data during menses, proliferative, periovulatory, and secretory phases were graphed. At all four phases, Cervix-Fundus or Fundus-Cervix waves were much more dominant (FIGS. 13C-E) and had greater magnitude (FIGS. 13F-H) and power (FIGS. 13I-K) than peristaltic waves in other directions. The peri-ovulatory phase exhibits the highest peristalsis frequency (3.13 [2.72, 3.54]), while the menses phase demonstrates the lowest frequency (1.43 [1.21, 1.67]) (FIG. 13B). During the peri-ovulatory phase, Cervix-Fundus peristalses displays the highest direction ratio (0.58 [0.54, 0.62], FIG. 13C) and greatest magnitude (0.42 [0.33, 0.51], FIG. 13I), whereas the menses phase exhibits the lowest direction ratio (0.36 [0.33, 0.38], FIG. 13C). In the menses phase, Fundus-Cervix peristalses shows the highest direction ratio (0.53 [0.49, 0.57], FIG. 13D). No significant differences in direction ratio, magnitude, or power were observed in peristalses occurring in other directions between the phases.

Asymmetric/Unilateral C-F Peristalsis Direction Correlates with Dominant Follicle During Ovulation Unexpectedly, it was observed that Cervix-Fundus peristalsis waves during the peri-ovulatory phase tend to move preferentially toward one fallopian tube in this normal cohort. In fifteen healthy participants in this study, it was determined which ovary had a dominant follicle by clinical TVUS. Then whether the Cervix-Fundus peristalsis propagated in the direction of the dominant follicle was studied. The clinical characteristics and measurements of these patients were summarized in Table 3.

TABLE 3

Clinical characteristics and measurements in fifteen healthy participants with developed dominant follicles.

| Patient ID | Age, years | BMI, kg/m^2 | Grav-ity | Cycle length, days | Dominant follicle | Dim_1 (cm) | Dim_2 (cm) |
|---|---|---|---|---|---|---|---|
| D | 32 | 48.7 | 0 | 28 | Right | 2.22 | 1.85 |
| E | 32 | 35.93 | 2 | 28 | Right | 1.99 | 1.78 |
| F | 32 | 24.51 | 0 | 28 | Right | 2.35 | 1.53 |
| G | 36 | 28.01 | 4 | 28 | Right | 2.1 | 1.36 |
| H | 25 | 27.96 | 0 | 28 | Right | 1.99 | 1.91 |
| I | 35 | 28.3 | 0 | 28 | Left | 1.99 | 1.91 |
| J | 25 | 26.73 | 0 | 27 | Left | 2.66 | 2.26 |
| K | 31 | 19.79 | 1 | 28 | Left | 2.38 | 1.7 |
| L | 30 | 38.4 | 0 | 31 | Left | 1.44 | 1.87 |
| M | 23 | 22.33 | 0 | 28 | Left | 2.38 | 2.08 |
| N | 26 | 26.93 | 0 | 28 | Left | 2.08 | 1.86 |
| O | 24 | 24.2 | 0 | 26 | Left | 2.2 | 2.07 |
| P | 29 | 34.67 | 3 | 27 | Left | 1.81 | 1.24 |
| Q | 33 | 27.64 | 0 | 25 | Left | 1.14 | 2.12 |
| R | 21 | 22.24 | 0 | 27 | Left | 2.24 | 1.81 |

Figures 14A, 14B, 14C:
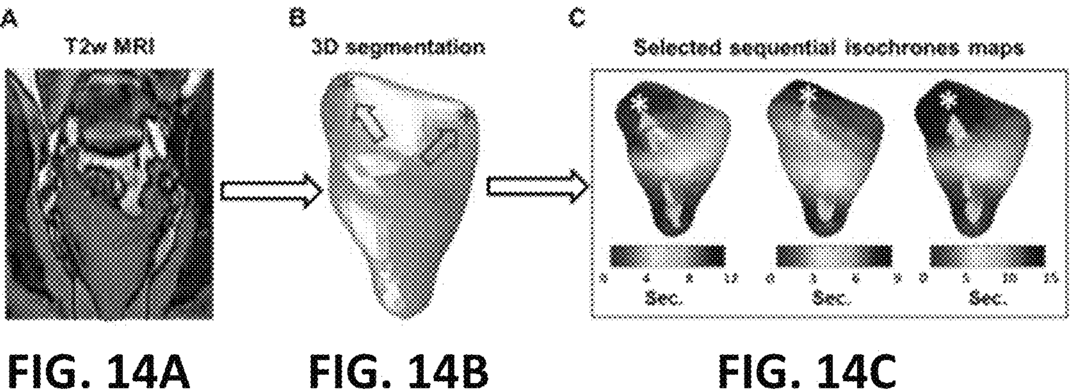
Figures 14D, 14E, 14F, 14G, 14H:
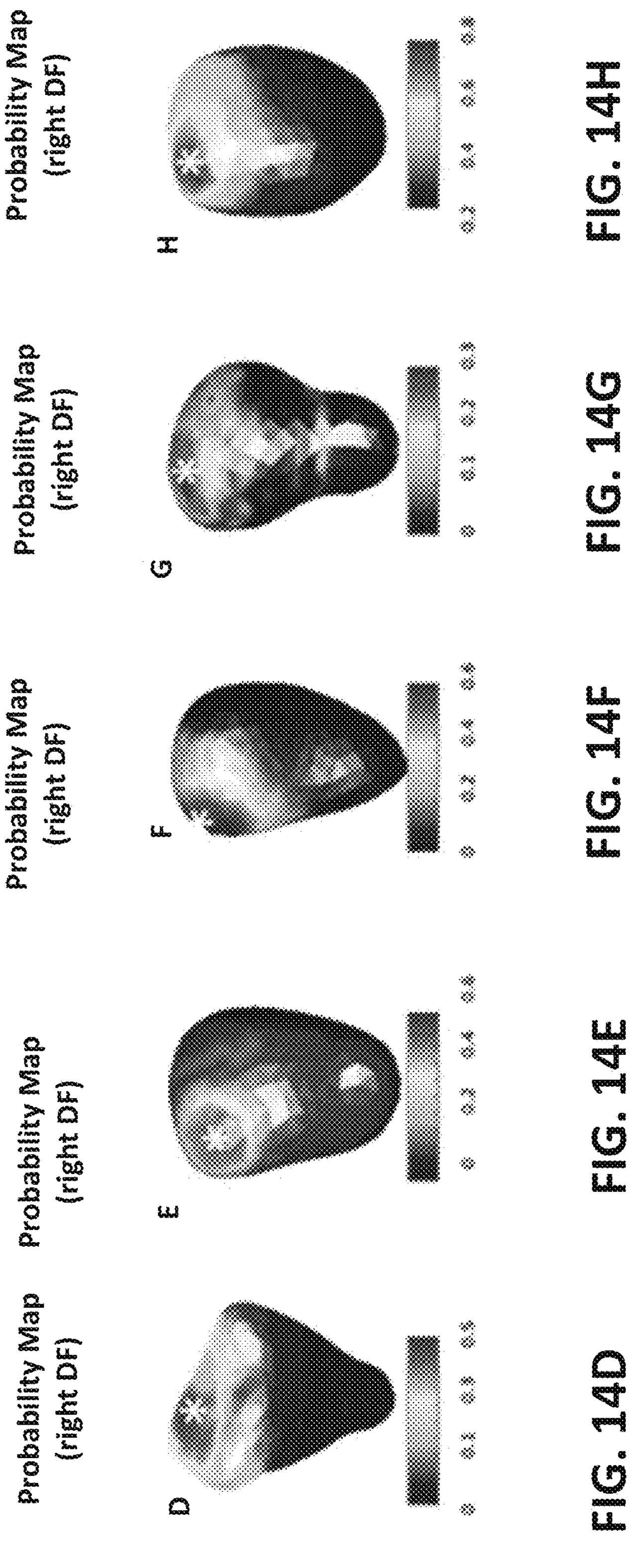
FIGS. 14D-H show termination probability maps of five normal patients (D, E, F, G, H) with a right dominant follicle (DF).
Figures 14I, 14J, 14K, 14L, 14M, 14N, 14O, 14P, 14Q, 14R:
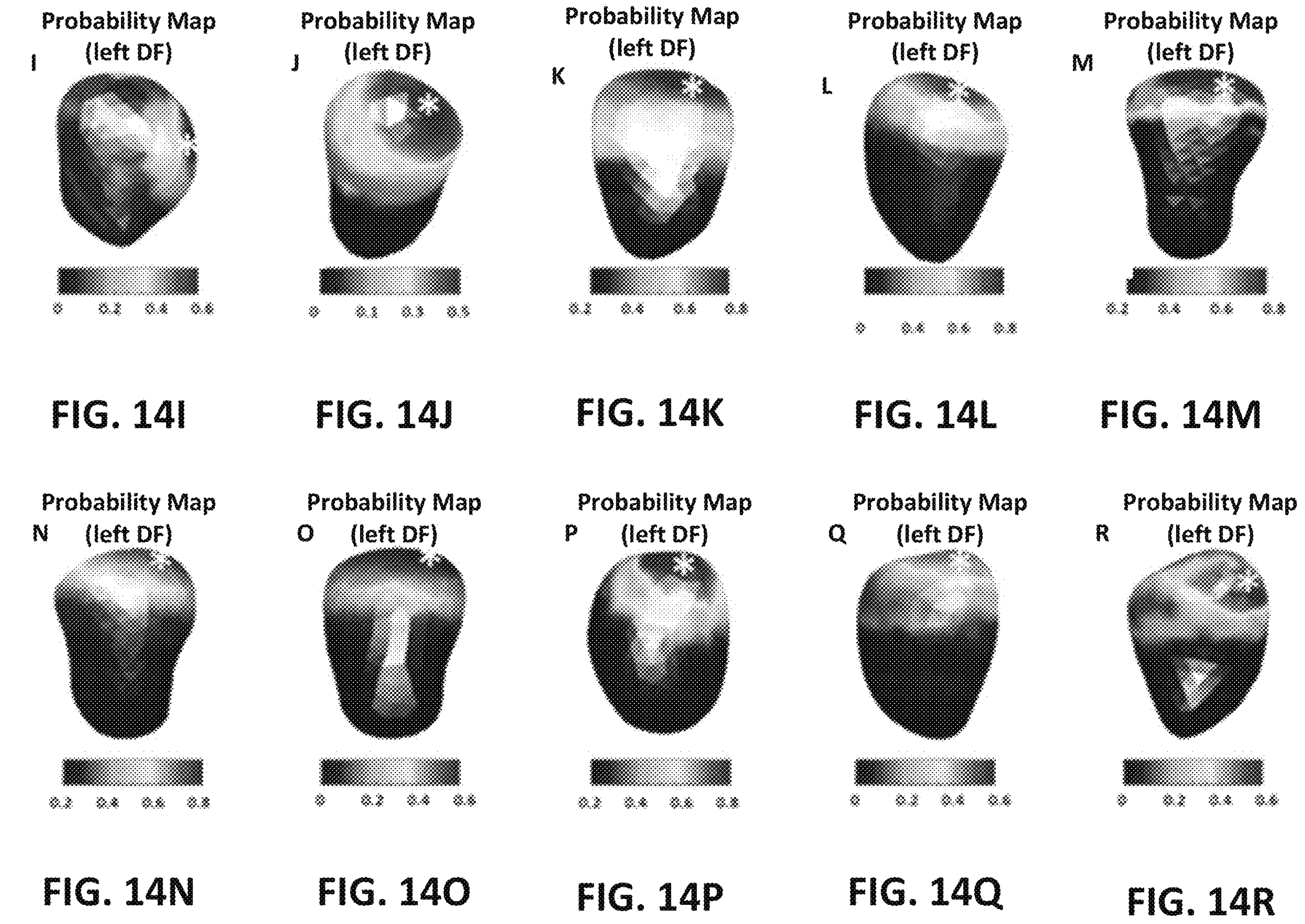

The probability map of termination sites of C-F peristalses serves as a quantitative representation of the destination of sperm transport, influenced by spontaneous mild uterine peristalses. This map holds significant relevance to the interaction between sperm and egg, playing a crucial role in natural fertility. In FIGS. 14A-C, the results from a specific patient with a developed dominant follicle on the right side are presented. FIG. 14A displays a T2-weighted anatomical scan focusing on the pelvic region and reproductive organs. The uterine cavity is depicted in blue, while the two interstitial portions between the fallopian tube and uterine wall are marked by red arrows. In FIG. 14B, the reconstructed 3D uterus geometry with the identified interstitial portions are shown. FIG. 14C illustrates sequential isochrone maps of asymmetric cervix-fundus peristalses, where red indicates the initiation sites and blue indicates the termination sites. Additionally, FIGS. 14D-H exhibit the termination probability map of five healthy participants with developed right-sided dominant follicles, while FIGS. 14I-R display the termination probability map of ten healthy participants with developed left-sided dominant follicles.

The UPI system presented herein can provide objective 4D electrical activation patterns of uterine peristalsis with high spatial-temporal resolution in a noninvasive fashion. In addition to uterine peristalses in predominant directions (Cervix-Fundus and Fundus-Cervix), the system is sensitive to image complex peristaltic wave patterns in accordance with findings in previous TVUS studies. Additionally, novel electrophysiological metrics to quantitatively characterize uterine peristalsis patterns are described herein.

UPI has several major technical advantages over other modalities used to image uterine peristalsis. First, UPI is noninvasive, which is optimal for long-duration uterine monitoring and will not mechanically touch the cervical region and avoid potential alteration of peristalsis like TVUS. Whereas the system allows for continuous recording for a long period of time, researchers using other modalities usually record for 5 minutes and at most 15 minutes. With the wearable electrode sensors, the system can conduct uterine peristalsis imaging for hours or days. Longer recordings will yield more accurate assessment of uterine peristalsis waves and permit identification of more complex wave patterns. Additionally, modalities using invasive monitoring may iatrogenically perturb peristalsis. Second, UPI provides high spatial-temporal resolution and coverage, and the system can characterize the complex pattern of the electrical activation information across the entire uterus including the initiation sites, direction, frequency, and duration of uterine peristalsis waves. Third, UPI provides 4D data that considers the individual's unique uterine-body anatomy and reflects patient-specific uterine peristalsis patterns.

Importantly, 3D spatial probability map of termination sites presented provided new insights into the dynamics of spontaneous uterine peristalsis within its natural environment. During ovulation, the probability map of termination sites in C-F direction provides an intuitive and quantitative tool for understanding the specific locations where sperm transport concludes within the female reproductive system. These termination sites are influenced by the occurrence of spontaneous mild uterine peristalses, which are responsible for facilitating the movement of sperm. The map's significance lies in its direct correlation with the crucial interaction between sperm and egg, thus playing a pivotal role in the context of natural fertility. During menstruation, the probability map of termination sites in Fundus-Cervix direction can be utilized to assess the extent of downwards peristalsis, which is closely associated with the effectiveness of transporting menstrual blood and shedded tissue to the cervix for subsequent expulsion through the vagina. The presence of local inefficient Fundus-Cervix peristalses can lead to the accumulation of shedded endometrial tissues within the uterine cavity, which may increase the risk of developing endometriosis.

The UPI data show that uterine peristalsis patterns quantitatively differ throughout the various phases. In these normal participants, the predominant peristalsis pattern in menses was Fundus-Cervix. Others have seen this pattern in TVUS and postulated that it facilitates the expulsion of menstrual and endometrial tissue while protecting against ascending pathogens. In the peri-ovulatory phase, the predominant peristalsis pattern was Cervix-Fundus. Studies have used serial HSSG to follow labeled macrospheres the size of sperm and observed that they were transported from the cervix into the uterus and fallopian tubes, suggesting that the Cervix-Fundus peristalsis pattern facilitates the transport of sperm toward the oocyte. Bidirectional movement with no predominant pattern in the secretory phase evaluating peristalsis waves was observed at the time of embryo transfers after in-vitro fertilization. No dominant contraction pattern during the proliferative phase was observed.

Definition of Menstrual Phases

Patients were determined to be in one of four menstrual phases (menses, early proliferative, late proliferative, and secretory) by using a combination of patient-reported bleeding, cycle length, ultrasound findings, ovulation predictor kit results, and hormonal measurements. Serum (5-10 ml) was collected and sent to a lab to measure concentrations of estradiol, progesterone, and testosterone. The menses phase was assigned when a patient reported bleeding. The early proliferative phase was assigned after the patient had stopped bleeding, ultrasound demonstrated early follicular activity (largest follicle size <16 mm), serum estradiol <200 μg/ml, and serum progesterone <3 ng/ml. The late proliferative (peri-ovulatory) phase was defined by a positive result on an ovulation predictor kit, serum estradiol >200 μg/ml, serum progesterone <3 ng/ml, and/or a dominant follicle on ultrasound (≥16 mm). The secretory phase was assigned when serum progesterone was >3 ng/ml.

Uterine Peristalsis Imaging (UPI) Procedure

First, a woman underwent a one-time, anatomical (T1W sequence) 3T Siemens Prisma MRI scan (~10 mins) to acquire the patient-specific uterus-body surface geometry while wearing up to 8 patches containing up to 128 MRI-compatible fiducial markers around the abdomen and lower back (FIG. 10A). Uterus and body geometry were generated, electrode locations were identified on the MRI anatomical images (FIGS. 10B-C). Second, customized BioSemi pin-type electrode patches were applied to the same locations on the body surface as the MRI fiducial markers. An ADC box was used to record the body surface electrical signals (FIGS. 10D-E) for 20 minutes. Third, the participant underwent another 10-minute electrical recording while simultaneously undergoing transvaginal ultrasound (TVUS). TVUS scans of the uterus were performed by a sonographer holding the transducer probe while the patient was lying in a lithotomy position. After obaining anatomical images used to inform menstrual phase determination, cine clips were recorded on a GE Voluson S8 ultrasound machine. The duration of each clip was 20 seconds and 30-35 clips were acquired, on average.

Signal Processing

In experiments in which electrical signals were directly measured on the human nonpregnant uterine surface, the median uterine peristalsis frequency was 0.039 Hz in the proliferative phase and 0.020 Hz in the secretory phase. In TVUS and cine MRI studies, the frequency of uterine peristalsis is between 0.33 and 6 contractions per minute throughout the cycle. Therefore, for this experiment a frequency band between 0.01 and 0.05 Hz was selected to minize the high frequency artifacts not correlated with electrical activities of uterine peristalsis. The body surface electrical signals were processed with a band-pass filter to generate wave electrical signals (peristalsis waves) over the entire abdomen surface (FIG. 10F).

Inverse Computation in UPI

With the electro-quasi-static assumption of the bioelectric field, the inverse computation combines the patient-specific uterus-abdomen surface and electrical potentials measured on the abdominal surface to reconstruct the potential distribution over the entire 3D uterine surface. It was assumed that the medium is homogeneous between the uterine surface and abdominal surface without any primary electrical source. Then, the inverse problem could be mathematically described by the Cauchy problem for Laplace's equation (8) with boundary conditions (9,10) on the abdominal surface.

$$\nabla^2 \phi(x) = 0 \tag{8}$$

Dirichlet (9) and Neumann (10) conditions for the abdominal surface potentials are:

$$\phi(x) = \phi_{A(x)},\ x \in \Gamma_A \tag{9}$$

$$\frac{\partial \phi(x)}{\partial n} = 0,\ x \in \Gamma_A \tag{10}$$

Here, n is the normal vector on the abdominal surface at location x and $\Gamma_A$ represents abdominal surface. $\phi_{A(x)}$ is the potential measured on the abdominal surface and $\phi(x)$ is the potential on the uterine surface.

As a mesh-free method robust to noise, a method of fundamental solutions (MFS) was deployed to discretize the Laplace's equation and boundary conditions, which is accurate for solving the bioelectric field inverse problem in both electrocardiographic imaging and electromyometrial imaging (EMMI) systems. This problem cannot be solved directly as it is an ill-posed inverse problem. Therefore, Tikhonov-based inverse computation with a fixed regularization value of 0.01 was used to obtain the solution.

$$\Phi_A = A\,\Phi_U \tag{11}$$

Here, $\Phi_A$ is a M*T matrix of measuring surface potentials, $\Phi_U$ is a N*T matrix of uterine surface potentials, where M is the number of measuring electrodes applied on the abdominal surface and N is the number of discrete points on the uterine surface, and T is the number of recording time points. A is a M*N linear transform matrix encoding the relationship between abdominal surface potential $\Phi_A$ and uterine surface potential $\Phi_U$.

UPI Data Processing

The inverse computation described above was employed to compute the uterine surface electrical signals (FIG. 10G-H) on the three-dimensional uterine surface. The times when the uterine surface electrical signals at various uterine surface areas reached the steepest negative slope were extracted and defined as electrical activation times at those uterine areas during peristalsis waves (red dots in FIG. 10G-H). During each peristalsis wave, sequential time frames were generated as the activation sequences (FIG. 10I) to reflect the detailed 4D spatial-temporal activation patterns of the uterine peristalsis. Within each time frame, the red region indicated the electrically activated myometrium areas currently experiencing peristalsis, and the blue region indicated the inactive areas of the uterus. The isochrone map was generated as a color-coded 3D map to summarize the electrical activation sequence (FIG. 10I). In the isochrone map, warm and cool colors denote regions of the uterus that activated early and late, respectively, during the peristalsis wave.

Inspection of Uterine Peristalsis Direction

Uterine peristalsis direction was categorized according to the wave classification system illustrated in Table 4. A customized UPI post-analysis software with graphical user interface (GUI) was developed in MATLAB (R2021b) to visualize each peristaltic wave. The software first detected the uterine peristalsis waves according to the electrical activations and recorded the start and end times. Next, five independent observers visually inspected the electrical activation sequences and isochrone maps to define the direction, initiation, and termination sites of each uterine peristalsis wave. Two observers (A, B) had been intensively involved in research on ultrasound and MRI of nonpregnant uterus and are familiar with the topic. The other three observers (C, D, E) were biomedical engineers. All observers received the same instructions on how to assess the endometrial waves. All UPI activation movies were masked for patients' name, demographics, OBGYN history, and menstrual phase. All UPI videos were independently inspected by observers C, D, and E. If the observers disagreed on the direction or initiation or termination site of a uterine wave, A and B examined the movie and made the final call. Next, the software automatically calculated the duration, magnitude, and power of each uterine peristalsis wave. Finally, statistical analysis of the uterine peristalsis wave frequency, direction ratio, and mean value of duration, magnitude, and power was performed.

TABLE 4

Endometrial wave classification system.

| Wave type | Wave symbol | Definition |
|---|---|---|
| Cervix-Fundus | C-F | Wave propagates from cervix to fundus |
| Fundus-Cervix | F-C | Wave propagates from fundus to cervix |
| Others | Alternating | Wave propagates from cervix to fundus with an alternating wave from fundus to cervix |
| | Recoiling | Wave propagates from cervix to fundus followed by a reflective wave toward cervix |
| | Standing | Visible wave with no propagation toward cervix or fundus |
| | Opposing | Wave start at cervical and fundal uterine regions simultaneously |
| | Random | Waves start at multiple sites on the uterus |

Inspection of TVUS Images

Three registered sonographers independently (without knowledge of the UPI results) examined the TVUS recordings to determine the uterine peristalsis direction. These sonographers were specialized in the field of OBGYN, with experience in watching TVUS images. One of them had previously performed visual inspection of contractions for research.

Electrophysiological Characterization and Quantification

Three UPI electrophysiological indices were defined to qualitatively and quantitatively describe uteirne peristalsis patterns. Duration (Sec.) was defined as the duration of a complete peristalsis wave measured in the isochrone map (FIG. 11A) of the uterine peristalsis wave. Magnitude (mV) was defined as the average peak amplitude of electrical potential over the uterine region experiencing activation during the entire peristalsis wave. Magnitude map (FIG. 11B) was developed to present the magnitude distribution over the entire 3D uterine surface in one peristalsis. Power (mV*sec) was defined as the product of magnitude and duration for each uterine peristalsis wave.

Spatial and Temporal Analysis of Human Uterine Peristalsis

Frequency was determined by counting the number of uterine peristalses detected during the recording session and dividing it by the total imaging time. To analyze the compositions of uterine peristalsis propagation direction, initiation, and termination sites (FIGS. 11C-E), the number of peristalsis waves with specific propagation directions (Fundus-Cervix, Cervix-Fundus, or other) and initiation and termination sites (cervical, fundal, or other regions) were calculated. These counts were then divided by the total number of peristalsis waves observed during the 30-minute electrical mapping session.

The direction ratio (FIG. 11C) represents the percentage of peristalses occurring in each direction out of the total number of peristalses observed. Initiation and termination sites were identified as the regions where uterine peristalsis first started and ended, respectively, based on the activation sequences. These sites were categorized into three groups: Cervical region, Fundal region, and Other regions. The initiation and termination site compositions (FIGS. 11D-E) denotes the percentage of peristalses initiated (terminated) in each uterine region (cervical, fundal, or other region) throughout the entire recording.

To determine the initiation (termination) probability for each point in each direction, the relative frequency measurement (ranging from 0 to 1) by dividing the number of peristalses initiated (terminated) at a specific point by the total number of peristalses in that direction during the imaging session was calculated. This allowed generation of spatial probability maps of initiation (termination) sites (FIGS. 11F-G) on the uterine surface accordingly.

Statistical Analysis

Baseline demographic and OBGYN history characteristics of patients were summarized by using frequencies and percentages for categorical variables and means (95% confidence interval) for OBGYN history, ovarian follicles, and hormone measurements.

The primary outcomes of each uterine peristalsis wave were one qualitative variable (direction) and three quantitative variables: duration (sec), magnitude (mV), and power (mV*sec). UPI-indexed parameters were calculated according to directions (C-F, F-C, and others) using the mean value of UPI measurements for each patient in each visit within the standard 30-min time window. Kruskal-Wallis test was performed to analyze the difference of each UPI parameter between menstrual cycle phases. $P<0.05$ was considered statistically significant.

Example 2

This example was conducted to study the effect of transvaginal ultrasound (TVUS) on uterine peristalsis patterns in non-pregnant patients. The experiment was a prospective observational cohort study evaluating a non-invasive uterine peristalsis imaging (UPI) system. Electrode patches are placed on the patient's abdomen after assessing uterine anatomy. UPI quantifies the 3D electrical activation pattern during uterine peristalsis to calculate peristalsis frequency, duration, magnitude, and activation ratio. A 20-minute UPI scan was completed prior to TVUS followed by a 10-minute UPI scan acquired simultaneously during TVUS exam as a comparison. 22 patients with regular menstrual cycles, not taking hormonal medication, and without known gynecologic pathology were included in the analysis. Subjects were imaged longitudinally during the four phases of the menstrual cycle (menses, proliferative, peri-ovulatory, secretory) with UPI scan followed by concurrent TVUS and UPI scan. Hormone levels (estradiol and progesterone) and a TVUS evaluating follicular development were obtained during each visit to confirm phase of menstrual cycle.

Duration, frequency, magnitude, and activation ratio of the uterine peristalsis waves were compared pre and post TVUS. Uterine peristalsis was altered by the performance of TVUS. With use of simultaneous TVUS, uterine peristalsis waves had a change in at least one of the outcomes measured in 55.7% of all visits. Magnitude was significantly higher with TVUS use in all phases of the menstrual cycle. TVUS use increased the frequency of peristalsis waves in all phases except the proliferative phase. Duration of peristalsis waves and the activation ratio were higher with TVUS in all phases except the secretory phase. This work demonstrates that TVUS may inherently affect uterine peristalsis waves. This finding supports that non-invasive technology, such as the UPI system, can more accurately measure physiologic peristalsis waves.

Ultrasound technology uses high-frequency sound pulses to create images and has been a staple in obstetrics and gynecology for many decades. Various forms of ultrasound are utilized today. Sonograms are part of most facets of gynecologic care including to monitor pregnancies, to diagnose pathology, and to perform assisted reproductive technology (ART) procedures such as oocyte retrievals and embryo transfers. Although large epidemiological studies of ultrasound safety are lacking, they have been used for over 60 years without any obvious harmful effects reported in humans. However, biological effects, especially at a tissue/organ level, have not been well-studied.

Uterine peristalsis (UP) waves are a possible biological effect that ultrasound may alter in gynecologic patients. Studies have documented spontaneous, mild peristalsis waves from the inner layer of the myometrium (stratum subvasculare) which is distinct from labor contractions occurring at all layers of the myometrium. Although the uterus is quiescent in the pre-pubertal and menopausal stages, peristalsis waves are vital and dynamic during the reproductive lifespan, specifically during the four phases of the menstrual cycle. Imaging studies utilizing ultrasound and intrauterine pressure catheters have provided evidence that the pattern, direction, and frequency of these contractions vary throughout the phases of the menstrual cycle. Given that uterine peristalsis waves cyclically change, if transvaginal ultrasound can inherently affect peristalsis was examined.

To study this possible effect, electromyometrial imaging to longitudinally calculate uterine peristalsis waves was utilized. The uterine peristalsis imaging (UPI) system measures myometrial electrical activity quantitatively and objectively in a non-invasive manner. The UPI system combines an MRI scan to determine body-uterus geometry and body surface electrodes to determine body surface potential placed into a software system to provide reconstructed uterine surface potentials. MRI alone has been used to study peristalsis waves because it is non-invasive, however, it cannot detect magnitude of waves and is not scalable. A technique evaluating the gravis uterus was previously described by our group using EMMI on pregnant patients. The reconstructed uterine surface potentials quantitatively image and measure 3D electrophysiological activities of uterine contractions non-invasively and, therefore should not alter peristalsis waves. Here, the effect of transvaginal ultrasound on uterine peristalsis waves was analyzed by utilizing the non-invasive UPI system.

Patient Enrollment and Human Study

Nonpregnant patients between ages 18 to 37 years old with regular menstrual cycles every 24-35 days were enrolled in the study. Patients who were post-menopausal, pregnant or breastfeeding; had a uterine anomaly; or had an exposure to medications known to affect uterine contractility (i.e., magnesium, opioids, beta antagonists, nifedipine) were excluded from this study. In addition, patients whose abdominal circumference was greater than 55 cm or had MRI contraindications (pacemaker, metal implants, etc.) were excluded from this study as well. Twenty four eligible patients were enrolled into this study after signing an informed consent. Each patient was imaged during the four phases of the menstrual cycle (menses, proliferative, peri-ovulatory, and secretory).

Patient-reported bleeding, cycle duration, ultrasound findings, ovulation prediction kit data, and hormone measurements were used to identify accurately the phase of the menstrual cycles. The menses phase was assigned when the patient reported bleeding. After the patient's bleeding had ceased, proliferative phase was defined by early follicular activity on TVUS (largest follicle size <16 mm), estrogen level <200 pg/ml, and progesterone level <3 ng/ml. The peri-ovulatory phase was defined by a positive ovulation predictor kit, estradiol level >200 pg/ml, progesterone level <3 ng/ml, and/or a dominant follicle on ultrasound (>=16 mm). The secretory phase was assigned when progesterone levels were greater than 3 ng/ml. Occasionally, the projected phase based on their cycle was different than the phase verified by hormone levels and TVUS. In those instances, additional visits were performed based on patient availability.

MRI Scan

The subject underwent a one-time, quick, anatomical (T1W sequence) 3T Siemens Prisma/Vida MRI scan (FIGS. 15A-B) to acquire the patient's unique body-uterus geometry (FIG. 15C), while wearing 8 patches containing 128 MRI-compatible fiducial markers around the abdomen and lower back.

Electrical Recording

Figure 15:
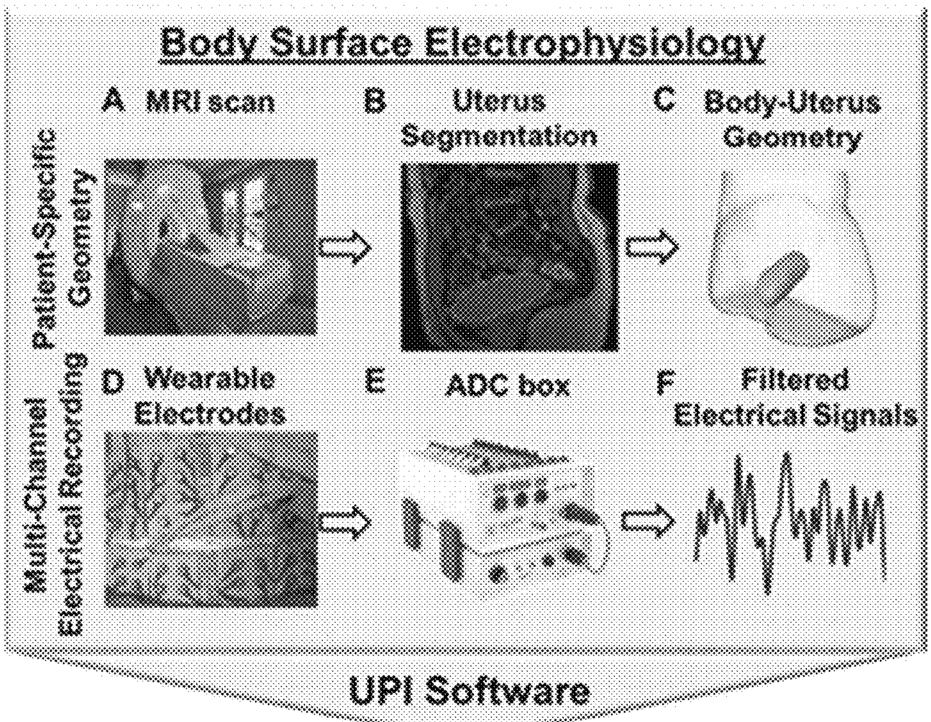
FIGS. 15A-J show a uterine peristalsis imaging (UPI) system with automatic peristalsis detection and multi-parametric quantification.
Figure 15:
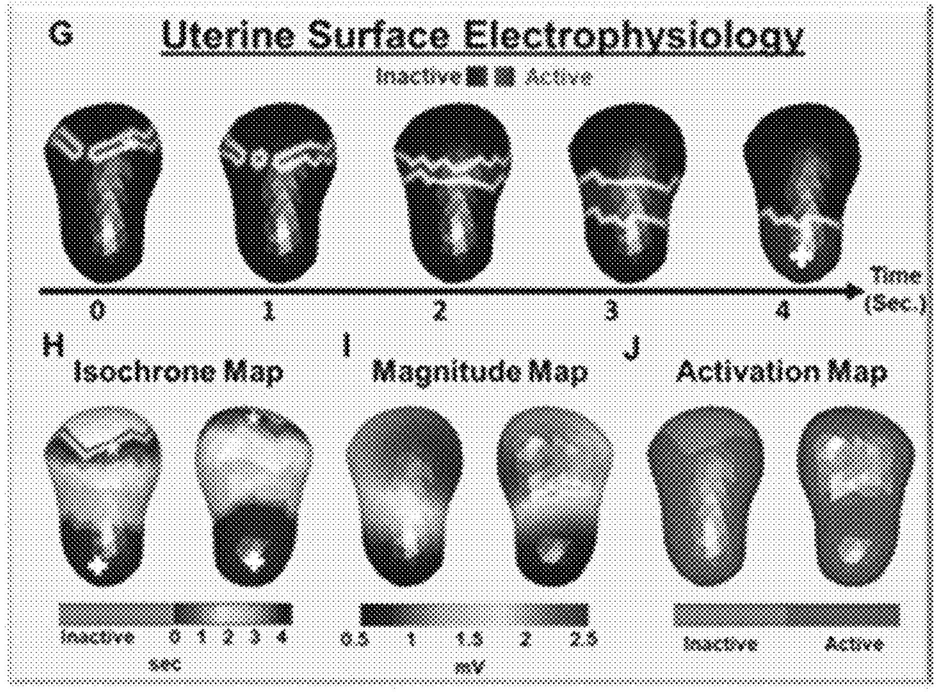

After the MRI scan, customized BioSemi pin-type electrode patches (FIG. 15D) were applied to the same location on the body surface as the MRI fiducial marker patches and an BioSemi ADC box was used to record the body surface electrical signals (FIG. 15E). Then, the multi-channel electromyography (EMG) signals were processed with a band-pass filter (0.01-0.05 Hz) (FIG. 15F). In each clinical visit, two EMG recording sessions were performed. In the first session, a 20-min UPI scan was acquired without TVUS as a control. Next, a 10-min UPI scan was acquired with a simultaneous TVUS exam as a comparison.

TVUS Scan

A GE Voluson E6 ultrasound machine was used to evaluate uterus including measurement of the endometrial stripe and the ovaries including follicular measurement. This 10-minute scan occurred synchronously with the UPI system.

Inverse Computation

The UPI software was developed to solve the three-dimensional Cauchy problem to formulate the uterine electrograms as electrical activities over time at each uterine site. Uterine surface EMGs specifically reflect the uterine surface electrical activities during UP. By identifying the time when the uterine EMGs reach the steepest negative slope, electrical activation sequence of the myometrium during a specific observation window was formed (FIG. 15G), where red regions represent areas experiencing the peristalsis and blue regions represent inactive areas of the uterus.

Multi-Parametric Quantifications of Uterine Peristalsis

The UPI post-analysis software was developed to quantify each peristalsis and generate the statistical UP report of each mapping session for each patient. An isochrone map (FIG. 15H) was formed based on the activation sequence, where gray colors denote the inactive uterine regions, red and blue colors denote the early and late activation uterine regions, respectively, during peristalsis. Initiation sites were defined as the region experiencing the early activation during UP. Termination sites were defined as the region experiencing late activation. The anatomy of the initiation and termination sites were identified on the isochrone map, and included the cervical region, fundal region, left/right cornual region, and middle of the uterus as well as other areas.

UP quantifications used include duration (sec), magnitude (mV), frequency (/min), and activation ratio (%) for each peristalsis. UP duration was defined as the duration of a complete UP measured from start of the wave until end of this peristalsis. Shorter duration indicated that the UP was more synchronized. As shown in FIG. 15I, UP magnitude was defined as the average peak amplitude of electrical potential over the uterine region experiencing activation during each UP. UP frequency (/min) was calculated as the number of peristalses over the imaging time (in minutes). As shown in FIG. 15J, activation ratio was defined as the percentage of cumulative electrically activated area (decoded in red) over the entire uterine surface in each peristalsis. For example, 50% means the peristalsis wave activated 50% of the entire uterine surface.

Statistical Analysis

Numeric variables among patients who participated in the study were summarized using mean and standard deviation. Categorical variables were summarized using frequencies and percentages.

Figure 16:
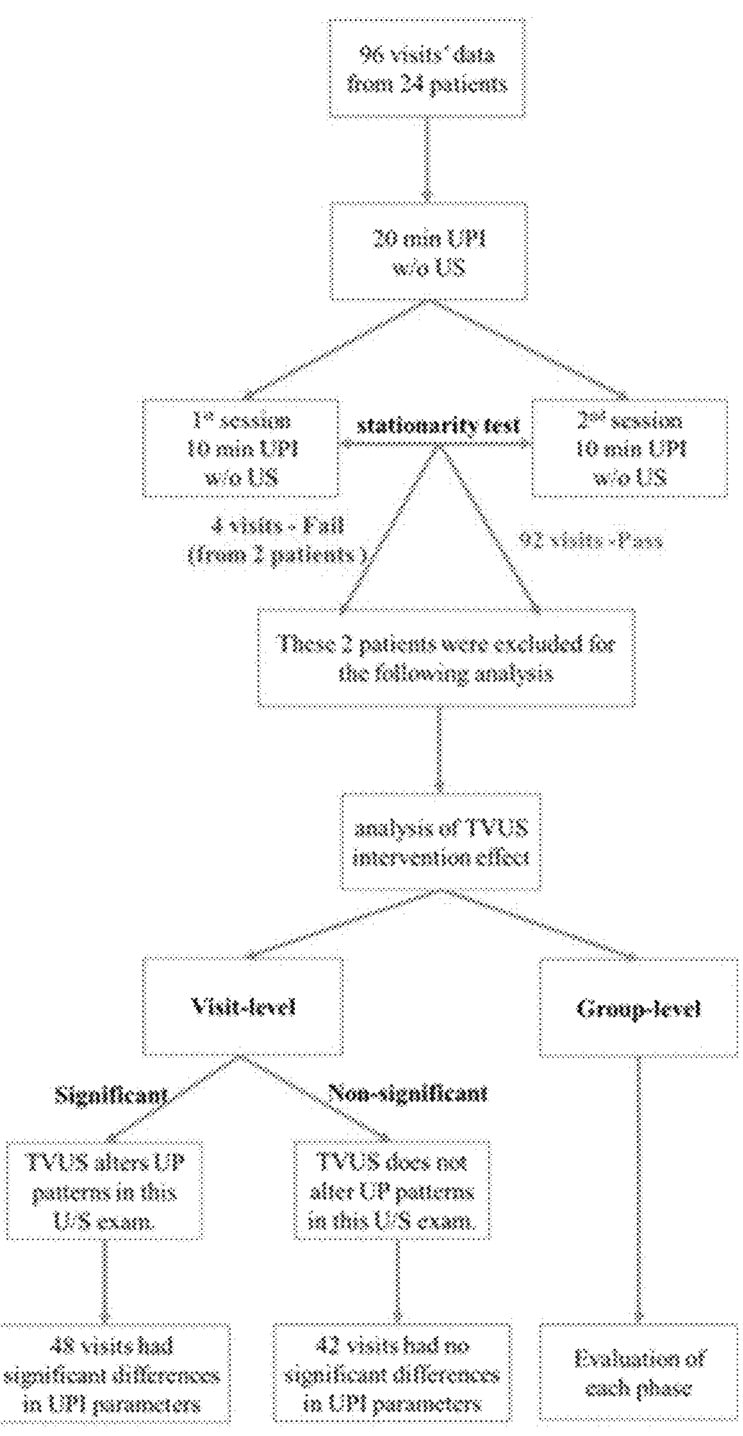
FIG. 16 shows an analysis flowchart to determine stationarity test.

FIG. 16 illustrates an analysis flowchart to determine a stationarity test. The primary outcomes of each uterine peristalsis were quantitative variables including duration (sec), magnitude (mV), frequency (#/min), and activation ratio (%). The first 20 mins electrical mapping session without TVUS was divided into two 10-min segments to test the stationarity of UP measurements. Mann-Whitney U-test was performed to determine if there is significant difference of each UPI parameter between two segments, and p-value $<0.05$ is considered as statistically significant. If at least one UPI-indexed variable was identified as significantly different between two periods, the UPI measurement would be considered as a nonstationary process. This visit would be designated as a failed visit. If no significant difference was found between two segments, the UP measurements were considered as stable and the stationarity tested was passed. Only visits with a passed stationarity test were included in analysis.

Analysis of TVUS Intervention

At the visit level, the outcome of the following 10-min electrical mapping with TVUS would be compared with the second 10-min segment without TVUS to analyze the difference using the Mann-Whitney U-test. If one UPI-indexed variable was identified as significantly different, then it was believed that TVUS interventions alter the UP patterns. At the group level, Wilcoxon matched-pairs signed-ranks test was performed to compare each averaged UPI-indexed variable of matched visits before and during ultrasound exams.

Results

Ninety-six visits were completed in 24 normal patients with regular menstrual cycles. As noted above there were four visits confined to two patients which failed the stationarity test. Given that 22 out of 24 patients passed all four visits and only 2 patients failed the stationarity test, the decision was made to exclude all visits for both patients. Table 5 demonstrates demographic data and menstrual cycle history in all completed patients by phase of cycle.

TABLE 5

| Demographics of enrolled patients (N = 24) with regular menstrual | |
|---|---|
| Age, years | 27.5 +/- 4.7 |
| BMI, kg/m^2 | 30.4 +/- 8.7 |
| Race, n(%) | |
| White | 12 (50%) |
| Black | 9 (38%) |
| Asian | 2 (8%) |
| Other | 1 (4%) |
| Cycle length, days | 28 +/- 2 |
| Length of bleeding, n (%) | |
| 3-5 days | 14 (58%) |
| 6-7 days | 6 (25%) |
| Unknown | 4 (17%) |

| Phase | | | |
|---|---|---|---|
| Menses (n = 17) | Proliferative (n = 12) | Ovulatory (n = 12) | Secretory (n = 23) |

TABLE 5-continued

| Demographics of enrolled patients (N = 24) with regular menstrual | | | | |
|---|---|---|---|---|
| Estradiol (pg/mL) | 33.7 +/− 17.4 | 93.9 +/− 44.8 | 156.0 +/− 95.4 | 120.0 +/− 50.1 |
| Progesterone (ng/mL) | 0.8 +/− 2.3 | 0.2 +/− 0.01 | 2 +/− 2.1 | 8.2 +/− 4.7 |
| Endometrial thickness (mm) | 3.7 +/− 0.3 | 6.4 +/− 1.9 | 9.5 +/− 3.1 | 9.7 +/− 3.0 |

Figures 17I, 17J, 17K, 17L:
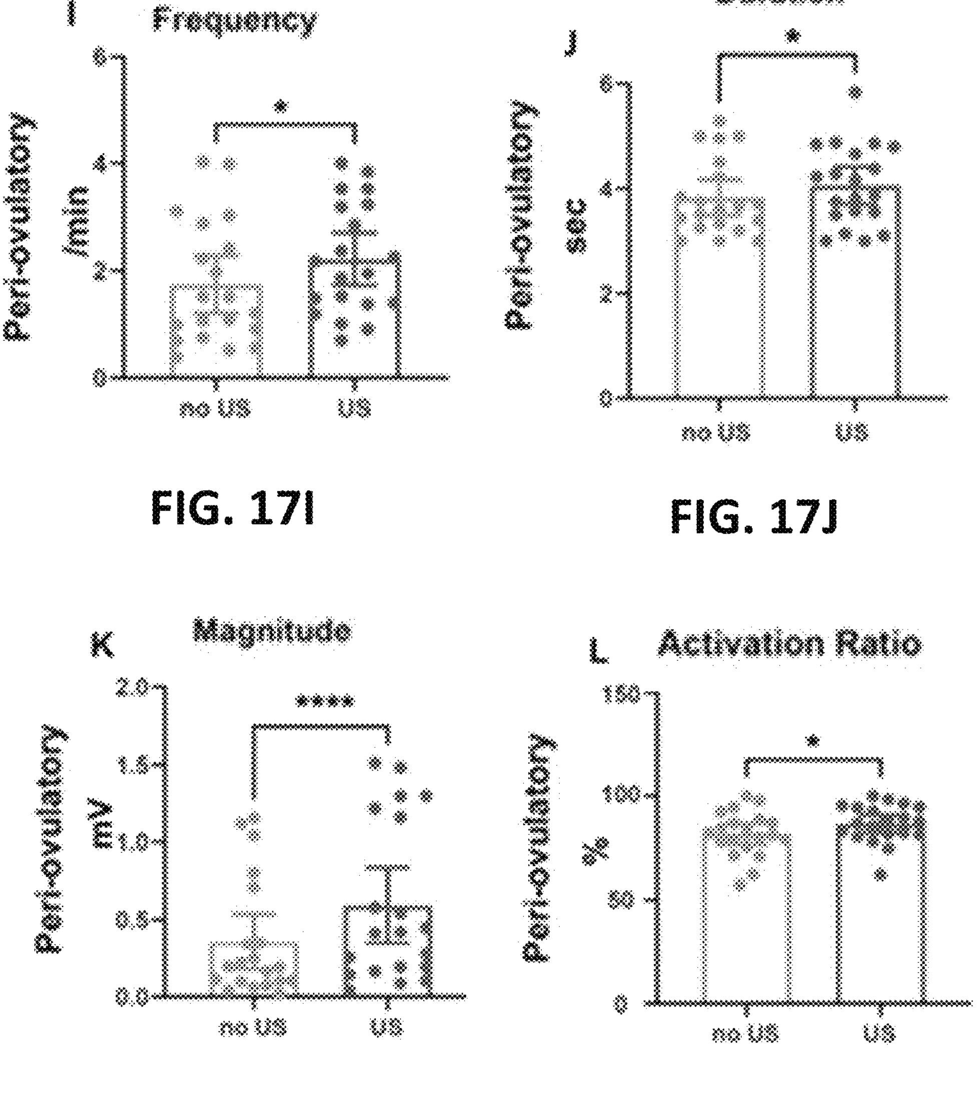
FIG. 17I shows frequency of peristalsis waves with TVUS and without TVUS during the peri-ovulatory phase.
FIG. 17J shows duration of peristalsis waves with TVUS and without TVUS during the peri-ovulatory phase.
FIG. 17K shows magnitude of peristalsis waves with TVUS and without TVUS during the peri-ovulatory phase.
FIG. 17L shows activation ratio of peristalsis waves with TVUS and without TVUS during the peri-ovulatory phase.
Figure 17M:
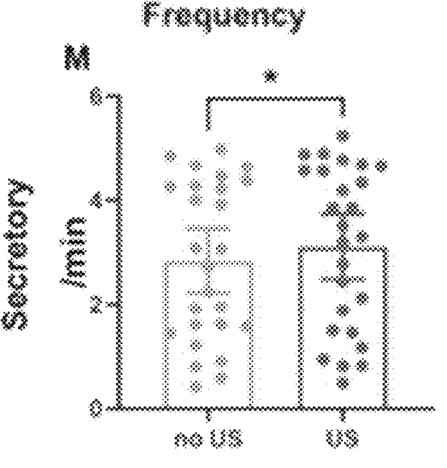
FIG. 17M shows frequency of peristalsis waves with TVUS and without TVUS during the secretory phase.
Figure 17N:
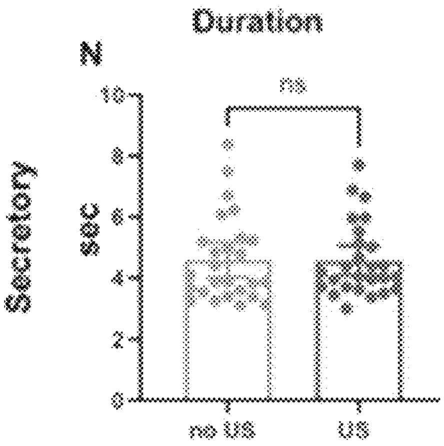
FIG. 17N shows duration of peristalsis waves with TVUS and without TVUS during the secretory phase.
Figure 17O:
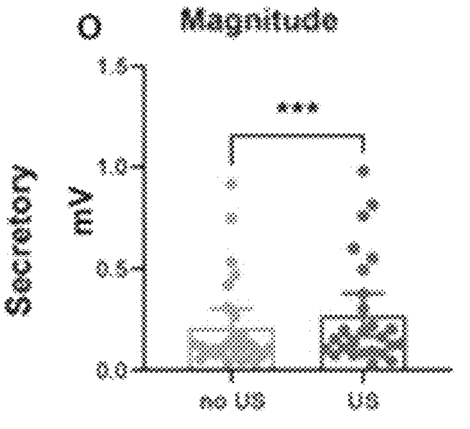
FIG. 17O shows magnitude of peristalsis waves with TVUS and without TVUS during the secretory phase.
Figure 17P:
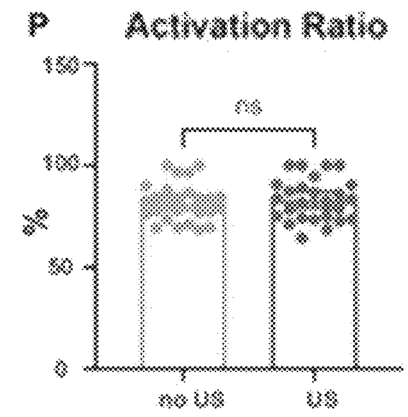

A total of 88 visits were included in analysis. Group level analysis is demonstrated in FIGS. 17A-P. In all phases but the proliferative phase, the frequency of peristalsis waves (measured in waves/min) was significantly higher after TVUS use. The duration of peristalsis waves (measured in seconds) was significantly greater with TVUS use in all phases except the secretory phase. In all phases, the magnitude of peristalsis waves (measured in mV) was significantly higher. Finally, the activation ratio (measured as a percentage) was significantly higher in all phases except for the secretory phase.

The data demonstrate that uterine peristalsis waves are altered by the introduction of a transvaginal ultrasound probe. Peristalsis waves had a significant increase in magnitude during every phase of the menstrual cycle and frequency, duration and activation ratio significantly increased in three of the four phases. The results suggest a quantitative difference in peristalsis waves for patients undergoing a TVUS.

Traditional 2D TVUS has been used for decades to image uterine peristalsis waves and newer technology including 4D imaging and the speckle tracking have now been introduced to further characterize these waves. Unfortunately, TVUS is only used for short time frames (typically 4 to 15 minutes) due to its invasive nature making it not capable of performing long-term comprehensive analysis. While US technology is considered easily reproducible and objective without obvious harmful effects, there are few studies that evaluate potential biological effects from the equipment itself. This is the first study to evaluate if TVUS may inherently affect uterine peristalsis waves which is important to determine if it is an ideal imaging modality to quantify uterine peristalsis. Given that over 50% of visits had a change in peristalsis waves before and during TVUS probe placement, a non-invasive system could better quantify these waves without causing iatrogenic changes. The UPI system can create reconstructed uterine surface potentials to quantitatively image and measure 3D electrophysiological activities of uterine peristalsis waves non-invasively without inducing changes.

Ultrasound uses energy in the form of sound waves that are transmitted into the body, and waves echoed back are recorded to produce an image. Both thermal and non-thermal effects could explain the changes seen with TVUS use. Sound waves can be converted into heat and this process has clinical application for procedures such as ablations, however, it can also occur unintentionally with transducers. Thermal effects have been raised as a concern with Doppler TVUS in early pregnancy because of its potential impact on organogenesis. However, temperature increases less than 2 degrees C., even for prolonged periods, have not been shown to have a biological effect outside of obstetrical ultrasounds, and, additionally, no Doppler was used during this study. Use of a transvaginal probe causes direct pressure on the cervix and indirect pressure on the uterus creating mechanical (non-thermal) effects. This is more likely to explain peristalsis changes given that postpartum uterine massage is well-documented to cause contractions. The mechanism of action for uterine massage in an obstetrical setting is postulated to be the release of prostaglandins causing uterine contractions. To a lesser extent, a similar mechanism may be occurring in gynecologic patients undergoing TVUS.

The results presented here also demonstrate that TVUS affects peristalsis waves differently at different phases. Overall, the number of visits affected decreased from menses to the secretory phase from 72.7% to 38.5% visits affected, respectively. Hormonal fluctuations throughout the menstrual cycle, including not only steroid hormones but also peptide hormones and prostaglandins, likely contribute to this pattern. For example, the steady rise in oxytocin and estrogen in the pre-ovulatory follicles during the proliferative phase is thought to increase frequency of peristalsis waves, which was seen from menses to proliferative phases. Interestingly, no significant change in frequency of peristalsis waves at a group level before and during US use was seen. Because patients could have been early, mid, or late in the phase, there may have been too much variability to see any significant difference in frequency. Also, after ovulation during the secretory phase, progesterone, a known muscle relaxant, rises then falls late in the phase prior to menses and contributes to changes in peristalsis waves by having an antagonist effect on estrogen and oxytocin receptors. Again, given the patients had visits during different times during the secretory phase with different progesterone levels, the variability may cause a lack of group difference seen in the duration and activation ratios before and during TVUS.

In summary, data collected through use of the UPI system has demonstrated that TVUS can alter uterine peristalsis waves in gynecologic patients with normal menstrual cycles. Changes include alterations in peristalsis frequency, duration, magnitude, power, and activation ratio. This example shows that a non-invasive imaging modality, such as the UPI system, would better evaluate peristalsis waves to avoid iatrogenic changes.

Example 3

Human uterine activity changes dynamically across the menstrual cycle. Menses begins when serum concentrations of the hormones progesterone and estrogen drop, signaling the uterus to shed blood and epithelial cells through the cervix. In the proliferative phase, the uterine epithelium grows in thickness to prepare for potential embryo implantation as a follicle develops on one or both ovaries to release an oocyte. During the peri-ovulatory phase, an oocyte is released and travels down the fallopian tube. If unprotected sexual intercourse occurs during this time, fertilization may occur. During the secretory phase, the uterine epithelium continues to thicken in preparation for potential embryo implantation.

Most research on the menstrual cycle has focused on hormones and their effects on the epithelium. However, some evidence indicates that the smooth muscle layer, the myometrium, also contributes to uterine functions by generating slow, low-magnitude, spontaneous contractions, termed uterine peristalsis. Unlike labor contractions, in which the entire myometrium produces faster and stronger contractions, uterine peristalsis only involves the inner layer of the myometrium, the stratum subvasculare. Uterine peristalsis, first observed on ultrasound, has been shown to vary in direction and frequency throughout the phases of the menstrual cycle. During menses, peristalsis waves travel from the fundus to the cervix and help expel blood and tissue. Conversely, peristalsis waves travel from the cervix toward the fundus during the peri-ovulatory phase and help transport sperm toward the fallopian tubes.

Several studies have suggested that uterine peristalsis plays an essential role in uterine pathology. Disruptions in uterine peristalsis may occur in women who experience infertility, dysmenorrhea, and endometriosis, a painful condition in which cells from the uterine epithelium implant and grow outside of the uterus, commonly in the peritoneal space. In addition to causing chronic pelvic pain, endometriosis may also cause dysmenorrhea, irregular bleeding, and subfertility. Evidence that disrupted uterine peristalsis contributes to endometriosis comes from studies using ultrasound and intrauterine pressure catheters. These studies demonstrated that patients with endometriosis had dysperistalsis and higher uterine tone, and more frequent Cervix-Fundus contractions than normal women.

Although previous studies provided measurements of uterine peristalsis, the available data have been limited by the capabilities of the four main technologies used to assess uterine peristalsis. First, intrauterine pressure catheters are invasive, and a catheter placed inside the uterus could alter peristalsis patterns. Second, transvaginal ultrasound (TVUS) is invasive and is not sensitive enough to identify the site of peristalsis initiation. Additionally, the quality of TVUS measurement depends on the orientation of the ultrasound transducer, making this method highly subjective and operator- and time-dependent. Third, hysterosalpingography (HSSG) is a procedure in which X-rays are used to detect a radiographic contrast dye injected into the uterus and fallopian tubes. Although HSSG measures are objective, HSSG cannot be used to measure peristalsis amplitude or frequency, and radiation exposure limits the imaging time. Fourth, cine magnetic resonance imaging (MRI) can be used to detect uterine peristalsis by acquiring sequential images for an extended period of time and playing the MRI frames 12 times faster than the actual speed. However, extended cine MRI is expensive, time-consuming, and operator-dependent, and it cannot reveal the initiation and termination sites of uterine peristalsis. Moreover, all of the above modalities can be uncomfortable for the participant and cannot be used for long-term observation.

The electrophysiological imaging system called Electromyometrial Imaging (EMMI) was developed to quantitatively measure the electrical activity underlying uterine contractions during labor. Here, this system was adapted to longitudinally image the 4-dimensional (4D) electrical waves of uterine peristalsis over each phase of the menstrual cycle in healthy, nonpregnant participants with normal menstrual cycles and in participants with endometriosis. With this uterine peristalsis imaging (UPI) system, human uterine peristalsis can be imaged in a safe, comfortable, and accurate way. UPI can provide precise quantitative electrophysiological evidence that uterine peristalsis changes in frequency, direction, duration, magnitude, and power throughout the menstrual cycle and is disrupted in endometriosis patients.

Uterine Peristalsis Imaging (UPI) System

Figure 18:
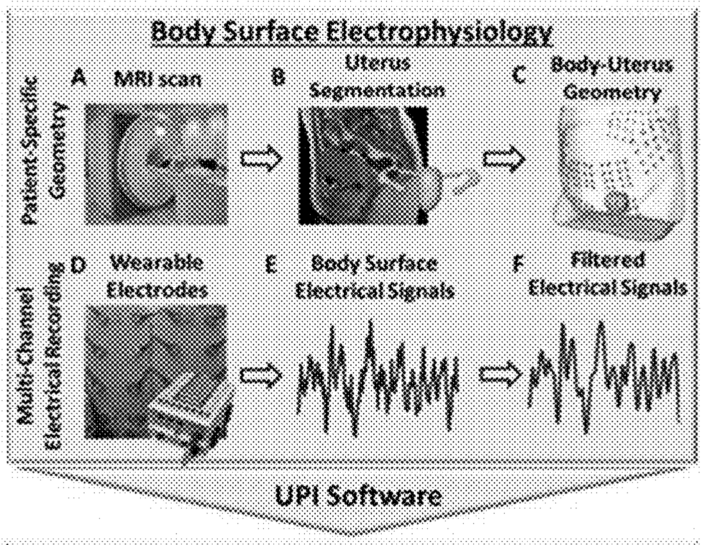
FIGS. 18A-L show a schematic of uterine peristalsis imaging.
Figure 18:
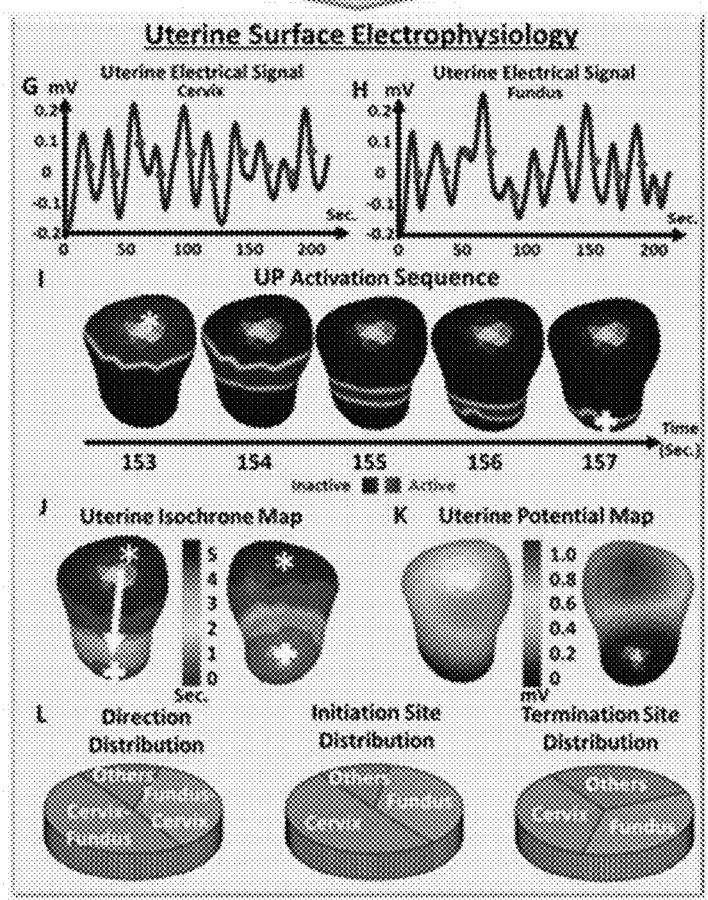

The uterine peristalsis imaging (UPI) system is further developed based on the EMMI system and is illustrated in FIG. 18A-L. First, a woman underwent a one-time, fast, anatomical MRI scan (FIG. 18A) to acquire the patient-specific uterus-body surface geometry (FIGS. 18B-C), while wearing MRI-compatible fiducial markers around the abdomen and lower back. Second, customized pin-type electrode patches were applied to the same locations on the body surface as the MRI fiducial markers (FIG. 18D). Body surface electrical signals (FIG. 18E) were recorded for 20 minutes, and electrical signals (peristalsis wave signals FIG. 18F) were generated using a band-pass filter (0.01-0.1 Hz). Third, UPI software was used to generate electrical signals at each point on the entire 3D uterine surface (FIGS. 18G-H). These electrical signals were used to derive activation sequences, uterine potential maps, and uterine isochrone maps (FIGS.I-K). Finally, the uterine surface data were automatically analyzed to define the peristalsis direction (Cervix-Fundus, Fundus-Cervix, or other), initiation and termination sites (cervix area, fundus area, and other areas), and their distributions (FIG. 18L). Other UPI electrophysiological indices of uterine peristalsis include duration, magnitude, and power of peristalsis waves.

Figure 19A:
FIGS. 19A-I show uterine peristalsis imaging in one participant with regular menstrual cycles during four phases of the menstrual cycle. In the UPI activation sequences and isochrone maps, the white asterisks indicate the peristalsis wave initiation sites, and the white arrows indicate the propagation directions. *P<0.05.
Figure 19B:
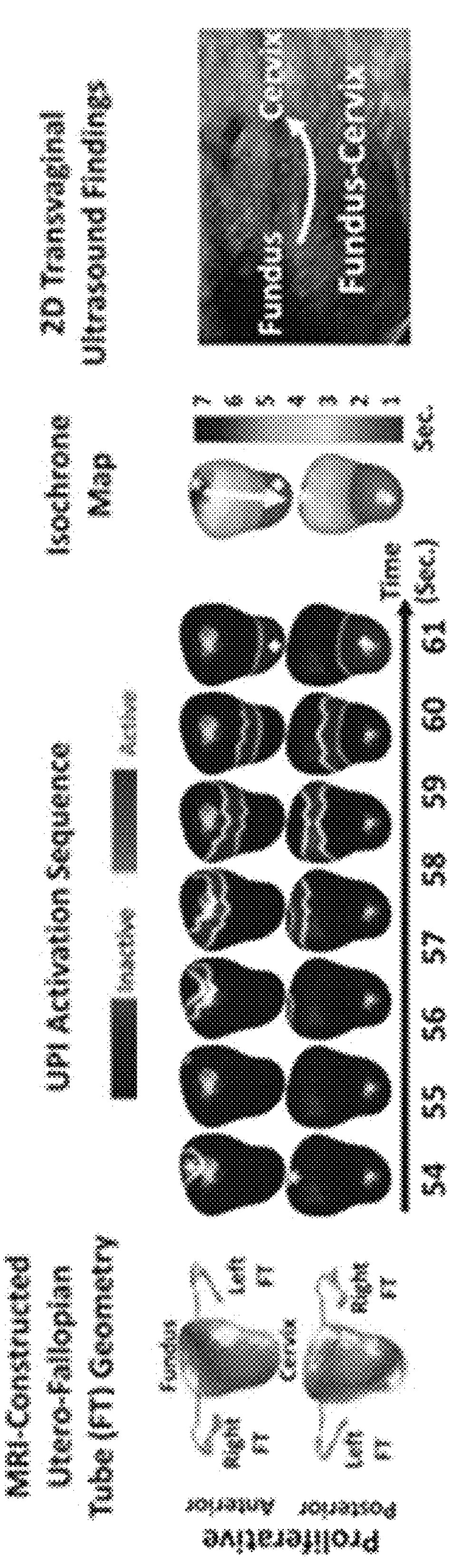
Figure 19C:
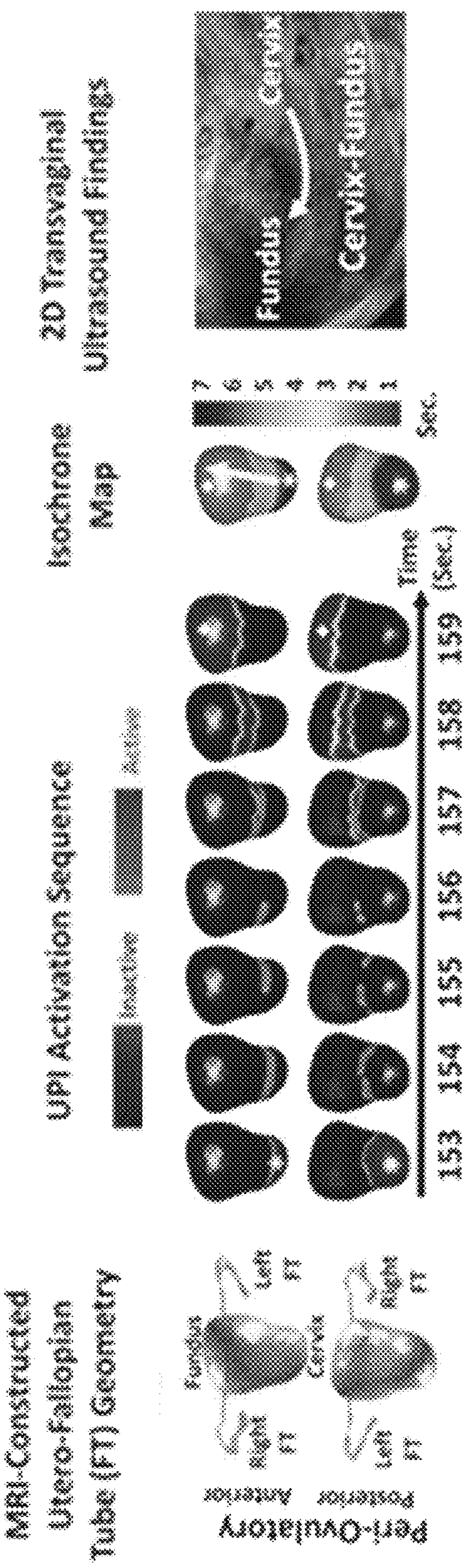
Figure 19D:
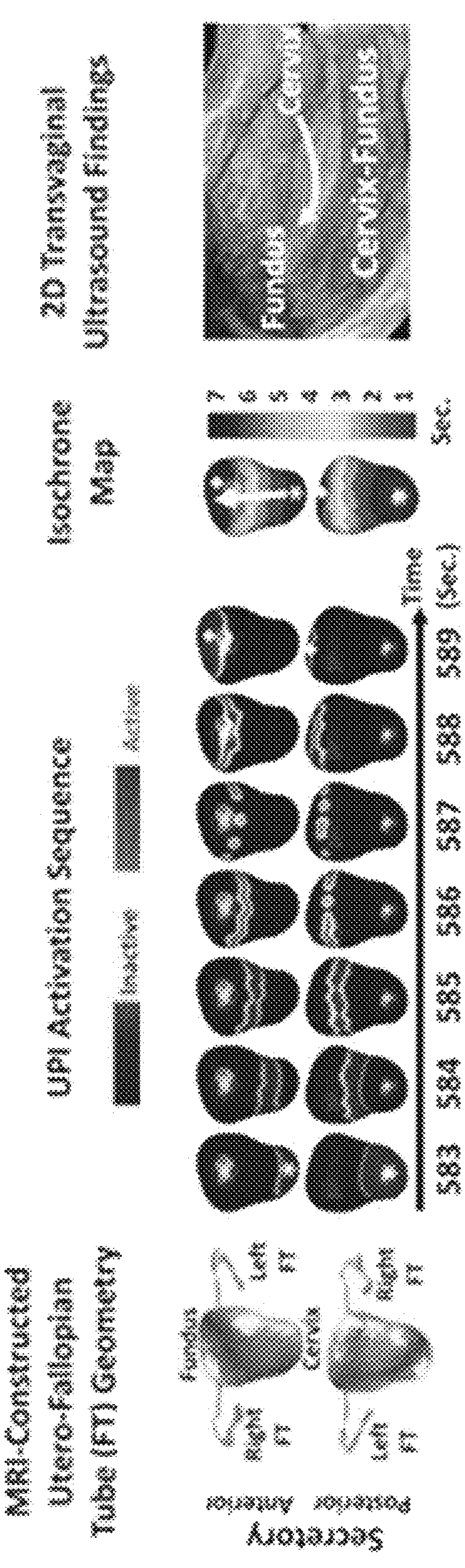
Figure 19E:
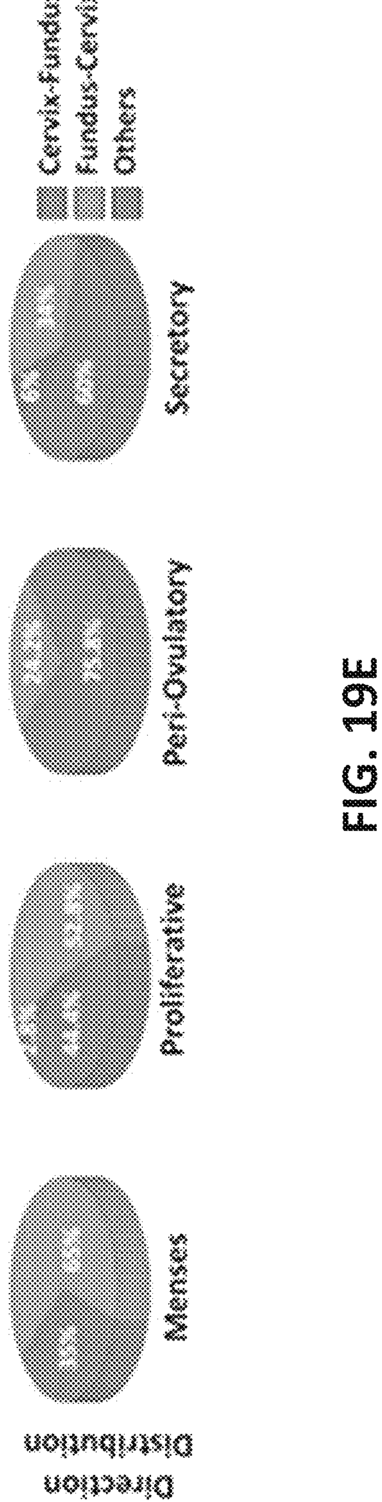
Figure 19F:
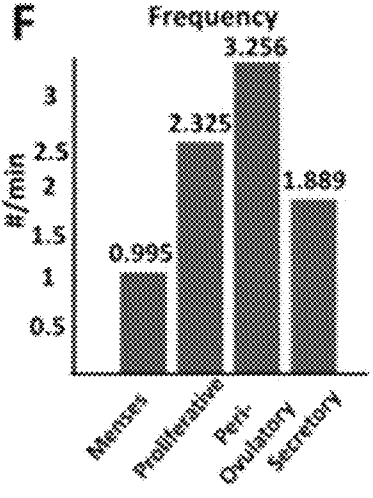
Figure 19G:
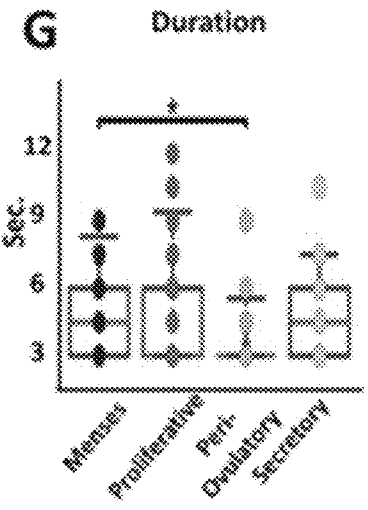
Figure 19H:
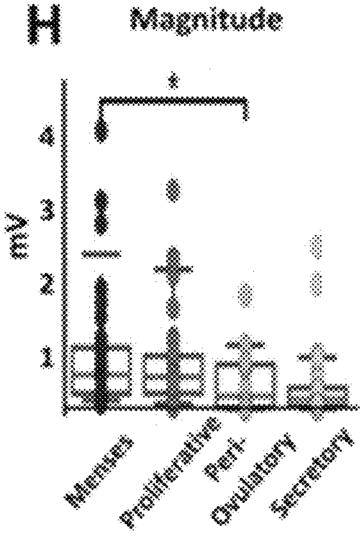
Figure 19I:
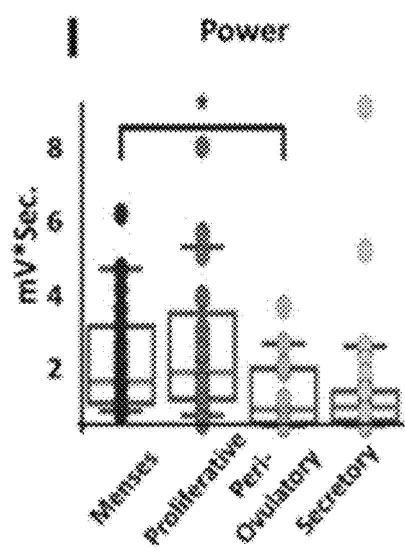

Uterine Peristalsis Imaging in Healthy Nonpregnant Participants with Normal Menstrual Cycles The UPI system was used to image uterine peristalsis during each menstrual cycle phase in 17 nonpregnant women with regular menstrual cycles. In total, 4968 uterine peristalses over 34 hours were imaged. In FIGS. 19A-I, representative uterine peristalsis waves are presented of a 26-year-old participant. During the menses phase, 65% of waves traversed from near the fundus toward the cervix, and 35% traversed from near the cervix toward the fundus (FIG. 19A). During the proliferative phase, 52.8% of waves were Fundus-Cervix and 44.4% were Cervix-Fundus (FIG. 19B). During the ovulatory phase, 75.8% of waves were Cervix-Fundus, and 24.2% were Fundus-Cervix (FIG. 19C). In the secretory phase, 60% of waves were Cervix-Fundus, and 34% were Fundus-Cervix (FIG. 19D). In all cases in which the direction of peristalsis in TVUS images (n=111) was determined, the direction of peristalsis imaged by UPI matched the direction observed by TVUS. Overall, uterine peristalsis waves during menses were significantly longer in duration and had greater magnitude and power than those during the ovulatory phase (FIG. 19F-I). Direction distributions of uterine peristalsis waves are shown in the pie charts in FID. 19E.

Uterine Peristalsis Imaging in Nonpregnant Participants with Endometriosis

The UPI system was used to image uterine peristalsis during each phase of the menstrual cycle in five nonpregnant women with surgically confirmed endometriosis. In total, 679 peristalses over 12.5 hours throughout the menstrual cycle were imaged. In FIGS. 20A-I, representative uterine peristalsis waves are presented of a 30-year-old participant with endometriosis. During the menses phase (FIG. 20A), 44.2% of waves were Fundus-Cervix, and 48.8% were Cervix-Fundus. During the proliferative phase (FIG. 20B), 36.3% of waves were Fundus-Cervix, and 42.2% were Cervix-Fundus. During the ovulatory phase (FIG. 20C), 59.9% of waves were Cervix-Fundus, and 25.4% were Fundus-Cervix. During the secretory phase (FIG. 20D), 47.8% of waves were Cervix-Fundus, and 50% were Fundus-Cervix. In all cases in which the direction of peristalsis in TVUS images (n=126) was determined, the direction of peristalsis imaged by UPI matched the direction observed by TVUS. Overall, uterine peristalsis waves during menses were significantly shorter in duration than those during the ovulatory phase and had greater magnitude and power than those during the secretory phases (FIG. 20F-I).

Comparison of Uterine Peristalsis During the Menstrual Cycle in Healthy Participants and Endometriosis Patients All the data from the healthy and endometriosis participants was compiled. The length of each participant's menstrual cycle was normalized to 28 days. Each participant's overall frequency and dominant direction ratio (the percentage of Cervix-Fundus peristalsis waves over the percentage of Fundus-Cervix peristalsis waves) (FIGS. 21A-B) were plotted. The average magnitude, duration, and power of peristalsis waves from each participant were graphed, with data from the Fundus-Cervix waves plotted separately from the data from Cervix-Fundus waves (FIGS. 21C-H). Significant differences were observed in multiple uterine peristalsis indices between healthy participants and those with endometriosis (FIGS. 21I-X). During the menses phase, peristalsis waves were significantly more likely to be Fundus-Cervix in healthy participants than in those with endometriosis (FIG. 21J). The Fundus-Cervix waves were longer (FIG. 21R) and had a higher magnitude (FIG. 21N) in healthy participants than in those with endometriosis. Conversely, the Cervix-Fundus waves were longer duration (FIG. 21Q) and higher magnitude (FIG. 21M) and power (FIG. 21U) in the participants with endometriosis than in the healthy patients. In the peri-ovulatory phase, peristalsis waves were more likely to be Cervix-Fundus in the healthy participants than in the participants with endometriosis (FIG. 21K), and the Cervix-Fundus waves were longer (FIG. 21S) and higher magnitude (FIG. 21O) and power (FIG. 21W) in the healthy participants than in those with endometriosis. Conversely, the Fundus-Cervix waves in the peri-ovulatory phase were longer duration (FIG. 21T) and higher magnitude (FIG. 21P) in the participants with endometriosis than in the healthy participants.

Peristalsis Wave Direction During Ovulation Correlates with Dominant Follicle Laterality Finally, it was observed that Cervix-Fundus peristalsis waves during the peri-ovulatory phase tend to move preferentially toward one fallopian tube. In nine of the healthy participants and two of the participants with endometriosis, it was determined which ovary had a dominant follicle by clinical TVUS. Then whether the peristalsis propagated in the direction of the dominant follicle was observed. FIG. 22A shows an example of UPI from a healthy participant with a dominant follicle in the right ovary. In this patient, 5 of 8 Cervix-Fundus peristalsis episodes moved toward the right ovary. The other 3 waves showed no preferential direction. FIGS. 22B-D show additional examples of healthy participants in which peristalsis patterns propagated toward the ovary with the dominant follicle. FIG. 22E shows an example of a participant with endometriosis and a dominant follicle in the left ovary. In this participant, 4 out of 5 peristalsis cycles progressed toward the right fallopian tube and 1 progressed toward the left fallopian tube. FIG. 22F shows a second participant with endometriosis and a dominant follicle in the left ovary. In this participant, 6 out of 13 Cervix-Fundus peristalsis waves moved in the direction of the right fallopian tube, while none moved toward the left fallopian tube.

In the eight healthy participants for whom TVUS imaging demonstrating the dominant follicle was obtained, peristalsis waves during the ovulatory phase more often moved toward the side with the dominant follicle than toward the side with no dominant follicle. In two participants with endometriosis for whom data was obtained regarding the dominant follicle, the peristalsis waves during the ovulatory phase more often moved toward the side without the dominant follicle than toward the side with the dominant follicle as illustrated in Table 6.

TABLE 6

Dominant follicle sides and sizes (measured from TVUS) and dominant unilateral UP directions in nine normal and two endometriosis subjects with available TVUS data.

| Cohort | Patient ID | Side of dominant follicle | Follicle size (cm) | Cervix-Fundus Uterine Peristalses Left | Right | Middle | Total Number |
|---|---|---|---|---|---|---|---|
| Normal | 1 | Right | 2.22 × 1.85 | 0.0% | 62.5% | 37.5% | 8 |
| Normal | 2 | Left | 1.99 × 1.91 | 72.4% | 20.7% | 6.9% | 29 |
| Normal | 3 | Right | 2.31 × 1.46 | 31.0% | 34.5% | 34.5% | 29 |
| Normal | 4 | Left | 1.63 × 1.43 | 82.1% | 10.7% | 7.1% | 28 |
| Normal | 5 | Left | 2.32 × 2.19 | 53.3% | 20.0% | 26.7% | 30 |
| Normal | 6 | Left | 2.38 × 1.70 | 91.7% | 4.2% | 4.2% | 24 |
| Normal | 7 | ND* | ND* | 0.0% | 80.0% | 20.0% | 5 |
| Normal | 8 | 2 on Left | 1.98 × 1.94, 1.80 × 1.64 | 55.2% | 31.0% | 13.8% | 29 |
| Normal | 9 | Left | 2.38 × 1.79 | 51.7% | 37.9% | 10.3% | 29 |
| Endometriosis | 1 | Left | 2.09 × 2.07 | 20.0% | 80.0% | 0.0% | 5 |
| Endometriosis | 2 | Left | 2.13 × 1.48 | 0.0% | 46.2% | 53.9% | 13 |

*ND, not determined. This patient had a teratoma on the right ovary preventing accurate assessment of the dominant follicle. No dominant follicle was observed on the left.

The UPI imaging data presented herein suggest that UPI can provide objective and quantitative measures of uterine peristalsis throughout the human menstrual cycle. Additionally, novel indices to quantitatively characterize uterine peristalsis patterns automatically were developed. Finally, UPI was used to provide evidence that uterine peristalsis patterns differ in women with normal anatomy and menstrual cycles and in women with endometriosis.

In the normal participants, the predominant peristalsis pattern in menses was Fundus-Cervix. This pattern has been seen by others and postulated to facilitate the expulsion of blood and endometrial tissue while protecting against ascending pathogens. In the peri-ovulatory phase, the predominant peristalsis pattern was Cervix-Fundus. A study used serial HSSG to follow labeled macrospheres the size of sperm and observed that they were transported from the cervix into the uterus and fallopian tubes, suggesting that the Cervix-Fundus peristalsis pattern facilitates the transport of sperm toward the oocyte. No predominant pattern in the proliferative and secretory phases was observed. The duration and magnitude of contractions differed in each phase. The rise in oxytocin and estrogen in the follicular phase may explain why the magnitude of the peristalsis pattern is increased during menses. After ovulation, during the secretory phase, progesterone (a known muscle relaxant) contributes to the decrease in the magnitude of peristalsis by antagonizing the estrogen and oxytocin receptors.

Endometriosis has long been hypothesized to be caused by retrograde menstruation. However, as all reproductive-age women have some amount of retrograde menstruation, it is unclear why only 10-15% of females would develop endometriosis. It was found that all healthy participants had at least some Cervix-Fundus peristalses, which could cause retrograde menstruation. The data suggested that Cervix-Fundus peristalsis waves were less frequent and weaker than the Fundus-Cervix waves in subjects without endometriosis. Therefore, the strong and frequent Fundus-Cervix waves may have effectively expelled blood vaginally and left a small amount of blood in the uterine cavity. Although part of the blood could still be transported retrogradely to the peritoneal space by the weak Cervix-Fundus waves, the level may not be sufficient to cause endometriosis in healthy people. On the contrary, in participants with endometriosis, a higher percentage of waves were Cervix-Fundus, and these were stronger and had longer durations than the Cervix-Fundus waves in normal patients. More importantly, in healthy subjects, the Fundus-Cervix peristalsis waves were less frequent and weaker in endometriosis patients than the Fundus-Cervix peristalsis waves, which impair normal expulsion and leave more blood in the uterine cavity. Therefore, retrograde menstruation is more likely to push much more blood and tissue into the peritoneal space in women with endometriosis than in women without endometriosis. This work suggests that a comprehensive evaluation of 4D uterine peristalsis direction distribution, frequency, magnitude, duration, and power during the menses phase can be used to stratify the risk of developing endometriosis and assess the severity of endometriosis.

The data may also provide clues to infertility in women with endometriosis. In healthy participants during the peri-ovulatory phase, uterine peristalsis waves most frequently traveled Cervix-Fundus, with most peristalsis waves traveling toward the dominant follicle. These patterns could assist sperm in transit to ensure interaction with an oocyte. Conversely, in participants with endometriosis during the peri-ovulatory phase, uterine peristalsis waves most frequently traveled Fundus-Cervix, and those that traveled Cervix-Fundus traveled toward the ovary without a dominant follicle more often than toward the ovary with a dominant follicle. These patterns could limit the number of spermatozoa that reach the oocyte.

The UPI system has a wide range of possible clinical research and therapeutic applications. UPI can be used to further establish reference baseline parameters of uterine peristalsis in normal menstrual cycles. These baseline values could be used to create a composite score to identify patients with abnormal gynecological conditions such as endometriosis, ovulatory dysfunction, abnormal uterine bleeding, or amenorrhea. Additionally, UPI can be used to correlate the dominant follicle with uterine peristalsis direction in the peri-ovulatory phase and to develop a predictive biomarker for successful natural conception. With the detailed 4D electrical activation patterns imaged by UPI, longitudinally evaluation of the treatment effects of various clinical interventions and optimization of the treatment plan for an individual patient can be conducted. In addition, UPI may facilitate the development of nonpharmaceutical treatments to electrically correct abnormal uterine peristalsis underlying various gynecological conditions, such as endometriosis, etc., using electronic devices similar to cardiac pacemakers.

UPI has several advantages over other modalities used to image uterine peristalsis. First, UPI is noninvasive, which is optimal for long-duration uterine monitoring. Additionally, modalities using invasive monitoring may iatrogenically cause non-physiologic perturbations of peristalsis. Second, UPI provides high spatial-temporal resolution information, including the initiation sites, direction, frequency, and duration of uterine peristalsis waves. Third, UPI provides 4D data that considers the individual's unique uterine anatomy in both space and time domains. Fourth, UPI software allows automatic, objective, and real-time electrophysiological quantification of uterine peristalsis.

Study Design and Participants

This study was conducted with participants that were female at birth, between the ages of 18 and 37 years. Normal participants were included if they had regular, predictable menstrual cycles every 24-35 days. Participants with endometriosis were included if they had surgically confirmed endometriosis. Potential participants were excluded if they were post-menopausal, pregnant, or breastfeeding; had a uterine anomaly; had exposure to medications known to affect uterine contractility (e.g., magnesium, opioids, beta antagonists, nifedipine); were non-English speaking; had abdominal circumference >55 cm; or had MRI contraindications (pacemaker, metal implants, etc.). Potential participants for the normal group were excluded if they had documented or self-reported histories of infertility, ovulatory dysfunction, or endometriosis. Potential participants for the endometriosis group were excluded if they were currently using female birth control. Seventeen out of them finished the longitudinal data acquisition and MRI study. Participants with regular menstrual cycles and five patients with endometriosis were enrolled in this study. Demographics and obstetric and gynecologic history of enrolled participants are shown in Table 7. Each participant was imaged with the UPI system four times during one menstrual cycle, once during menses, early proliferative, late proliferative (peri-ovulatory), and secretory phases. Blood was collected at each visit to measure concentrations of the hormones estradiol, progesterone, and testosterone to confirm the menstrual phase.

TABLE 7

Participant characteristics. Data are presented as n (%) or average (range).

| | |
|---|---|
| Age, years | 29.5 (22-37) |
| Body mass index | 28.57 (19.79-48.70) |
| **Race** | |
| White | 17 (77.3%) |
| Black or African American | 3 (13.6%) |
| Middle Eastern or North African | 1 (4.5%) |
| Asian | 1 (4.5%) |
| **OBGYN history** | |
| Gravida | 0.38 (0-3) |
| Parity | 0.24 (0-2) |
| Abortion-Spontaneous or elective | 0.14 (0-3) |
| Prior hysteroscopy | 1 (4.5%) |
| Prior C-Section | 1 (4.5%) |
| Prior Salpingectomy | 2 (9.1%) |
| Fallopian tube removed | 2 (9.1%) |
| Confirmed tubal patency | 2 (9.1%) |
| **Health conditions** | |
| Chronic health condition | 16 (72.7%) |
| Asthma | 3 (13.6%) |
| Anxiety or depression | 13 (59.1%) |

Definition of Menstrual Phases

Patients were determined to be in one of four menstrual phases (menses, early proliferative, late proliferative, and secretory) by using a combination of patient-reported bleeding, cycle length, ultrasound findings, ovulation predictor kit results, and hormonal measurements. Serum blood (5-10 ml) was collected and sent to a lab to measure concentrations of the hormones (estradiol, progesterone, and testosterone). The menses phase was assigned when a patient-reported bleeding. The early proliferative phase was assigned after the patient had stopped bleeding, ultrasound demonstrated early follicular activity (largest follicle size <16 mm), serum estradiol <200 pg/ml, and serum progesterone <3 ng/ml. The late proliferative (peri-ovulatory) phase was defined by a positive result on an ovulation predictor kit, serum estradiol >200 pg/ml, serum progesterone <3 ng/ml, and/or a dominant follicle on ultrasound (≥16 mm). The secretory phase was assigned when serum progesterone was >3 ng/ml.

Uterine Peristalsis Imaging (UPI) Procedure

First, a woman underwent a one-time, fast, anatomical (T2W sequence) 3T Siemens Prisma MRI scan (~10 mins) to acquire the patient-specific uterus-body surface geometry while wearing up to 8 patches containing up to 128 MRI-compatible fiducial markers around the abdomen and lower back (FIG. 18A). Uterus and body geometry were generated (FIGS. 18B-C). Second, after the MRI scan, customized BioSemi pin-type electrode patches were applied to the same locations on the body surface as the MRI fiducial markers. An ADC box was used to record the body surface electrical signals (FIGS. 18D-E) for 20 minutes. The body surface electrical signals were processed with a band-pass filter (0.01-0.1 Hz) to generate wave electrical signals (peristalsis waves) over the entire abdomen surface (FIG. 18F). Third, the participant underwent another 10-minute electrical recording while simultaneously undergoing transvaginal ultrasound (TVUS). TVUS scans of the uterus were performed by the sonographer holding the transducer probe while the patient was lying in a lithotomy position, and TVUS clips were recorded on a GE Voluson S8 ultrasound machine. The duration of each clip was 20 seconds on average, and 30-35 clips were acquired in total. A registered sonographer independently (without knowledge of the UPI results) examined the TVUS recordings to determine the uterine peristalsis direction.

Inverse Computation in UPI

With the electro-quasi-static assumption of the bioelectric field, the inverse computation combines the patient-specific uterus-abdomen surface and electrical potentials measured on the abdominal surface to reconstruct the potential distribution over the entire 3D uterine surface. It is assumed that the medium is homogeneous between the uterine surface and abdominal surface without any primary electrical source. Then, the inverse problem could be mathematically described by the Cauchy problem for Laplace's equation (12) with boundary conditions (13,14) on the abdominal surface.

$$\nabla^2 \phi(x) = 0 \tag{12}$$

Dirichlet (2) and Neumann (3) conditions for the abdominal surface potentials are:

$$\phi(x) = \phi_{A(x)},\ x \in \Gamma_A \tag{13}$$

$$\frac{\partial \phi(x)}{\partial n} = 0,\ x \in \Gamma_A \tag{14}$$

Here, n is the normal vector on the abdominal surface at location x and $\Gamma_A$ represents abdominal surface. $\phi_{A(x)}$ is the potential measured on the abdominal surface and $\phi(x)$ is the potential on the uterine surface.

As a mesh-free method robust to noise, a method of fundamental solutions (MFS) was deployed to discretize the Laplace's equation and boundary conditions, which is accurate for solving the bioelectric field inverse problem in both electrocardiographic imaging (ECGI) and electromyometrial imaging (EMMI) systems. This problem cannot be solved directly as it is an ill-posed inverse problem. Therefore, Tikhonov-based inverse computation with a fixed regularization value of 0.01 was used to obtain the solution.

$$\Phi_A = A\,\Phi_U \tag{15}$$

Here, $\Phi_A$ is a M*T matrix of measuring surface potentials, $\Phi_U$ is a N*T matrix of uterine surface potentials, where M is the number of measuring electrodes applied on the abdominal surface and N is the number of discrete points on the uterine surface, and T is the number of recording time points. A is a M*N linear transform matrix encoding the relationship between abdominal surface potential $\Phi_A$ and uterine surface potential $\Phi_U$.

UPI Data Processing

The inverse computation described above was employed to compute the uterine surface electrical signals (FIGS. 18G-H) on the three-dimensional uterine surface. The times when the uterine surface electrical signals at various uterine surface areas reached the steepest negative slope were extracted and defined as electrical activation times at those uterine areas during peristalsis waves (red dots in FIGS. 18G-H). During each peristalsis wave, sequential time frames were generated as the activation sequences (FIG. 18I) to reflect the detailed 4D spatial-temporal activation patterns of the uterine peristalsis. Within each time frame, the red region indicated the electrically activated myometrium areas currently experiencing peristalsis, and the blue region indicated the inactive areas of the uterus. The isochrone map was generated as a color-coded 3D map to summarize the electrical activation sequence (FIG. 18J). In the isochrone map, warm and cool colors denote regions of the uterus that activated early and late, respectively, during the peristalsis wave. The UPI isochrone maps contained rich spatial-temporal information of uterine activation, including the activation and termination sites, propagation direction, and duration. In addition, uterine potential maps were generated to reflect the 4D electrical potential distribution during peristalsis waves: 1D electrical signals (FIGS. 18G-H) over the entire 3D uterine surface (FIG. 18K). The distributions of uterine peristalsis propagation direction, initiation, and termination sites (FIG. 18L) were automatically calculated as the number of peristalsis waves with a specific propagation direction (Fundus-Cervix, Cervix-Fundus or other), initiation, and termination site (cervical, fundal or other regions) divided by the total number of peristalsis waves in the 20-minute electrical mapping session, respectively.

Electrophysiological Characterization and Quantification of Human Uterine Peristalsis Five UPI electrophysiological indices were defined to qualitatively and quantitatively describe uterine peristalsis patterns. First, the propagation direction was determined from the uterine peristalsis activation maps. Uterine peristalsis directions were classified into three categories: Fundus-Cervix, Cervix-Fundus, and others including Anterior-Posterior, Posterior-Anterior, Left-Right, and Right-Left.

Second, the initiation and termination sites were defined as the region experiencing the earliest and latest activation during uterine peristalsis. The initiation and termination sites were identified on the isochrone maps and were classified into three categories: Cervical region, Fundal region, and Other regions. Third, the duration (Sec.) was defined as the duration of a complete peristalsis wave measured in the isochrone map of the uterine peristalsis wave. A small fraction of uterine peristalsis waves only involve the partial activation of the uterus and has a relatively shorter duration. Fourth, uterine peristalsis magnitude (mV) was defined as the average peak amplitude of electrical potential over the uterine region experiencing activation during the entire peristalsis wave. Finally, uterine peristalsis power (mV*sec) was defined as the product of magnitude and duration for each uterine peristalsis.

Definition of Cervix-Fundus Uterine Peristalsis Wave Laterality

The distance between the latest fundus-activated uterine site and the left fallopian tube insertion site was defined as $d_{left}$, the distance between the latest fundus-activated uterine site and the right fallopian tube insertion site was defined as $d_{right}$. The ratio between these two distances was defined as $$R = \frac{d_{left}}{d_{right}}.$$

If R<0.8, the cervix-fundus uterine peristalsis was left dominant; if R>1.25, the cervix-fundus uterine peristalsis was right dominant; if 0.8<R<1.25, the cervix-fundus uterine peristalsis was middle dominant with no side preference.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. A method for monitoring uterine peristalsis of a non-pregnant uterus of a mammal during at least one uterine contraction, the mammal having a body surface surrounding the uterus, the method comprising:

applying a first patch to a plurality of locations on the body surface, the first patch associated with a plurality of imaging markers;

performing a first imaging scan of the uterus of the mammal, wherein the first imaging scan generates a first set of three-dimensional images representing the body surface and uterus of the mammal;

applying a second patch to the plurality of locations on the body surface, the second patch associated with an electrical recording device and an optical scanner, wherein the first patch is removed before applying the second patch to the plurality of locations;

performing a second imaging scan of the uterus of the mammal, the second imaging scan associated with the optical scanner, wherein the second imaging scan generates a second set of three-dimensional images representing the body surface and uterus of the mammal;

recording body surface electrical potentials via the electrical recording device during the at least one uterine contraction, the recording device in electrical communication with the second patch;

performing a third imaging scan of the uterus of the mammal, wherein the third imaging scan generates a set of two-dimensional images representing the body surface and uterus of the mammal;

identifying a body-uterus geometry of the mammal based on at least one of the first and second set of generated three-dimensional images and the set of generated two-dimensional images;

generating at least one body surface electrical potential map based on the identified body-uterus geometry and the body surface electrical potentials recorded at the plurality of locations by the electrical recording device during the at least one uterine contraction; and reconstructing the first and second set of three-dimensional images to provide a third set of three-dimensional images representative of uterine peristalsis electrical activity of the non-pregnant uterus of the mammal during the at least one uterine contraction based on the identified body-uterus geometry of the mammal and the recorded body surface electrical potentials.

2. The method of claim 1, wherein at least a portion of the plurality of imaging markers are visible in at least a portion of the first set of generated three-dimensional images.

3. The method of claim 1, wherein the plurality of locations includes at least 8 locations on the body surface of the mammal.

4. The method of claim 1, wherein the first imaging scan is an MRI scan, the first set of generated three-dimensional images comprise MRI images, and the plurality of imaging markers comprises MRI markers.

5. The method of claim 1, wherein the first patch comprises a plurality of electrodes comprising up to 64 electrodes.

6. The method of claim 5, wherein the number of the plurality of markers is equal to the number of the plurality of electrodes.

7. The method of claim 1, wherein the first and second patches are releasably secured and operably connected to a wearable device.

8. The method of claim 1, wherein the reconstructed three-dimensional images include at least one of a uterine surface electrical potential map, a set of electrograms, and a set of isochrone maps.

9. The method of claim 1, wherein the third imaging scan is a transvaginal ultrasound.

10. A system for monitoring uterine peristalsis of a non-pregnant uterus of a mammal during at least one uterine contraction, the system comprising:

a first patch operable to be secured to a plurality of locations on a body surface, the first patch associated with a plurality of imaging markers;

a first imaging modality of the uterus of the mammal, wherein the first imaging modality generates a first set of three-dimensional images representing the body surface and uterus of the mammal;

a second patch operable to replace the first patch at the plurality of locations on the body surface, wherein the first patch is removed before applying the second patch to the plurality of locations;

a second imaging modality of the uterus of the mammal, the second imaging modality associated with an optical scanner, wherein the second imaging modality generates a second set of three-dimensional images representing the body surface and uterus of the mammal;

an electrical recording device in electrical communication with the second patch, the electrical recording device configured to record body surface electrical potentials during the uterine contraction and to record a plurality of electrical signals on the body surface surrounding the uterus of the mammal during the uterine contraction;

a third imaging modality of the uterus of the mammal, wherein the third imaging modality generates a set of two-dimensional images representing the body surface and uterus of the mammal;

identifying a body-uterus geometry of the mammal based on at least one of the first and second set of generated three-dimensional images and the set of generated two-dimensional images; and at least one non-transitory computer readable medium storing instructions which when executed by at least one processor, cause the at least one processor to:

receive the first set of generated three-dimensional images from the first imaging modality;

determine the plurality of locations based on the imaging markers visible in the first set of generated three-dimensional images;

receive the second set of generated three-dimensional images from the second imaging modality;

receive the set of generated two-dimensional images from the third imaging modality;

determine a body-uterus geometry of the mammal based on the first and second sets of three-dimensional images, the set of two-dimensional images, and the plurality of locations;

receive the plurality of electrical signals from the electrical recording device; and generate at least one of a body surface electrical potential map based on the body-uterus geometry and the plurality of electrical signals.

11. The system of claim 10, wherein the first patch is associated with a plurality of imaging markers and at least a portion of the plurality of imaging markers are visible in at least a portion of the first set of generated three-dimensional images.

12. The system of claim 11, wherein at least a portion of the image markers are MRI image markers.

13. The system of claim 10, wherein the plurality of locations includes at least 8 locations on the body surface of the mammal.

14. The system of claim 10, wherein the first imaging modality is an MRI scan, the first set of generated three-dimensional images comprise MRI images, and the plurality of imaging markers comprise MRI markers.

15. The system of claim 10, wherein the second patch comprises a plurality of electrodes.

16. The system of claim 10, further comprising a plurality of first patches and a plurality of second patches, wherein the number of the first patches is equal to the number of the second patches, the first patches comprising at least one imaging marker and the second patches comprising at least one electrode.

17. The system of claim 10, wherein the first and second patches are releasably secured and operably connected to a wearable device.

18. The system of claim 10, wherein the at least one generated three-dimensional body surface electrical potential map is an electrical potential map, an electrogram, or an isochrone map.

19. The system of claim 10, wherein the third imaging modality is a transvaginal ultrasound.

20. A method for monitoring uterine peristalsis of a non-pregnant uterus of a mammal during at least one uterine contraction, the mammal having a body surface surrounding the uterus, the method comprising:

applying a plurality of imaging markers to a plurality of locations on the body surface, each one of the plurality of imaging markers applied to one of the plurality of locations;

performing a first imaging scan of the uterus of the mammal, the first imaging scan operable to generate a first plurality of generated three-dimensional images of the body surface and uterus of the mammal;

determining a first body-uterus geometry of the mammal based on the first plurality of generated three-dimensional images;

replacing each one of the plurality of imaging markers applied to one of a plurality of locations, with one of a plurality of electrodes, each one of the plurality of electrodes associated with a second imaging scan and an electrical recording device;

performing the second imaging scan of the uterus of the mammal, the second imaging scan operable to generate a second plurality of generated three-dimensional images of the body surface and uterus of the mammal;

determining a second body-uterus geometry of the mammal based on the second plurality of generated three-dimensional images;

recording body surface electrical potentials via the electrical recording device during the at least one uterine contraction, the recording device in electrical communication with the plurality of electrodes;

performing a third imaging scan of the uterus of the mammal, the third imaging scan operable to generate a plurality of generated two-dimensional images of the body surface and uterus of the mammal;

generating a plurality of body surface electrical potential maps based on at least one of the first and second body-uterus geometries, the plurality of generated two-dimensional images, and the plurality of body surface electrical potentials detected at the plurality of locations during the at least one uterine contraction; and reconstructing at least one of the first and second plurality of generated three-dimensional images to provide a plurality of reconstructed three-dimensional images representative of uterine peristalsis electrical activity of the uterus of the mammal during the at least one uterine contraction from the body-uterus geometry of the mammal and the plurality of body surface electrical potentials.

* * * * *